US011279926B2

United States Patent
Lane et al.

(10) Patent No.: US 11,279,926 B2
(45) Date of Patent: Mar. 22, 2022

(54) METHODS AND COMPOSITIONS FOR GENERATING CRISPR/CAS GUIDE RNAS

(71) Applicant: The Regents of the University of California, Oakland, CA (US)

(72) Inventors: Andrew B. Lane, Berkeley, CA (US); Rebecca Heald, Berkeley, CA (US)

(73) Assignee: The Regents of the University of California, Oakland, CA (US)

( * ) Notice: Subject to any disclaimer, the term of this patent is extended or adjusted under 35 U.S.C. 154(b) by 228 days.

(21) Appl. No.: 15/765,420

(22) PCT Filed: Jun. 2, 2016

(86) PCT No.: PCT/US2016/035534
§ 371 (c)(1),
(2) Date: Apr. 2, 2018

(87) PCT Pub. No.: WO2016/196805
PCT Pub. Date: Dec. 8, 2016

(65) Prior Publication Data
US 2018/0273935 A1 Sep. 27, 2018

Related U.S. Application Data

(60) Provisional application No. 62/221,836, filed on Sep. 22, 2015, provisional application No. 62/171,976, filed on Jun. 5, 2015.

(51) Int. Cl.
| | | |
|---|---|---|
| C12N 15/10 | (2006.01) | |
| C12P 19/34 | (2006.01) | |
| C12N 15/52 | (2006.01) | |
| C12N 15/11 | (2006.01) | |
| C12N 15/09 | (2006.01) | |
| C12Q 1/68 | (2018.01) | |
| C12N 9/22 | (2006.01) | |
| C12N 15/113 | (2010.01) | |
| C12Q 1/6855 | (2018.01) | |
| C40B 40/06 | (2006.01) | |
| C40B 50/08 | (2006.01) | |

(52) U.S. Cl.
CPC .......... *C12N 15/1093* (2013.01); *C12N 9/22* (2013.01); *C12N 15/09* (2013.01); *C12N 15/111* (2013.01); *C12N 15/113* (2013.01); *C12N 15/52* (2013.01); *C12P 19/34* (2013.01); *C12Q 1/68* (2013.01); *C12Q 1/6855* (2013.01); *C40B 40/06* (2013.01); *C40B 50/08* (2013.01); *C12N 2310/20* (2017.05); *C12Q 2521/301* (2013.01); *C12Q 2521/313* (2013.01); *C12Q 2525/191* (2013.01)

(58) Field of Classification Search
CPC ................................................ C12N 2310/20
See application file for complete search history.

(56) References Cited

U.S. PATENT DOCUMENTS

2003/0207282 A1* 11/2003 Bradbury ............... C12Q 1/686
435/6.1
2014/0072961 A1* 3/2014 Schiller ............... C12N 15/102
435/5

FOREIGN PATENT DOCUMENTS

| WO | WO 2005/042781 | 5/2005 |
| WO | WO 2014/110006 | 7/2014 |
| WO | WO 2015/040075 | 3/2015 |

OTHER PUBLICATIONS

Ariazi et al. (1996) Consecutive Cycles of Precise, Unidirectional 14-bp Deletions Using a BseRI/Bsgl Trimming . Biotechniques, 20:446-451 (Year: 1996).*
Koike-Yusa et al. (2014) Genome-wide recessive genetic screening in mammalian cells with a lentiviral CRISPR-guide RNA library. Nature Biotechnology, 32(3):267-273 (Year: 2014).*
Doench, et al.; "Rational design of highly active sgRNAs for CRISPR-Cas9-mediated gene inactivation"; Nature Biotechnology; vol. 32, No. 12, pp. 1262-1267 (Dec. 2014).
Jiang, et al.; "Demonstration of CRISPR/Cas9/sgRNA-mediated targeted gene modification in *Arabidopsis*, tobacco, sorghum and rice"; Nucleic Acids Research; vol. 41, No. 20, pp. 1-12 (Sep. 2, 2013).
Lane, et al.; "Enzymatically Generated CRISPR Libraries for Genome Labeling and Screening"; Cell; vol. 34, pp. 373-378 (Aug. 10, 2015).
Xing, et al.; "A CRISPR/Cas9 toolkit for multiplex genome editing in plants"; BMC Plant Biology; vol. 14, No. 327, 12 pages (2014).

* cited by examiner

*Primary Examiner* — Neil P Hammell
(74) *Attorney, Agent, or Firm* — Bozicevic Field & Francis, LLP; Paula A. Borden

(57) ABSTRACT

The present disclosure provides methods, kits, and compositions for generating DNA molecules encoding CRISPR/Cas guide RNAs (e.g., Cas9 single guide RNAs or Cas9 targeter RNAs). A library of such DNA molecules can be generated from any DNA source. The methods include a step of contacting target DNA with one or more DNA endonucleases that specifically bind to and cleave within a recognition sequence that includes a PAM sequence, to generate a plurality of cleavage fragments, to which a DNA adapter can be attached. A distal-cleaving DNA endonuclease can be used that specifically binds to a recognition sequence in the DNA adapter and cleaves at a site within the attached DNA cleavage fragments to generate a library of CRISPR/Cas guide sequences. After removal of all or a portion of the DNA adapter, a constant region of a guide RNA can be attached to generate DNA molecules encoding CRISPR/Cas guide RNAs.

15 Claims, 16 Drawing Sheets

Specification includes a Sequence Listing.

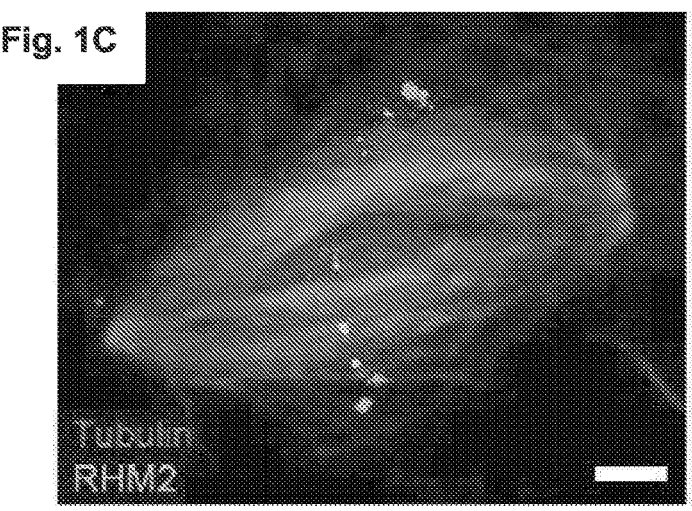
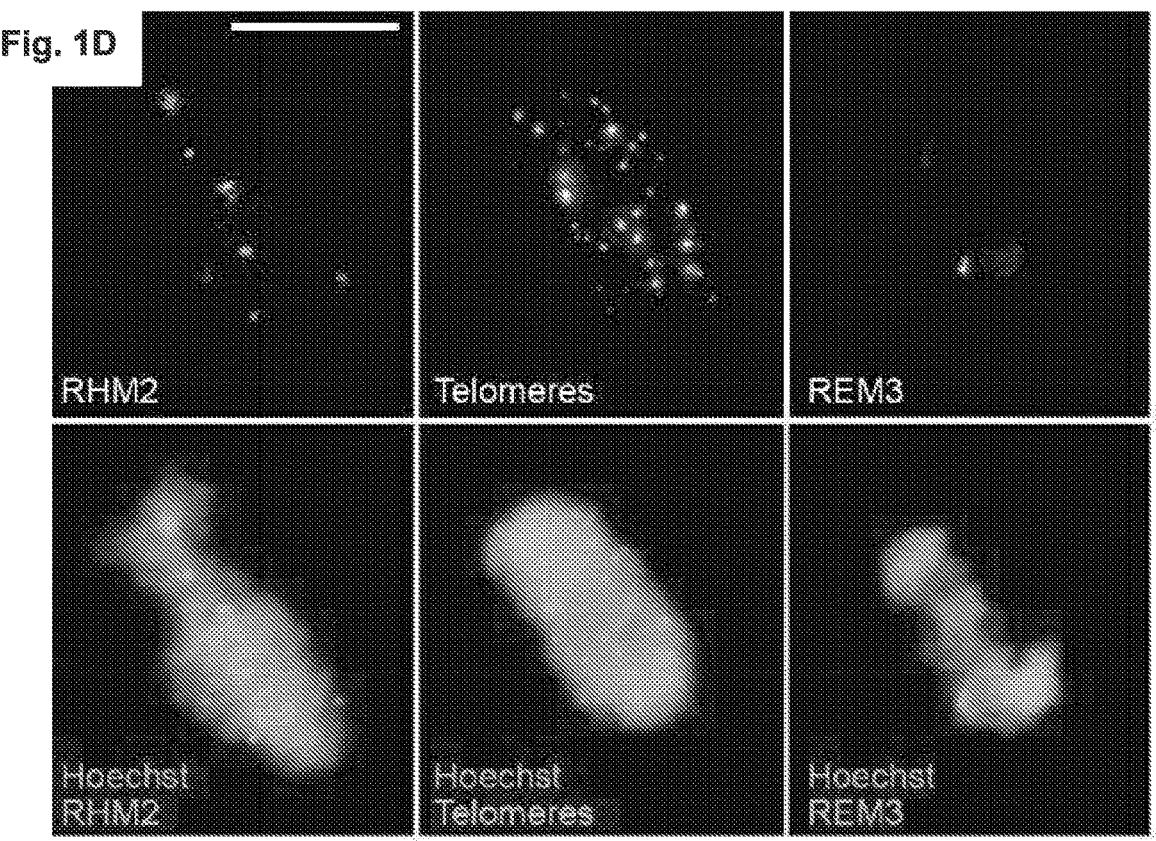
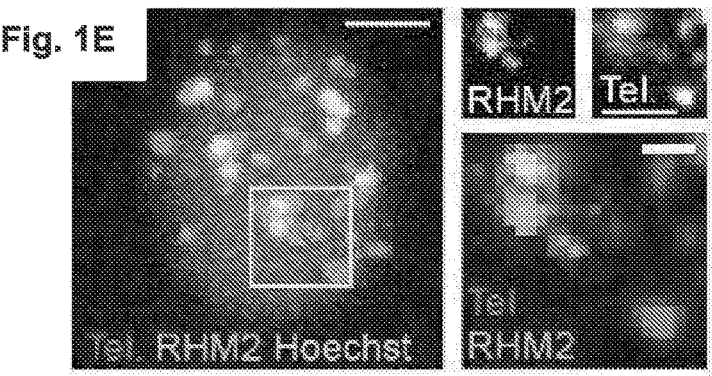

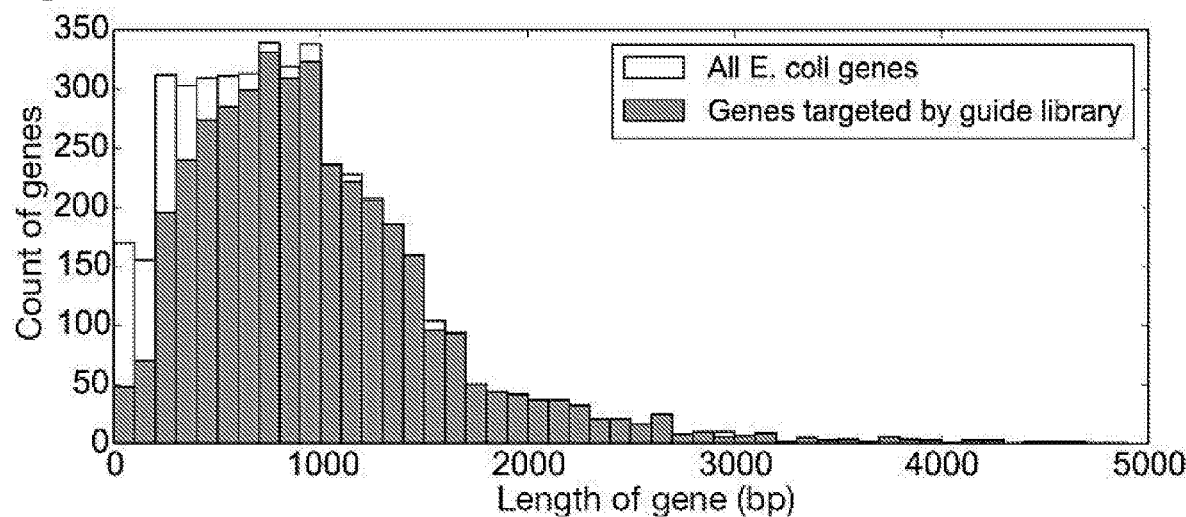
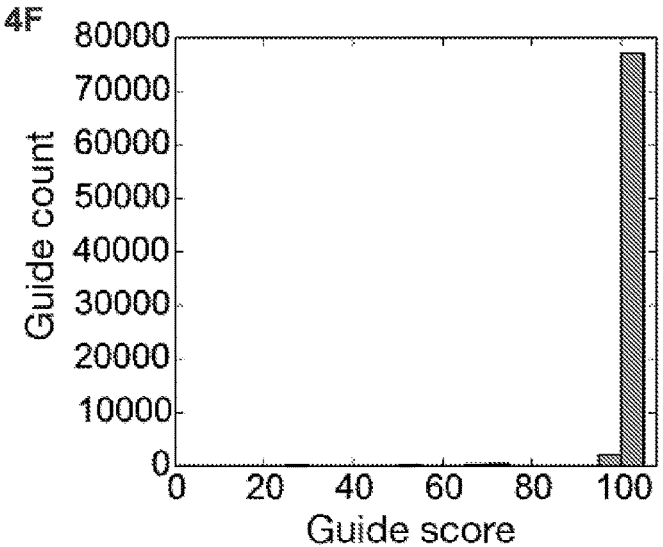

Fig. 8A

Template DNA cleavage using PAM-adjacent DNA endonuclease(s); in some cases followed by blunting (e.g., use nuclease to remove single stranded overhang DNA, e.g., mung bean nuclease)

Cleavage fragments:
(in some cases, mean length ~130bp)

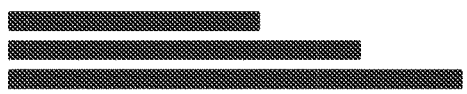

Adapter 1 attachment
(Adapter can include:
(i) recognition site 1 for a distal-cleaving DNA endonuclease)
(e.g, MmeI site); and
(ii) recognition site 2 for removal of Adapter 1 (e.g., BsaXI site)

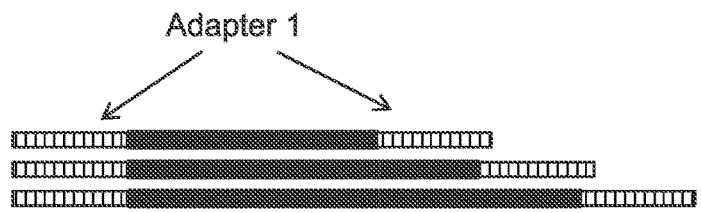

Cleavage with distal-cleaving DNA endonuclease (using site 1)

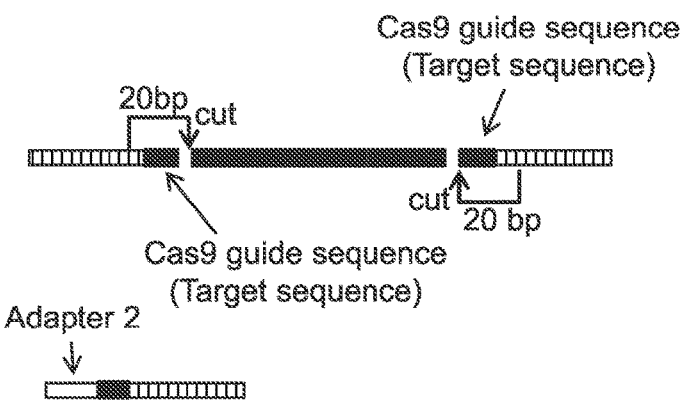

Optional: Adapter 2 attachment (adds, e.g., one or more of: a promoter such as T7, a recognition site for cloning or circularization, an overhang for circularization, etc.)

Cleavage with endonuclease to remove Adapter 1 (using recognition site 2)

Attachment of DNA encoding a constant region of a Cas9 targeter RNA or a Cas9 sgRNA

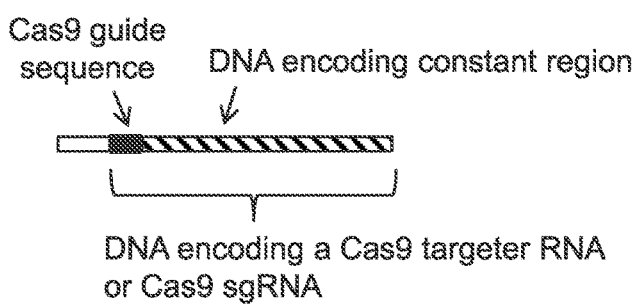

Fig. 8B

Template DNA cleavage using PAM-adjacent DNA endonuclease(s); in some cases followed by blunting (e.g., use nuclease to remove single stranded overhang DNA, e.g., mung bean nuclease)

Cleavage fragments:
(in some cases, mean length ~130bp)

Adapter 1 attachment
(Adapter can include:
(i) recognition site 1 for a distal-cleaving DNA endonuclease) (e.g, MmeI site);
(ii) recognition site 2 for removal of adapter sequences (e.g., BsaXI site);
(iii) a sequence encoding a constant region of a Cas9 targeter RNA or a Cas9 sgRNA; and (iv) a recognition site or overhang for circularization This end not illustrated Adapter 1

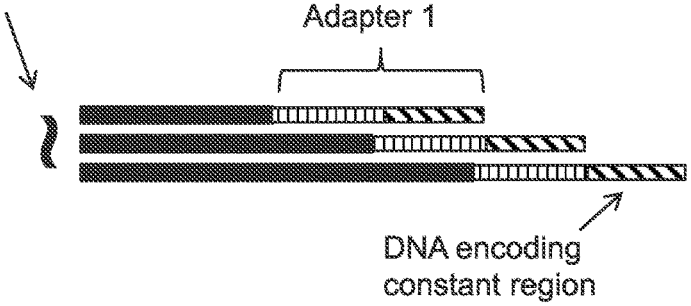

DNA encoding constant region

Cleavage with distal-cleaving DNA endonuclease
(using recognition site 1)

This end not illustrated

Cas9 guide sequence (Target sequence)

cut
20 bp

Optional: Adapter 2 attachment (adds, e.g., a recognition site or overhang for circularization and optionally a promoter such as a T7 promoter)

Adapter 2

Circularization
(e.g., ligation of ends)

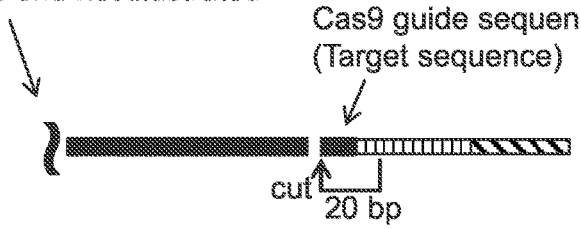

DNA encoding a Cas9 targeter RNA or Cas9 sgRNA

Removal of intervening adapter sequence and re-circularization cut → re-circularize

Fig. 9A

Adapter 1

```
         Mmel site      BsaXI site                              ScrFI site                                              BsaXI site                   Mmel site
cleave                                                   (to remove self-ligated adapters)                                                              cleave
                                                         (Recognition site for a PAM-
                                                         recognition DNA endonuclease)
5'  GTTGGATAGTGTACTGCGGCTCCAGGACCAGGATCTTAGATAGTAATCAACAGCCCCTCCTAATTCCAAC  3'    (SEQ ID NO: 1)
3'  CAACCTATCACATGACGCCGAGGTATCGATCGAGTCCTGGTCCTAGAATCTATCATTAGTTGTCGGGGAGGATTAAGGTTG  5'   (SEQ ID NO: 2)
```

Adapter 2

```
                          T7 RNA Polymerase promoter
(SEQ ID NO: 3)
Top:    5'  gaaatTAATACGACTCACTATAGNN  3'
Bottom: 3'  ctttaATTATGCTGAGTGATATC    5'
(SEQ ID NO: 4)
```

Adapter 3 (DNA Linker)  (DNA molecule that includes a constant region of a Cas9 sgRNA)

```
(SEQ ID NO: 5)
Top: 5'    TAAGAGCTATGCTGAAACAGCATAGCAAGTTTAAATAAGGCTAGTCCGTTATCAACTTGAAAAAGTGGCACCGAGTCGGTGCTTTTTT  3'
Btm: 3'  CAAATTCTCGATACGACTTTGTCGTATCGTTCAAATTTATTCCGATCAGGCAATAGTTGAACTTTTTCACCGTGGCTCAGCCACGAAAAAAA  5'
(SEQ ID NO: 6)
```

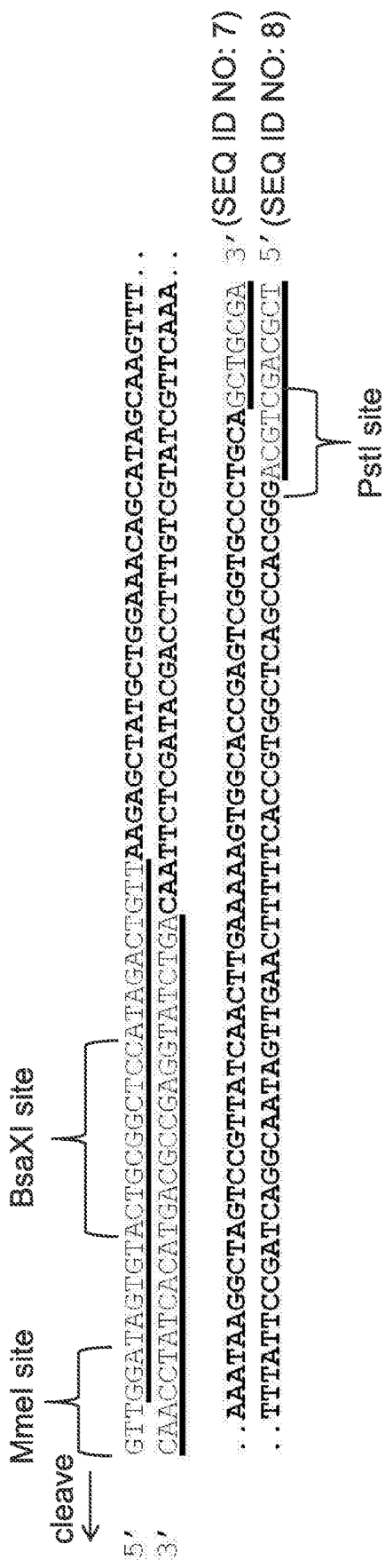
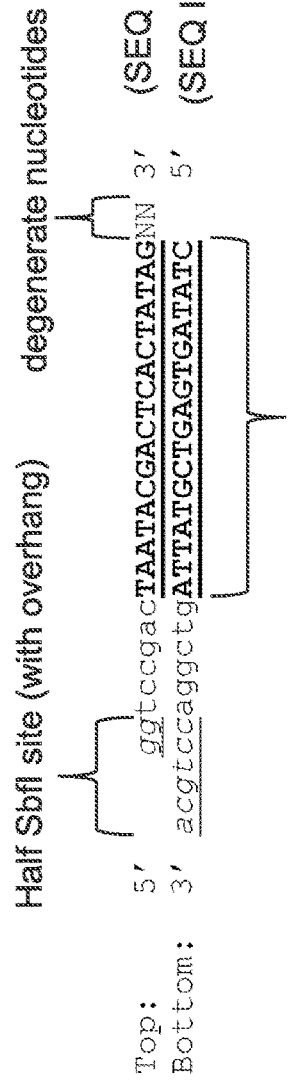
Fig. 9B

Fig. 10

Mmel

5' - TCCRAC (N)$_{20}$ .........▼....- 3'  (SEQ ID NO:1418)
3' - AGGYTG (N)$_{18}$ ..........- 5'  (SEQ ID NO:1419)
                         ▲ where R is a purine (e.g., A, G)

where Y is a pyrimadine (e.g., C, T)

BsaXI

5' ......▼$_9$(N) AC (N)$_5$ CTCC (N)$_{10}$ .........▼- 3'  (SEQ ID NO:1420)
3' ...... $_{12}$(N) TG (N)$_5$ GAGG (N)$_7$ ...▲.....- 5'  (SEQ ID NO:1421)
   ▲

METHODS AND COMPOSITIONS FOR GENERATING CRISPR/CAS GUIDE RNAS

CROSS-REFERENCE

This application is a national stage application under 35 U.S.C. § 371 of International PCT Patent Application No. PCT/US2016/035534, files Jun. 2, 2016, which claims the benefit of U.S. Provisional Patent Application No. 62/171,976, filed Jun. 5, 2015, and 62/221,836, filed Sep. 22, 2015, which applications are incorporated herein by reference in their entirety.

STATEMENT REGARDING FEDERALLY SPONSORED RESEARCH

This invention was made with government support under Grant No. GM098766 awarded by the National Institutes of Health. The government has certain rights in the invention.

INCORPORATION BY REFERENCE OF SEQUENCE LISTING PROVIDED AS A TEXT FILE

A Sequence Listing is provided herewith as a text file, "BERK-289WO_SeqList_ST25.txt" created on Jun. 2, 2016 and having a size of 7,639 KB. The contents of the text file are incorporated by reference herein in their entirety.

INTRODUCTION

RNA-mediated adaptive immune systems in bacteria and archaea rely on Clustered Regularly Interspaced Short Palindromic Repeat (CRISPR) genomic loci and CRISPR-associated (Cas) proteins that function together to provide protection from invading viruses and plasmids. In Type II CRISPR-Cas systems, the Cas9 protein functions as an RNA-guided endonuclease that uses a dual-guide RNA consisting of crRNA and trans-activating crRNA (tracrRNA) for target recognition and cleavage by a mechanism involving two nuclease active sites that together generate double-stranded DNA breaks (DSBs).

RNA-programmed Cas9 has proven to be a versatile tool for genome engineering in multiple cell types and organisms. Guided by a dual-RNA complex or a chimeric single-guide RNA, Cas9 (or variants of Cas9 such as nickase variants, catalytically inactive variants, etc.) can generate site-specific DSBs or single-stranded breaks (SSBs) within target nucleic acids, or can bind specifically to a specific region of a target nucleic acid. Target nucleic acids can include double-stranded DNA (dsDNA) and single-stranded DNA (ssDNA) as well as RNA. When cleavage of a target nucleic acid occurs within a cell (e.g., a eukaryotic cell), the break in the target nucleic acid can be repaired by non-homologous end joining (NHEJ) or homology directed repair (HDR).

The Cas9 system provides a facile means of modifying genomic information and/or for binding to specific loci within a target nucleic acid (e.g., for labeling/imaging applications). In addition, catalytically inactive Cas9 alone or fused to domains from other proteins to modify target nucleic acids or proteins associated with target nucleic acids (e.g., transcriptional activator or repressor domains to alter transcription of target genes).

CRISPR-based technologies have emerged as powerful tools to alter genomes and mark chromosomal loci, but there is a need in the art for cost effective methods and compositions for generating sets (e.g., libraries) of guide RNAs that can target descrete loci within a given target nucleic acid (e.g., whole chromosome/genome Cas9 guide RNA libraries).

SUMMARY

The present disclosure provides methods, kits, and compositions for generating a library of DNA molecules encoding CRISPR/Cas guide RNAs. For example, the present disclosure provides compositions, kits, and methods for generating a library of DNA molecules encoding Cas9 single guide RNAs (sgRNAs) or Cas9 targeter RNAs.

The methods provided herein can include the step of cleaving a target DNA molecule (any target DNA molecule from any organism, e.g., a chromosome, a collection of chromosomes such as a eukaryotic genome, etc.) with one or more DNA endonucleases (PAM-recognition DNA endonucleases) that specifically bind to and cleave within a recognition sequence that includes a PAM sequence (e.g., a Cas9 PAM sequence), thereby generating a plurality of DNA cleavage fragments. A DNA adapter can be attached (e.g., ligated) to the DNA cleavage fragments and then contacted with a distal-cleaving DNA endonuclease (a DNA endonuclease that specifically binds to a recognition sequence present in the DNA adapter but cleaves at a site within the DNA cleavage fragment) to generate a library of CRISPR/Cas guide sequences (e.g., Cas9 guide sequences). After removal of all or a portion of the DNA adapter, a constant region of a CRISPR/Cas guide RNA (e.g., a constant region of a Cas9 targeter RNA or Cas9 sgRNA) can be attached to the library of guide sequences to generate a library of DNA molecules encoding CRISPR/Cas guide RNAs (e.g., a library of DNA molecules encoding Cas9 single guide RNAs (sgRNAs) or Cas9 targeter RNAs).

As an example, in some cases, a method of generating a library of DNA molecules encoding Cas9 single guide RNAs (sgRNAs) or Cas9 targeter RNAs includes: (a) contacting a target DNA molecule with a first DNA endonuclease that specifically binds to and cleaves within a recognition sequence that includes a Cas9 PAM sequence, to generate a plurality of cleavage fragments; (b) attaching a first DNA adapter to the plurality of cleavage fragments to generate a plurality of adapter-attached cleavage fragments, each having an adapter segment and a cleavage fragment segment; (c) contacting the plurality of adapter-attached cleavage fragments with a second DNA endonuclease that specifically binds to a recognition sequence present in the adapter segment and cleaves within the cleavage fragment segment to generate a plurality of adapter-attached Cas9 guide sequences each having an adapter segment and a guide sequence segment; (d) contacting the plurality of adapter-attached Cas9 guide sequences with a third DNA endonuclease that specifically binds to a recognition sequence present in the adapter segment and cleaves at one or more sites to remove all or a portion of the adapter segment, thereby generating a plurality of Cas9 guide sequences; and (e) attaching DNA encoding a constant region of a Cas9 sgRNA or a Cas9 targeter RNA to the plurality of Cas9 guide sequences to generate a library of DNA molecules encoding Cas9 sgRNAs or Cas9 targeter RNAs.

In some cases, the method includes a step of circularizing the plurality of adapter-attached Cas9 guide sequences. In some cases, the first DNA adapter includes the DNA encoding the constant region of a Cas9 sgRNA or a Cas9 targeter RNA. In some cases, said contacting of step (d) removes a portion of the adapter segment that is present between the Cas9 guide sequence and the DNA encoding the constant region of a Cas9 sgRNA or a Cas9 targeter RNA. In some cases, the third DNA endonuclease of step (d) cleaves at or near the junction of the adapter segment and the guide sequence segment, and removes all or most of the adapter segment from the plurality of adapter-attached Cas9 guide sequences In some cases, step (e) includes attaching a DNA Linker to the plurality of Cas9 guide sequences, wherein the DNA Linker encodes the constant region of the Cas9 sgRNA or the Cas9 targeter RNA. In some cases, step (e) includes inserting the plurality of Cas9 guide sequences into a vector that encodes the constant region of the Cas9 sgRNA or the Cas9 targeter RNA.

In some cases, the first DNA adapter includes two recognition sequences that can be specifically bound by the second DNA endonuclease, wherein the two recognition sequences are positioned at opposite ends of the first DNA adapter such that the second DNA endonuclease will cleave within the cleavage fragment segment regardless of the orientation at which the first DNA adapter is attached to each cleavage fragment of the plurality of cleavage fragments. In some cases, the first DNA endonuclease is selected from: BfaI, HpaII, ScrFI, MspI, BstNI, NciI, BsiSI, HapII, MaeI, XspI, AsuC2I, BcnI, BpuMI, CauII, BciT130I, BptI, BseBI, BsiLI, Bst2UI, BstOI, MvaI, Bme1390I, BmrFI, and MspR9I. In some cases, step (a) includes contacting the DNA molecule with two or more PAM-recognition DNA endonucleases that each specifically binds to and cleaves within a recognition sequence that includes a Cas9 PAM sequence. In some cases, step (a) includes contacting the DNA molecule with three or more PAM-recognition DNA endonucleases that each specifically binds to and cleaves within a recognition sequence that includes a Cas9 PAM sequence. In some cases, the three or more PAM-recognition DNA endonucleases include BfaI, HpaII, and ScrFI. In some cases, the second DNA endonuclease cleaves at a distance of from 17 to 30 nucleotides from its recognition sequence. In some cases, the second DNA endonuclease cleaves at a site that is 17 to 30 nucleotides from the junction of the adapter segment and the cleavage fragment segment. In some cases, the second DNA endonuclease is a type II DNA endonuclease. In some cases, the second DNA endonuclease is selected from the group consisting of: ApyPI, AquII, AquIII, AquIV, CdpI, CstMI, DraRI, DrdIV, MaqI, MmeI, NhaXI, NlaCI, NmeAIII, PlaDI, PspOMII, PspPRI, RceI, RpaB5I, SdeAI, SpoDI, and BsbI. In some cases, the generated DNA molecules encoding Cas9 sgRNAs or Cas9 targeter RNAs each include a guide sequence that is in a range of from 17 nucleotides to 25 nucleotides in length. In some cases, the third DNA endonuclease cleaves at a distance of from 1 to 20 nucleotides from its recognition sequence. In some cases, the third DNA endonuclease is BsaXI.

In some cases, the method includes a step of blunting cleavage products that are produced by one or more of said steps (a), (c), and (d). In some cases, the method includes a step of blunting the plurality of cleavage fragments produced in step (a). In some cases, the blunting includes contacting the plurality of cleavage fragments generated in step (a) with a nuclease that removes single stranded overhang DNA. In some cases, the method includes a step of attaching a second DNA adapter to the plurality of adapter-attached Cas9 guide sequences generated in step (c), wherein the second DNA adapter comprises (i) an RNA polymerase promoter positioned such that it is operably linked to the Cas9 guide sequences once the second DNA adapter is attached, and/or (ii) an overhang or recognition sequence for cloning or circularization. In some cases, the method includes contacting the library of DNA molecules encoding Cas9 sgRNAs or Cas9 targeter RNAs with an RNA polymerase to generate a library of Cas9 sgRNAs or Cas9 targeter RNAs.

In some cases, a subject kit for generating a library of DNA molecules encoding guide RNAs (e.g., Cas9 single guide RNAs (sgRNAs), Cas9 targeter RNAs, etc.) includes (a) a first DNA adapter, two DNA oligonucleotides that hybridize to form said first DNA adapter, or a nucleic acid comprising said first DNA adapter, wherein the first DNA adapter includes: (i) a first recognition sequence for a first DNA endonuclease that cleaves at a cleavage site outside of the first recognition sequence, wherein the first recognition sequence is positioned within the first DNA adapter such that said first DNA endonuclease will specifically bind to the first recognition sequence and will cleave at a site within a target DNA sequence that is attached to the first DNA adapter; and (ii) a second recognition sequence for a second DNA endonuclease that cleaves at a cleavage site outside of the second recognition sequence, wherein the second recognition sequence is positioned within the first DNA adapter such that said second DNA endonuclease will cleave within or immediately adjacent to the first recognition sequence. In some cases, the first DNA adapter comprises a nucleotide sequence encoding a constant region of a Cas9 sgRNA or a Cas9 targeter RNA. In some cases, the kit includes a vector that includes the first DNA adapter.

In some cases, the kit includes at least one of: (i) a DNA linker, (ii) two DNA oligonucleotides that hybridize to form said DNA linker, and (iii) a nucleic acid comprising said DNA linker; wherein the DNA linker comprises a nucleotide sequence encoding a constant region of a Cas9 targeter RNA or a Cas9 sgRNA. In some cases, the kit includes a vector that includes the DNA linker. In some cases, the kit includes at least one of: (i) a second DNA adapter, (ii) two DNA oligonucleotides that hybridize to form said second DNA adapter, and (iii) a nucleic acid comprising said second DNA adapter; wherein the second DNA adapter comprises one or more of: (a) an RNA polymerase promoter, (b) a recognition sequence that facilitates cloning, and (c) an overhang. In some cases, the kit includes a vector that includes the second DNA adapter.

In some cases, the kit includes a nucleic acid that includes the first and second DNA adapters, wherein (i) the nucleic acid is linear and the first and second DNA adapters are positioned on opposite ends of the nucleic acid, or (ii) the nucleic acid is circular and the first and second DNA adapters are positioned adjacent to one another such that cleavage between the first and second DNA adapters will produce a linear nucleic acid in which the first and second DNA adapters are positioned on opposite ends. In some cases, the nucleic acid that includes the first and second DNA adapters is a vector. In some cases, the vector is a viral vector or a plasmid vector.

In some cases, a subject kit includes a blunting nuclease that removes single stranded DNA overhangs. In some cases, the blunting nuclease is mung bean nuclease.

In some cases, the first and/or second DNA adapter includes a recognition sequence that can be specifically bound and cleaved by a PAM-recognition DNA endonuclease. In some cases, the first recognition sequence is a recognition sequence for one or more DNA endonucleases selected from the group consisting of: MmeI, NmeAIII, and BsbI. In some cases, the first recognition sequence is a recognition sequence for MmeI. In some cases, the second recognition sequence is a recognition sequence for BsaXI.

In some cases, a subject kit includes one or both of: (i) the first DNA endonuclease, and (ii) the second DNA endonuclease. In some cases, the first DNA endonuclease cleaves at a cleavage site that is 17 to 30 nucleotides from the first recognition sequence. In some cases, the first DNA endonuclease is selected from the group consisting of: MmeI, NmeAIII, and BsbI. In some cases, the first DNA endonuclease is MmeI. In some cases, the second DNA endonuclease cleaves at a cleavage site that is 1 to 20 nucleotides from the second recognition sequence. In some cases, the second DNA endonuclease is BsaXI.

In some cases, a subject kit includes one or more PAM-recognition DNA endonucleases that each specifically binds to and cleaves within a recognition sequence that includes a Cas9 PAM sequence. In some cases, a subject kit includes two or more PAM-recognition DNA endonucleases that each specifically binds to and cleaves within a recognition sequence that includes a Cas9 PAM sequence. In some cases, a subject kit includes three or more PAM-recognition DNA endonucleases that each specifically binds to and cleaves within a recognition sequence that includes a Cas9 PAM sequence. In some cases, a kit includes the PAM-recognition DNA endonucleases BfaI, HpaII, and ScrFI. In some cases, the PAM-recognition DNA endonucleases are selected from the group consisting of: BfaI, HpaII, ScrFI, MspI, BstNI, NciI, BsiSI, HapII, MaeI, XspI, AsuC2I, BcnI, BpuMI, CauII, BciT130I, BptI, BseBI, BsiLI, Bst2UI, BstOI, MvaI, Bme1390I, BmrFI, and MspR9I.

BRIEF DESCRIPTION OF THE DRAWINGS

FIG. 1A-1E present data related to showing that repetitive genomic loci can be visualized using dCas9-Neon in *Xenopus* egg extracts.

FIG. 4A-4F present data related to the generation of a library of DNA molecules encoding Cas9 guide RNAs for targeting sequences within the *E. coli* genome.

FIG. 8A-8B present schematic examples of compositions and methods provided herein.

FIG. 9A-9B present the DNA adapters of the protocols presented that correspond to FIG. 8A and FIG. 8B.

FIG. 10 present the recognition sequences for MmeI and BsaXI.

DEFINITIONS

Figure 1A:
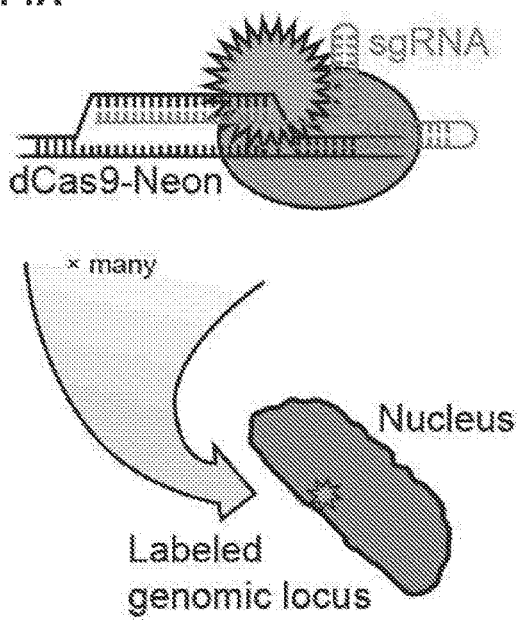

The terms "polynucleotide" and "nucleic acid," used interchangeably herein, refer to a polymeric form of nucleotides of any length, either ribonucleotides or deoxynucleotides. Thus, this term includes, but is not limited to, single-, double-, or multi-stranded DNA or RNA, genomic DNA, cDNA, DNA-RNA hybrids, or a polymer comprising purine and pyrimidine bases or other natural, chemically or biochemically modified, non-natural, or derivatized nucleotide bases. The terms "polynucleotide" and "nucleic acid" should be understood to include, as applicable to the embodiment being described, single-stranded (such as sense or antisense) and double-stranded polynucleotides.

The terms "peptide," "polypeptide," and "protein" are used interchangeably herein, and refer to a polymeric form of amino acids of any length, which can include coded and non-coded amino acids, chemically or biochemically modified or derivatized amino acids, and polypeptides having modified peptide backbones.

The term "naturally-occurring" as used herein as applied to a nucleic acid, a protein, a cell, or an organism, refers to a nucleic acid, protein, cell, or organism that is found in nature. For example, a polypeptide or polynucleotide sequence that is present in an organism (including viruses) that can be isolated from a source in nature and which has not been intentionally modified by a human in the laboratory is naturally occurring.

By "cleavage domain" or "active domain" or "nuclease domain" of a nuclease it is meant the polypeptide sequence or domain within the nuclease which possesses the catalytic activity for nucleic acid cleavage. A cleavage domain can be contained in a single polypeptide chain or cleavage activity can result from the association of two (or more) polypeptides. A single nuclease domain may consist of more than one isolated stretch of amino acids within a given polypeptide (e.g., RuvCI, RuvCII, and RuvCIII of a Cas9 protein).

As used herein the term "isolated" is meant to describe a polynucleotide, a polypeptide, or a cell that is in an environment different from that in which the polynucleotide, the polypeptide, or the cell naturally occurs. An isolated genetically modified host cell may be present in a mixed population of genetically modified host cells.

"Heterologous," as used herein, means a nucleotide or polypeptide sequence that is not found in the native nucleic acid or protein, respectively. For example, a variant Cas9 protein can be a chimeric variant Cas9 protein that includes a heterologous amino acid sequence (e.g., a fusion partner). Thus, a subject variant Cas9 protein can be a chimeric variant Cas9 protein that includes: (i) a variant Cas9 protein (e.g., in some cases having a disrupted RuvC and/or HNH domain) and (ii) a non-Cas9 polypeptide (where the non-Cas9 polypeptide can be referred to as a fusion partner). For example, a variant Cas9 protein can be a chimeric Cas9 protein that includes a variant Cas9 protein fused to a non-Cas9 polypeptide (where the non-Cas9 polypeptide can be referred to as a fusion partner). In some cases, a variant Cas9 protein can be a chimeric variant Cas9 protein that includes (a) a variant Cas9 protein fused to (b) a portion of a another Cas9 protein (e.g., a domain or region of a Cas9 protein that is different from the Cas9 protein of portion (a), e.g., the Cas9 protein of portion (a) can be from a different species than the Cas9 protein of portion (b)).

As used herein, the term "exogenous nucleic acid" refers to a nucleic acid that is not normally or naturally found in and/or produced by a given bacterium, organism, or cell in nature. As used herein, the term "endogenous nucleic acid" refers to a nucleic acid that is normally found in and/or produced by a given bacterium, organism, or cell in nature. An "endogenous nucleic acid" is also referred to as a "native nucleic acid" or a nucleic acid that is "native" to a given bacterium, organism, or cell.

"Recombinant," as used herein, means that a particular nucleic acid (DNA or RNA) or protein is the product of various combinations of cloning, restriction, and/or ligation steps resulting in a construct having a structural coding or non-coding sequence distinguishable from endogenous nucleic acids found in natural systems. Generally, DNA sequences encoding the structural coding sequence can be assembled from cDNA fragments and short oligonucleotide linkers, or from a series of synthetic oligonucleotides, to provide a synthetic nucleic acid which is capable of being expressed from a recombinant transcriptional unit contained in a cell or in a cell-free transcription and translation system. Such sequences can be provided in the form of an open reading frame uninterrupted by internal non-translated sequences, or introns, which are typically present in eukaryotic genes. Genomic DNA comprising the relevant sequences can also be used in the formation of a recombinant gene or transcriptional unit. Sequences of non-translated DNA may be present 5' or 3' from the open reading frame, where such sequences do not interfere with manipulation or expression of the coding regions, and may indeed act to modulate production of a desired product by various mechanisms (see "DNA regulatory sequences", below).

Thus, e.g., the term "recombinant" polynucleotide or "recombinant" nucleic acid refers to one which is not naturally occurring, e.g., is made by the artificial combination of two otherwise separated segments of sequence through human intervention. This artificial combination is often accomplished by either chemical synthesis means, or by the artificial manipulation of isolated segments of nucleic acids, e.g., by genetic engineering techniques. Such is usually done to replace a codon with a redundant codon encoding the same or a conservative amino acid, while typically introducing or removing a sequence recognition site. Alternatively, it is performed to join together nucleic acid segments of desired functions to generate a desired combination of functions. This artificial combination is often accomplished by either chemical synthesis means, or by the artificial manipulation of isolated segments of nucleic acids, e.g., by genetic engineering techniques.

Similarly, the term "recombinant" polypeptide refers to a polypeptide which is not naturally occurring, e.g., is made by the artificial combination of two otherwise separated segments of amino sequence through human intervention. Thus, e.g., a polypeptide that comprises a heterologous amino acid sequence is recombinant.

By "construct" or "vector" is meant a recombinant nucleic acid, generally recombinant DNA, which has been generated for the purpose of the expression and/or propagation of a nucleotide sequence(s) of interest, or is to be used in the construction of other recombinant nucleotide sequences.

The terms "DNA regulatory sequences," "control elements," and "regulatory elements," used interchangeably herein, refer to transcriptional and translational control sequences, such as promoters, enhancers, polyadenylation signals, terminators, protein degradation signals, and the like, that provide for and/or regulate expression of a coding sequence and/or production of an encoded polypeptide in a host cell. As used herein, a "promoter sequence" or "promoter" is a DNA regulatory region capable of binding/recruiting RNA polymerase (e.g., via a transcription initiation complex) and initiating transcription of a downstream (3' direction) sequence (e.g., a protein coding ("coding") or non protein-coding ("non-coding") sequence. A promoter can be any convenient promoter (e.g., a T7 promoter). In some cases, a promoter is a constitutively active promoter (e.g., a promoter that is constitutively in an active/"ON" state), it may be an inducible promoter (e.g., a promoter whose state, active/"ON" or inactive/"OFF", is controlled by an external stimulus, e.g., the presence of a particular temperature, compound, or protein), it may be a spatially restricted promoter (e.g., tissue specific promoter, cell type specific promoter, etc.), and/or it may be a temporally restricted promoter (e.g., the promoter is in the "ON" state or "OFF" state during specific stages of embryonic development or during specific stages of a biological process, e.g., hair follicle cycle in mice).

"Operably linked" refers to a juxtaposition wherein the components so described are in a relationship permitting them to function in their intended manner. For instance, a promoter is operably linked to a nucleotide sequence (e.g., a protein coding sequence, e.g., a sequence encoding an mRNA; a non protein coding sequence, e.g., a sequence encoding a non-coding RNA (ncRNA) such as a Cas9 guide RNA, a targeter RNA, an activator RNA; and the like) if the promoter affects its transcription and/or expression. The relationship can also be referred to in the reverse and retain the same meaning. For example, a nucleotide sequence of interest can be said to be operably linked to a promoter. As used herein, the terms "heterologous promoter" and "heterologous control regions" refer to promoters and other control regions that are not normally associated with a particular nucleic acid in nature. For example, a "transcriptional control region heterologous to a coding region" is a transcriptional control region that is not normally associated with the coding region in nature.

A "host cell," as used herein, denotes an in vivo or in vitro eukaryotic cell, a prokaryotic cell, or a cell from a multicellular organism (e.g., a cell line) cultured as a unicellular entity, which eukaryotic or prokaryotic cells can be, or have been, used as recipients for a nucleic acid (e.g., an expression vector that comprises a nucleotide sequence of interest), and include the progeny of the original cell which has been genetically modified by the nucleic acid. It is understood that the progeny of a single cell may not necessarily be completely identical in morphology or in genomic or total DNA complement as the original parent, due to natural, accidental, or deliberate mutation. A "recombinant host cell" (also referred to as a "genetically modified host cell") is a host cell into which has been introduced a heterologous nucleic acid, e.g., an expression vector. For example, a subject prokaryotic host cell is a genetically modified prokaryotic host cell (e.g., a bacterium), by virtue of introduction into a suitable prokaryotic host cell of a heterologous nucleic acid, e.g., an exogenous nucleic acid that is foreign to (not normally found in nature in) the prokaryotic host cell, or a recombinant nucleic acid that is not normally found in the prokaryotic host cell; and a subject eukaryotic host cell is a genetically modified eukaryotic host cell, by virtue of introduction into a suitable eukaryotic host cell of a heterologous nucleic acid, e.g., an exogenous nucleic acid that is foreign to the eukaryotic host cell, or a recombinant nucleic acid that is not normally found in the eukaryotic host cell.

The term "conservative amino acid substitution" refers to the interchangeability in proteins of amino acid residues having similar side chains. For example, a group of amino acids having aliphatic side chains consists of glycine, alanine, valine, leucine, and isoleucine; a group of amino acids having aliphatic-hydroxyl side chains consists of serine and threonine; a group of amino acids having amide-containing side chains consists of asparagine and glutamine; a group of amino acids having aromatic side chains consists of phenylalanine, tyrosine, and tryptophan; a group of amino acids having basic side chains consists of lysine, arginine, and histidine; and a group of amino acids having sulfur-containing side chains consists of cysteine and methionine. Exemplary conservative amino acid substitution groups are: valine-leucine-isoleucine, phenylalanine-tyrosine, lysine-arginine, alanine-valine, and asparagine-glutamine.

A polynucleotide or polypeptide has a certain percent "sequence identity" to another polynucleotide or polypeptide, meaning that, when aligned, that percentage of bases or amino acids are the same, and in the same relative position, when comparing the two sequences. Sequence similarity can be determined in a number of different manners. To determine sequence identity, sequences can be aligned using the methods and computer programs, including BLAST, available over the world wide web at ncbi.nlm.nih.gov/BLAST. See, e.g., Altschul et al. (1990), *J. Mol. Biol.* 215:403-10. Another alignment algorithm is FASTA, available in the Genetics Computing Group (GCG) package, from Madison, Wis., USA, a wholly owned subsidiary of Oxford Molecular Group, Inc. Other techniques for alignment are described in Methods in Enzymology, vol. 266: Computer Methods for Macromolecular Sequence Analysis (1996), ed. Doolittle, Academic Press, Inc., a division of Harcourt Brace & Co., San Diego, Calif., USA. Of particular interest are alignment programs that permit gaps in the sequence. The Smith-Waterman is one type of algorithm that permits gaps in sequence alignments. See *Meth. Mol. Biol.* 70: 173-187 (1997). Also, the GAP program using the Needleman and Wunsch alignment method can be utilized to align sequences. See *J. Mol. Biol.* 48: 443-453 (1970).

"Binding" as used herein (e.g. with reference to binding between an RNA and a protein, e.g., via an RNA-binding domain of a polypeptide) refers to a non-covalent interaction between macromolecules (e.g., between a protein and a nucleic acid). While in a state of non-covalent interaction, the macromolecules are said to be "associated" or "interacting" or "binding" (e.g., when a molecule X is said to interact with a molecule Y, it is meant the molecule X binds to molecule Y in a non-covalent manner). Not all components of a binding interaction need be sequence-specific (e.g., contacts with phosphate residues in a DNA backbone), but some portions of a binding interaction may be sequence-specific. Binding interactions are generally characterized by a dissociation constant (Kd) of less than $10^{-6}$ M, less than $10^{-7}$ M, less than $10^{-8}$ M, less than $10^{-9}$ M, less than $10^{-10}$ M, less than $10^{-11}$ M, less than $10^{-12}$ M, less than $10^{-13}$ M, less than $10^{-14}$ M, or less than $10^{-15}$ M. "Affinity" refers to the strength of binding, increased binding affinity being correlated with a lower Kd.

By "binding domain" it is meant a protein domain that is able to bind non-covalently to another molecule. A binding domain can bind to, for example, a DNA molecule (a DNA-binding protein), an RNA molecule (an RNA-binding protein) and/or a protein molecule (a protein-binding protein). In the case of a protein domain-binding protein, it can bind to itself (to form homodimers, homotrimers, etc.) and/or it can bind to one or more molecules of a different protein or proteins.

Before the present invention is further described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described. All publications mentioned herein are incorporated herein by reference to disclose and describe the methods and/or materials in connection with which the publications are cited.

It must be noted that as used herein and in the appended claims, the singular forms "a," "an," and "the" include plural referents unless the context clearly dictates otherwise. Thus, for example, reference to "a protein" includes a plurality of such proteins and reference to "the nucleic acid" includes reference to one or more nucleic acids and equivalents thereof known to those skilled in the art, and so forth. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub-combination. All combinations of the embodiments pertaining to the invention are specifically embraced by the present invention and are disclosed herein just as if each and every combination was individually and explicitly disclosed. In addition, all sub-combinations of the various embodiments and elements thereof are also specifically embraced by the present invention and are disclosed herein just as if each and every such sub-combination was individually and explicitly disclosed herein.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

DETAILED DESCRIPTION

The present disclosure provides methods, kits, and compositions for generating DNA molecules encoding CRISPR/Cas guide RNAs (e.g., Cas9 single guide RNAs or Cas9 targeter RNAs). A library of such DNA molecules can be generated from any DNA source. The methods include a step of contacting target DNA with one or more DNA endonucleases that specifically bind to and cleave within a recognition sequence that includes a PAM sequence, to generate a plurality of cleavage fragments, to which a DNA adapter can be attached. A distal-cleaving DNA endonuclease can be used that specifically binds to a recognition sequence in the DNA adapter and cleaves at a site within the attached DNA cleavage fragments to generate a library of CRISPR/Cas guide sequences. After removal of all or a portion of the DNA adapter, a constant region of a guide RNA can be attached to generate DNA molecules encoding CRISPR/Cas guide RNAs.

Compositions and Methods

Cas9 Protein (Cas9)

A Cas9 guide RNA and a Cas9 protein form a complex. The guide RNA provides target specificity to the complex by having a nucleotide sequence that is complementary to a sequence (the target site) of a target nucleic acid (as noted above). The Cas9 protein of the complex provides the site-specific activity. In other words, the Cas9 protein is guided to a target site (e.g., stabilized at a target site) within a target nucleic acid sequence (e.g. a chromosomal sequence or an extrachromosomal sequence, e.g. an episomal sequence, a minicircle sequence, a mitochondrial sequence, a chloroplast sequence, etc.) by virtue of its association with the protein-binding segment of the Cas9 guide RNA.

A Cas9 protein can bind and/or modify (e.g., cleave, nick, methylate, demethylate, etc.) a target nucleic acid and/or a polypeptide associated with target nucleic acid (e.g., methylation or acetylation of a histone tail)(e.g., when the Cas9 protein includes a fusion partner with an activity). In some cases, the Cas9 protein is a naturally-occurring protein (e.g, naturally occurs in bacterial and/or archaeal cells). In other cases, the Cas9 protein is not a naturally-occurring polypeptide (e.g., the Cas9 protein is a variant Cas9 protein, a chimeric protein, and the like).

Examples of suitable Cas9 proteins include, but are not limited to, those set forth in SEQ ID NOs: 15-826. Naturally occurring Cas9 proteins bind a Cas9 guide RNA, are thereby directed to a specific sequence within a target nucleic acid (a target site), and cleave the target nucleic acid (e.g., cleave dsDNA to generate a double strand break, cleave ssDNA, cleave ssRNA, etc.). A chimeric Cas9 protein (a Cas9 fusion protein) is a fusion protein that is fused to a heterologous protein. The fusion partner can provide an activity, e.g., enzymatic activity (e.g., nuclease activity, activity for DNA and/or RNA methylation, activity for DNA and/or RNA cleavage, activity for histone acetylation, activity for histone methylation, activity for RNA modification, activity for RNA-binding, activity for RNA splicing etc.). In some cases a portion of the Cas9 protein (e.g., the RuvC domain and/or the HNH domain) exhibits reduced nuclease activity relative to the corresponding portion of a wild type Cas9 protein (e.g., in some cases the Cas9 protein is a nickase). In some cases, the Cas9 protein is enzymatically inactive.

Assays to determine whether given protein interacts with a Cas9 guide RNA can be any convenient binding assay that tests for binding between a protein and a nucleic acid. Suitable binding assays (e.g., gel shift assays) will be know to one of ordinary skill in the art (e.g., assays that include adding a Cas9 guide RNA and a protein to a target nucleic acid).

Assays to determine whether a protein has an activity (e.g., to determine if the protein has nuclease activity that cleaves a target nucleic acid and/or some heterologous activity) can be any convenient assay (e.g., any convenient nucleic acid cleavage assay that tests for nucleic acid cleavage). Suitable assays (e.g., cleavage assays) will be known to one of ordinary skill in the art and can include adding a Cas9 guide RNA and a protein to a target nucleic acid.

In some cases, a Cas9 protein (e.g., a chimeric Cas9 protein) has enzymatic activity that modifies target nucleic acid (e.g., nuclease activity, methyltransferase activity, demethylase activity, DNA repair activity, DNA damage activity, deamination activity, dismutase activity, alkylation activity, depurination activity, oxidation activity, pyrimidine dimer forming activity, integrase activity, transposase activity, recombinase activity, polymerase activity, ligase activity, helicase activity, photolyase activity or glycosylase activity).

In other cases, a Cas9 protein (e.g., a chimeric Cas9 protein) has enzymatic activity that modifies a polypeptide (e.g., a histone) associated with target nucleic acid (e.g., methyltransferase activity, demethylase activity, acetyltransferase activity, deacetylase activity, kinase activity, phosphatase activity, ubiquitin ligase activity, deubiquitinating activity, adenylation activity, deadenylation activity, SUMOylating activity, deSUMOylating activity, ribosylation activity, deribosylation activity, myristoylation activity or demyristoylation activity).

Many Cas9 orthologs from a wide variety of species have been identified and the proteins share only a few identical amino acids. Identified Cas9 orthologs have similar domain architecture with a central HNH endonuclease domain and a split RuvC/RNaseH domain (e.g., RuvCI, RuvCII, and RuvCIII). Cas9 proteins share 4 key motifs with a conserved architecture. Motifs 1, 2, and 4 are RuvC like motifs while motif 3 is an HNH-motif. In some cases, a suitable Cas9 protein comprises an amino acid sequence having 4 motifs, each of motifs 1-4 having 60% or more, 70% or more, 75% or more, 80% or more, 85% or more, 90% or more, 95% or more, 99% or more or 100% amino acid sequence identity to motifs 1-4 of the Cas9 amino acid sequence set forth as SEQ ID NO:22 (the motifs are in Table 4, below, and are set forth as SEQ ID NOs: 827-830, respectively), or to the corresponding portions in any of the amino acid sequences set forth in SEQ ID NOs:15-826.

In some cases, a suitable Cas9 protein comprises an amino acid sequence having 4 motifs, each of motifs 1-4 having 60% or more amino acid sequence identity to motifs 1-4 of the Cas9 amino acid sequence set forth as SEQ ID NO: 22 (the motifs are in Table 4, below, and are set forth as SEQ ID NOs: 827-830, respectively), or to the corresponding portions in any of the amino acid sequences set forth in SEQ ID NOs:15-826.

In some cases, a suitable Cas9 protein comprises an amino acid sequence having 4 motifs, each of motifs 1-4 having 70% or more amino acid sequence identity to motifs 1-4 of the Cas9 amino acid sequence set forth as SEQ ID NO: 22 (the motifs are in Table 4, below, and are set forth as SEQ ID NOs: 827-830, respectively), or to the corresponding portions in any of the amino acid sequences set forth in SEQ ID NOs:15-826.

In some cases, a suitable Cas9 protein comprises an amino acid sequence having 4 motifs, each of motifs 1-4 having 75% or more amino acid sequence identity to motifs 1-4 of the Cas9 amino acid sequence set forth as SEQ ID NO: 22 (the motifs are in Table 4, below, and are set forth as SEQ ID NOs: 827-830, respectively), or to the corresponding portions in any of the amino acid sequences set forth in SEQ ID NOs:15-826.

In some cases, a suitable Cas9 protein comprises an amino acid sequence having 4 motifs, each of motifs 1-4 having 80% or more amino acid sequence identity to motifs 1-4 of the Cas9 amino acid sequence set forth as SEQ ID NO: 22 (the motifs are in Table 4, below, and are set forth as SEQ ID NOs: 827-830, respectively), or to the corresponding portions in any of the amino acid sequences set forth in SEQ ID NOs:15-826.

In some cases, a suitable Cas9 protein comprises an amino acid sequence having 4 motifs, each of motifs 1-4 having 85% or more amino acid sequence identity to motifs 1-4 of the Cas9 amino acid sequence set forth as SEQ ID NO: 22 (the motifs are in Table 4, below, and are set forth as SEQ ID NOs: 827-830, respectively), or to the corresponding portions in any of the amino acid sequences set forth in SEQ ID NOs:15-826.

In some cases, a suitable Cas9 protein comprises an amino acid sequence having 4 motifs, each of motifs 1-4 having 90% or more amino acid sequence identity to motifs 1-4 of the Cas9 amino acid sequence set forth as SEQ ID NO: 22 (the motifs are in Table 4, below, and are set forth as SEQ ID NOs: 827-830, respectively), or to the corresponding portions in any of the amino acid sequences set forth in SEQ ID NOs:15-826.

In some cases, a suitable Cas9 protein comprises an amino acid sequence having 4 motifs, each of motifs 1-4 having 95% or more amino acid sequence identity to motifs 1-4 of the Cas9 amino acid sequence set forth as SEQ ID NO: 22 (the motifs are in Table 4, below, and are set forth as SEQ ID NOs: 827-830, respectively), or to the corresponding portions in any of the amino acid sequences set forth in SEQ ID NOs:15-826.

In some cases, a suitable Cas9 protein comprises an amino acid sequence having 4 motifs, each of motifs 1-4 having 99% or more amino acid sequence identity to motifs 1-4 of the Cas9 amino acid sequence set forth as SEQ ID NO: 22 (the motifs are in Table 4, below, and are set forth as SEQ ID NOs: 827-830, respectively), or to the corresponding portions in any of the amino acid sequences set forth in SEQ ID NOs:15-826.

In some cases, a suitable Cas9 protein comprises an amino acid sequence having 4 motifs, each of motifs 1-4 having 100% amino acid sequence identity to motifs 1-4 of the Cas9 amino acid sequence set forth as SEQ ID NO: 22 (the motifs are in Table 4, below, and are set forth as SEQ ID NOs: 827-830, respectively), or to the corresponding portions in any of the amino acid sequences set forth in SEQ ID NOs:15-826.

In some cases, a suitable Cas9 protein comprises an amino acid sequence having 60% or more, 70% or more, 75% or more, 80% or more, 85% or more, 90% or more, 95% or more, 99% or more or 100% amino acid sequence identity to amino acids 7-166 or 731-1003 of the Cas9 amino acid sequence set forth in SEQ ID NO: 22, or to the corresponding portions in any of the amino acid sequences set forth as SEQ ID NOs:15-826. Any Cas9 protein can be used as part of a chimeric Cas9 protein of the subject methods.

In some cases, a suitable Cas9 protein comprises an amino acid sequence having 60% or more amino acid sequence identity to amino acids 7-166 or 731-1003 of the Cas9 amino acid sequence set forth in SEQ ID NO: 22, or to the corresponding portions in any of the amino acid sequences set forth as SEQ ID NOs:15-826. Any Cas9 protein can be used as part of a chimeric Cas9 protein of the subject methods.

In some cases, a suitable Cas9 protein comprises an amino acid sequence having 70% or more amino acid sequence identity to amino acids 7-166 or 731-1003 of the Cas9 amino acid sequence set forth in SEQ ID NO: 22, or to the corresponding portions in any of the amino acid sequences set forth as SEQ ID NOs:15-826. Any Cas9 protein can be used as part of a chimeric Cas9 protein of the subject methods.

In some cases, a suitable Cas9 protein comprises an amino acid sequence having 75% or more amino acid sequence identity to amino acids 7-166 or 731-1003 of the Cas9 amino acid sequence set forth in SEQ ID NO: 22, or to the corresponding portions in any of the amino acid sequences set forth as SEQ ID NOs:15-826. Any Cas9 protein can be used as part of a chimeric Cas9 protein of the subject methods.

In some cases, a suitable Cas9 protein comprises an amino acid sequence having 80% or more amino acid sequence identity to amino acids 7-166 or 731-1003 of the Cas9 amino acid sequence set forth in SEQ ID NO: 22, or to the corresponding portions in any of the amino acid sequences set forth as SEQ ID NOs:15-826. Any Cas9 protein can be used as part of a chimeric Cas9 protein of the subject methods.

In some cases, a suitable Cas9 protein comprises an amino acid sequence having 85% or more amino acid sequence identity to amino acids 7-166 or 731-1003 of the Cas9 amino acid sequence set forth in SEQ ID NO: 22, or to the corresponding portions in any of the amino acid sequences set forth as SEQ ID NOs:15-826. Any Cas9 protein can be used as part of a chimeric Cas9 protein of the subject methods.

In some cases, a suitable Cas9 protein comprises an amino acid sequence having 90% or more amino acid sequence identity to amino acids 7-166 or 731-1003 of the Cas9 amino acid sequence set forth in SEQ ID NO: 22, or to the corresponding portions in any of the amino acid sequences set forth as SEQ ID NOs:15-826. Any Cas9 protein can be used as part of a chimeric Cas9 protein of the subject methods.

In some cases, a suitable Cas9 protein comprises an amino acid sequence having 95% or more amino acid sequence identity to amino acids 7-166 or 731-1003 of the Cas9 amino acid sequence set forth in SEQ ID NO: 22, or to the corresponding portions in any of the amino acid sequences set forth as SEQ ID NOs:15-826. Any Cas9 protein can be used as part of a chimeric Cas9 protein of the subject methods.

In some cases, a suitable Cas9 protein comprises an amino acid sequence having 99% or more amino acid sequence identity to amino acids 7-166 or 731-1003 of the Cas9 amino acid sequence set forth in SEQ ID NO: 22, or to the corresponding portions in any of the amino acid sequences set forth as SEQ ID NOs:15-826. Any Cas9 protein can be used as part of a chimeric Cas9 protein of the subject methods.

In some cases, a suitable Cas9 protein comprises an amino acid sequence having 100% amino acid sequence identity to amino acids 7-166 or 731-1003 of the Cas9 amino acid sequence set forth in SEQ ID NO: 22, or to the corresponding portions in any of the amino acid sequences set forth as SEQ ID NOs:15-826. Any Cas9 protein can be used as part of a chimeric Cas9 protein of the subject methods.

In some cases, a suitable Cas9 protein comprises an amino acid sequence having 60% or more, 70% or more, 75% or more, 80% or more, 85% or more, 90% or more, 95% or more, 99% or more or 100% amino acid sequence identity to the Cas9 amino acid sequence set forth in SEQ ID NO: 22, or to any of the amino acid sequences set forth as SEQ ID NOs:15-826. Any Cas9 protein can be used as part of a chimeric Cas9 protein of the subject methods.

In some cases, a suitable Cas9 protein comprises an amino acid sequence having 60% or more amino acid sequence identity to the Cas9 amino acid sequence set forth in SEQ ID NO: 22, or to any of the amino acid sequences set forth as SEQ ID NOs:15-826. Any Cas9 protein can be used as part of a chimeric Cas9 protein for use in a subject method.

In some cases, a suitable Cas9 protein comprises an amino acid sequence having 70% or more amino acid sequence identity to the Cas9 amino acid sequence set forth in SEQ ID NO: 22, or to any of the amino acid sequences set forth as SEQ ID NOs:15-826. Any Cas9 protein can be used as part of a chimeric Cas9 protein of the subject methods.

In some cases, a suitable Cas9 protein comprises an amino acid sequence having 75% or more amino acid sequence identity to the Cas9 amino acid sequence set forth in SEQ ID NO: 22, or to any of the amino acid sequences set forth as SEQ ID NOs:15-826. Any Cas9 protein can be used as part of a chimeric Cas9 protein of the subject methods.

In some cases, a suitable Cas9 protein comprises an amino acid sequence having 80% or more amino acid sequence identity to the Cas9 amino acid sequence set forth in SEQ ID NO: 22, or to any of the amino acid sequences set forth as SEQ ID NOs:15-826. Any Cas9 protein can be used as part of a chimeric Cas9 protein of the subject methods.

In some cases, a suitable Cas9 protein comprises an amino acid sequence having 85% or more amino acid sequence identity to the Cas9 amino acid sequence set forth in SEQ ID NO: 22, or to any of the amino acid sequences set forth as SEQ ID NOs:15-826. Any Cas9 protein can be used as part of a chimeric Cas9 protein of the subject methods.

In some cases, a suitable Cas9 protein comprises an amino acid sequence having 90% or more amino acid sequence identity to the Cas9 amino acid sequence set forth in SEQ ID NO: 22, or to any of the amino acid sequences set forth as SEQ ID NOs:15-826. Any Cas9 protein can be used as part of a chimeric Cas9 protein of the subject methods.

In some cases, a suitable Cas9 protein comprises an amino acid sequence having 95% or more amino acid sequence identity to the Cas9 amino acid sequence set forth in SEQ ID NO: 22, or to any of the amino acid sequences set forth as SEQ ID NOs:15-826. Any Cas9 protein can be used as part of a chimeric Cas9 protein of the subject methods.

In some cases, a suitable Cas9 protein comprises an amino acid sequence having 99% or more amino acid sequence identity to the Cas9 amino acid sequence set forth in SEQ ID NO: 22, or to any of the amino acid sequences set forth as SEQ ID NOs:15-826. Any Cas9 protein can be used as part of a chimeric Cas9 protein of the subject methods.

In some cases, a suitable Cas9 protein comprises an amino acid sequence having 100% amino acid sequence identity to the Cas9 amino acid sequence set forth in SEQ ID NO: 22, or to any of the amino acid sequences set forth as SEQ ID NOs:15-826. Any Cas9 protein can be used as part of a chimeric Cas9 protein of the subject methods.

In some cases, a Cas9 protein comprises 4 motifs (as listed in Table 4), at least one with (or each with) amino acid sequences having 75% or more, 80% or more, 85% or more, 90% or more, 95% or more, 99% or more or 100% amino acid sequence identity to each of the 4 motifs listed in Table 4 (SEQ ID NOs:827-830), or to the corresponding portions in any of the amino acid sequences set forth as SEQ ID NOs:15-826.

As used herein, the term "Cas9 protein" encompasses the term "variant Cas9 protein"; and the term "variant Cas9 protein" encompasses the term "chimeric Cas9 protein" (or "Cas9 fusion protein").

Variant Cas9 Proteins

A variant Cas9 protein has an amino acid sequence that is different by one amino acid (e.g., has a deletion, insertion, substitution, fusion) (i.e., different by at least one amino acid) when compared to the amino acid sequence of a wild type Cas9 protein. In some instances, the variant Cas9 protein has an amino acid change (e.g., deletion, insertion, or substitution) that reduces the nuclease activity of the Cas9 protein. For example, in some instances, the variant Cas9 protein has 50% or less, 40% or less, 30% or less, 20% or less, 10% or less, 5% or less, or 1% or less of the nuclease activity of the corresponding wild-type Cas9 protein. In some cases, the variant Cas9 protein has no substantial nuclease activity. When a Cas9 protein is a variant Cas9 protein that has no substantial nuclease activity, it can be referred to as "dCas9."

In some cases, a variant Cas9 protein can cleave the complementary strand of a target nucleic acid but has reduced ability to cleave the non-complementary strand of a target nucleic acid. For example, the variant Cas9 protein can have a mutation (amino acid substitution) that reduces the function of the RuvC domain. As a non-limiting example, in some embodiments, a variant Cas9 protein has a mutation at residue D10 (e.g., D10A, aspartate to alanine) of SEQ ID NO: 22 or of SEQ ID NO: 826 (or the corresponding position of any of the proteins set forth in SEQ ID NOs:15-826) and can therefore cleave the complementary strand of a double stranded target nucleic acid but has reduced ability to cleave the non-complementary strand of a double stranded target nucleic acid (thus resulting in a single strand break (SSB) instead of a double strand break (DSB) when the variant Cas9 protein cleaves a double stranded target nucleic acid) (see, for example, Jinek et al., Science. 2012 Aug. 17; 337(6096):816-21).

In some cases, a variant Cas9 protein can cleave the non-complementary strand of a target nucleic acid but has reduced ability to cleave the complementary strand of the target nucleic acid. For example, the variant Cas9 protein can have a mutation (amino acid substitution) that reduces the function of the HNH domain. Thus, the Cas9 protein can be a nickase that cleaves the non-complementary strand, but does not cleave the complementary strand (e.g., does not cleave a single stranded target nucleic acid). As a non-limiting example, in some embodiments, the variant Cas9 protein has a mutation at position H840 (e.g., an H840A mutation, histidine to alanine) of SEQ ID NO: 22 or at the corresponding position H839 (e.g., H839A) of SEQ ID NO: 826 (or the corresponding position of any of the proteins set forth as SEQ ID NOs:15-826) and can therefore cleave the non-complementary strand of the target nucleic acid but has reduced ability to cleave (e.g., does not cleave) the complementary strand of the target nucleic acid. Such a Cas9 protein has a reduced ability to cleave a target nucleic acid (e.g., a single stranded target nucleic acid).

In some cases, a variant Cas9 protein has a reduced ability to cleave both the complementary and the non-complementary strands of a double stranded target nucleic acid. As a non-limiting example, in some cases, the variant Cas9 protein harbors mutations at residues D10 and H840 (e.g., D10A and H840A) of SEQ ID NO: 22 or D10 and H839 of SEQ ID NO: 826 (or the corresponding residues of any of the proteins set forth as SEQ ID NOs:15-826) such that the polypeptide has a reduced ability to cleave (e.g., does not cleave) both the complementary and the non-complementary strands of a target nucleic acid. Such a Cas9 protein has a reduced ability to cleave a target nucleic acid (e.g., a single stranded or double stranded target nucleic acid) but retains the ability to bind a target nucleic acid.

In addition to the above, a variant Cas9 protein can have the same parameters for sequence identity as described above for Cas9 proteins. Thus, in some cases, a suitable variant Cas9 protein comprises an amino acid sequence having 4 motifs, each of motifs 1-4 having 60% or more, 70% or more, 75% or more, 80% or more, 85% or more, 90% or more, 95% or more, 99% or more or 100% amino acid sequence identity to motifs 1-4 of the Cas9 amino acid sequence set forth as SEQ ID NO: 22 (the motifs are in Table 4, below, and are set forth as SEQ ID NOs: 827-830, respectively), or to the corresponding portions in any of the amino acid sequences set forth in SEQ ID NOs:15-826.

In some cases, a suitable variant Cas9 protein comprises an amino acid sequence having 4 motifs, each of motifs 1-4 having 60% or more amino acid sequence identity to motifs 1-4 of the Cas9 amino acid sequence set forth as SEQ ID NO: 22 (the motifs are in Table 4, below, and are set forth as SEQ ID NOs: 827-830, respectively), or to the corresponding portions in any of the amino acid sequences set forth in SEQ ID NOs:15-826.

In some cases, a suitable variant Cas9 protein comprises an amino acid sequence having 4 motifs, each of motifs 1-4 having 70% or more amino acid sequence identity to motifs 1-4 of the Cas9 amino acid sequence set forth as SEQ ID NO: 22 (the motifs are in Table 4, below, and are set forth as SEQ ID NOs: 827-830, respectively), or to the corresponding portions in any of the amino acid sequences set forth in SEQ ID NOs:15-826.

In some cases, a suitable variant Cas9 protein comprises an amino acid sequence having 4 motifs, each of motifs 1-4 having 75% or more amino acid sequence identity to motifs 1-4 of the Cas9 amino acid sequence set forth as SEQ ID NO: 22 (the motifs are in Table 4, below, and are set forth as SEQ ID NOs: 827-830, respectively), or to the corresponding portions in any of the amino acid sequences set forth in SEQ ID NOs:15-826.

In some cases, a suitable variant Cas9 protein comprises an amino acid sequence having 4 motifs, each of motifs 1-4 having 80% or more amino acid sequence identity to motifs 1-4 of the Cas9 amino acid sequence set forth as SEQ ID NO: 22 (the motifs are in Table 4, below, and are set forth as SEQ ID NOs: 827-830, respectively), or to the corresponding portions in any of the amino acid sequences set forth in SEQ ID NOs:15-826.

In some cases, a suitable variant Cas9 protein comprises an amino acid sequence having 4 motifs, each of motifs 1-4 having 85% or more amino acid sequence identity to motifs 1-4 of the Cas9 amino acid sequence set forth as SEQ ID NO: 22 (the motifs are in Table 4, below, and are set forth as SEQ ID NOs: 827-830, respectively), or to the corresponding portions in any of the amino acid sequences set forth in SEQ ID NOs:15-826.

In some cases, a suitable variant Cas9 protein comprises an amino acid sequence having 4 motifs, each of motifs 1-4 having 90% or more amino acid sequence identity to motifs 1-4 of the Cas9 amino acid sequence set forth as SEQ ID NO: 22 (the motifs are in Table 4, below, and are set forth as SEQ ID NOs: 827-830, respectively), or to the corresponding portions in any of the amino acid sequences set forth in SEQ ID NOs:15-826.

In some cases, a suitable variant Cas9 protein comprises an amino acid sequence having 4 motifs, each of motifs 1-4 having 95% or more amino acid sequence identity to motifs 1-4 of the Cas9 amino acid sequence set forth as SEQ ID NO: 22 (the motifs are in Table 4, below, and are set forth as SEQ ID NOs: 827-830, respectively), or to the corresponding portions in any of the amino acid sequences set forth in SEQ ID NOs:15-826.

In some cases, a suitable variant Cas9 protein comprises an amino acid sequence having 4 motifs, each of motifs 1-4 having 99% or more amino acid sequence identity to motifs 1-4 of the Cas9 amino acid sequence set forth as SEQ ID NO: 22 (the motifs are in Table 4, below, and are set forth as SEQ ID NOs: 827-830, respectively), or to the corresponding portions in any of the amino acid sequences set forth in SEQ ID NOs:15-826.

In some cases, a suitable variant Cas9 protein comprises an amino acid sequence having 4 motifs, each of motifs 1-4 having 100% amino acid sequence identity to motifs 1-4 of the Cas9 amino acid sequence set forth as SEQ ID NO: 22 (the motifs are in Table 4, below, and are set forth as SEQ ID NOs: 827-830, respectively), or to the corresponding portions in any of the amino acid sequences set forth in SEQ ID NOs:15-826.

TABLE 4

Table 4 lists 4 motifs that are present in Cas9 sequences from various species

| Motif # | Motif | Amino acids (residue #s) | Highly conserved |
|---|---|---|---|
| 1 | RuvC-like I | IGLDIGTNSVGWAVI (7-21) (SEQ ID NO: 827) | D10, G12, G17 |
| 2 | RuvC-like II | IVIEMARE (759-766) (SEQ ID NO: 828) | E762 |
| 3 | HNH-motif | DVDHIVPQSFLKDDSIDNKVLTRS DKN (837-863) (SEQ ID NO: 829) | H840, N854, N863 |
| 4 | RuvC-like II | HHAHDAYL (982-989) (SEQ ID NO: 830) | H982, H983, A984, D986, A987 |

Amino acids listed in Table 4 are from the Cas9 from *S. pyogenes* (SEQ ID NO: 22).

In some cases, a suitable variant Cas9 protein comprises an amino acid sequence having 60% or more, 70% or more, 75% or more, 80% or more, 85% or more, 90% or more, 95% or more, 99% or more, or 100% amino acid sequence identity to amino acids 7-166 or 731-1003 of the Cas9 amino acid sequence set forth in SEQ ID NO: 22, or to the corresponding portions in any of the amino acid sequences set forth as SEQ ID NOs:15-826. Any Cas9 protein as defined above can be used as a variant Cas9 protein or as part of a chimeric variant Cas9 protein of the subject methods.

In some cases, a suitable variant Cas9 protein comprises an amino acid sequence having 60% or more amino acid sequence identity to amino acids 7-166 or 731-1003 of the Cas9 amino acid sequence set forth in SEQ ID NO: 22, or to the corresponding portions in any of the amino acid sequences set forth as SEQ ID NOs:15-826. Any Cas9 protein as defined above can be used as a variant Cas9 protein or as part of a chimeric variant Cas9 protein of the subject methods.

In some cases, a suitable variant Cas9 protein comprises an amino acid sequence having 70% or more amino acid sequence identity to amino acids 7-166 or 731-1003 of the Cas9 amino acid sequence set forth in SEQ ID NO: 22, or to the corresponding portions in any of the amino acid sequences set forth as SEQ ID NOs:15-826. Any Cas9 protein as defined above can be used as a variant Cas9 protein or as part of a chimeric variant Cas9 protein of the subject methods.

In some cases, a suitable variant Cas9 protein comprises an amino acid sequence having 75% or more amino acid sequence identity to amino acids 7-166 or 731-1003 of the Cas9 amino acid sequence set forth in SEQ ID NO: 22, or to the corresponding portions in any of the amino acid sequences set forth as SEQ ID NOs:15-826. Any Cas9 protein as defined above can be used as a variant Cas9 protein or as part of a chimeric variant Cas9 protein of the subject methods.

In some cases, a suitable variant Cas9 protein comprises an amino acid sequence having 80% or more amino acid sequence identity to amino acids 7-166 or 731-1003 of the Cas9 amino acid sequence set forth in SEQ ID NO: 22, or to the corresponding portions in any of the amino acid sequences set forth as SEQ ID NOs:15-826. Any Cas9 protein as defined above can be used as a variant Cas9 protein or as part of a chimeric variant Cas9 protein of the subject methods.

In some cases, a suitable variant Cas9 protein comprises an amino acid sequence having 85% or more amino acid sequence identity to amino acids 7-166 or 731-1003 of the Cas9 amino acid sequence set forth in SEQ ID NO: 22, or to the corresponding portions in any of the amino acid sequences set forth as SEQ ID NOs:15-826. Any Cas9 protein as defined above can be used as a variant Cas9 protein or as part of a chimeric variant Cas9 protein of the subject methods.

In some cases, a suitable variant Cas9 protein comprises an amino acid sequence having 90% or more amino acid sequence identity to amino acids 7-166 or 731-1003 of the Cas9 amino acid sequence set forth in SEQ ID NO: 22, or to the corresponding portions in any of the amino acid sequences set forth as SEQ ID NOs:15-826. Any Cas9 protein as defined above can be used as a variant Cas9 protein or as part of a chimeric variant Cas9 protein of the subject methods.

In some cases, a suitable variant Cas9 protein comprises an amino acid sequence having 95% or more amino acid sequence identity to amino acids 7-166 or 731-1003 of the Cas9 amino acid sequence set forth in SEQ ID NO: 22, or to the corresponding portions in any of the amino acid sequences set forth as SEQ ID NOs:15-826. Any Cas9 protein as defined above can be used as a variant Cas9 protein or as part of a chimeric variant Cas9 protein of the subject methods.

In some cases, a suitable variant Cas9 protein comprises an amino acid sequence having 99% or more amino acid sequence identity to amino acids 7-166 or 731-1003 of the Cas9 amino acid sequence set forth in SEQ ID NO: 22, or to the corresponding portions in any of the amino acid sequences set forth as SEQ ID NOs:15-826. Any Cas9 protein as defined above can be used as a variant Cas9 protein or as part of a chimeric variant Cas9 protein of the subject methods.

In some cases, a suitable variant Cas9 protein comprises an amino acid sequence having 100% amino acid sequence identity to amino acids 7-166 or 731-1003 of the Cas9 amino acid sequence set forth in SEQ ID NO: 22, or to the corresponding portions in any of the amino acid sequences set forth as SEQ ID NOs:15-826. Any Cas9 protein as defined above can be used as a variant Cas9 protein or as part of a chimeric variant Cas9 protein of the subject methods.

In some cases, a suitable variant Cas9 protein comprises an amino acid sequence having 60% or more, 70% or more, 75% or more, 80% or more, 85% or more, 90% or more, 95% or more, 99% or more, or 100% amino acid sequence identity to the Cas9 amino acid sequence set forth in SEQ ID NO: 22, or to any of the amino acid sequences set forth as SEQ ID NOs:15-826. Any Cas9 protein as defined above can be used as a variant Cas9 protein or as part of a chimeric variant Cas9 protein of the subject methods.

In some cases, a suitable variant Cas9 protein comprises an amino acid sequence having 60% or more amino acid sequence identity to the Cas9 amino acid sequence set forth in SEQ ID NO: 22, or to any of the amino acid sequences set forth as SEQ ID NOs:15-826. Any Cas9 protein as defined above can be used as a variant Cas9 protein or as part of a chimeric variant Cas9 protein of the subject methods.

In some cases, a suitable variant Cas9 protein comprises an amino acid sequence having 70% or more amino acid sequence identity to the Cas9 amino acid sequence set forth in SEQ ID NO: 22, or to any of the amino acid sequences set forth as SEQ ID NOs:15-826. Any Cas9 protein as defined above can be used as a variant Cas9 protein or as part of a chimeric variant Cas9 protein of the subject methods.

In some cases, a suitable variant Cas9 protein comprises an amino acid sequence having 75% or more amino acid sequence identity to the Cas9 amino acid sequence set forth in SEQ ID NO: 22, or to any of the amino acid sequences set forth as SEQ ID NOs:15-826. Any Cas9 protein as defined above can be used as a variant Cas9 protein or as part of a chimeric variant Cas9 protein of the subject methods.

In some cases, a suitable variant Cas9 protein comprises an amino acid sequence having 80% or more amino acid sequence identity to the Cas9 amino acid sequence set forth in SEQ ID NO: 22, or to any of the amino acid sequences set forth as SEQ ID NOs:15-826. Any Cas9 protein as defined above can be used as a variant Cas9 protein or as part of a chimeric variant Cas9 protein of the subject methods.

In some cases, a suitable variant Cas9 protein comprises an amino acid sequence having 85% or more amino acid sequence identity to the Cas9 amino acid sequence set forth in SEQ ID NO: 22, or to any of the amino acid sequences set forth as SEQ ID NOs:15-826. Any Cas9 protein as defined above can be used as a variant Cas9 protein or as part of a chimeric variant Cas9 protein of the subject methods.

In some cases, a suitable variant Cas9 protein comprises an amino acid sequence having 90% or more amino acid sequence identity to the Cas9 amino acid sequence set forth in SEQ ID NO: 22, or to any of the amino acid sequences set forth as SEQ ID NOs:15-826. Any Cas9 protein as defined above can be used as a variant Cas9 protein or as part of a chimeric variant Cas9 protein of the subject methods.

In some cases, a suitable variant Cas9 protein comprises an amino acid sequence having 95% or more amino acid sequence identity to the Cas9 amino acid sequence set forth in SEQ ID NO: 22, or to any of the amino acid sequences set forth as SEQ ID NOs:15-826. Any Cas9 protein as defined above can be used as a variant Cas9 protein or as part of a chimeric variant Cas9 protein of the subject methods.

In some cases, a suitable variant Cas9 protein comprises an amino acid sequence having 99% or more amino acid sequence identity to the Cas9 amino acid sequence set forth in SEQ ID NO: 22, or to any of the amino acid sequences set forth as SEQ ID NOs:15-826. Any Cas9 protein as defined above can be used as a variant Cas9 protein or as part of a chimeric variant Cas9 protein of the subject methods.

In some cases, a suitable variant Cas9 protein comprises an amino acid sequence having 100% amino acid sequence identity to the Cas9 amino acid sequence set forth in SEQ ID NO: 22, or to any of the amino acid sequences set forth as SEQ ID NOs:15-826. Any Cas9 protein as defined above can be used as a variant Cas9 protein or as part of a chimeric variant Cas9 protein of the subject methods.

As noted above, in some cases, the Cas9 protein is a chimeric Cas9 protein and is fused to a fusion partner. In some cases, the Cas9 portion of the chimeric Cas9 protein has one or more amino acid mutations that render the Cas9 portion to be a nickase or a dCas9 (e.g., as described above). The fusion partner can included any amino acid sequence that provide a desired property to the chimeric Cas9 protein. Thus, in some embodiments, a subject Cas9 protein is a variant Cas9 protein that is a chimeric Cas9 protein (also referred to herein as a fusion protein, e.g., a "Cas9 fusion protein"). A Cas9 fusion protein can bind and/or modify a target nucleic acid (e.g., cleave, methylate, demethylate, etc.). In some cases, a Cas9 fusion protein can modify a polypeptide associated with target nucleic acid (e.g., methylation, acetylation, etc., of, for example, a histone tail). For purposes of this disclosure, a "Cas9 fusion protein" is a subject variant Cas9 protein that is fused to a covalently linked heterologous polypeptide (also referred to as a "fusion partner"). In some cases, the heterologous protein exhibits (and therefore provides for) an activity (e.g., an enzymatic activity) that will also be exhibited by the Cas9 fusion protein (e.g., methyltransferase activity, acetyltransferase activity, kinase activity, ubiquitinating activity, etc.). When describing fusion partners, it is to be understood that fusion to the Cas9 protein can include fusion of an entire protein (an entire fusion partner protein) (e.g., an entire transcription activator or repressor protein); or can include fusion of a particular region and/or domain of the fusion partner to the Cas9 protein (e.g., fusion of a transcription activator or repressor domain from a fusion partner).

In some cases, the heterologous sequence provides for subcellular localization, i.e., the heterologous sequence is a subcellular localization sequence (e.g., a nuclear localization signal (NLS) for targeting to the nucleus, a sequence to keep the fusion protein out of the nucleus, e.g., a nuclear export sequence (NES), a sequence to keep the fusion protein retained in the cytoplasm, a mitochondrial localization signal for targeting to the mitochondria, a chloroplast localization signal for targeting to a chloroplast, an ER retention signal, and the like). In some embodiments, a Cas9 protein does not include a NLS so that the protein is not targeted to the nucleus (which can be advantageous, e.g., when the target nucleic acid is an RNA that is present in the cytosol). In some embodiments, the heterologous sequence can provide a tag (i.e., the heterologous sequence is a detectable label) for ease of tracking and/or purification (e.g., a fluorescent protein, e.g., green fluorescent protein (GFP), YFP, RFP, CFP, mCherry, tdTomato, and the like; a histidine tag, e.g., a 6×His tag; a hemagglutinin (HA) tag; a FLAG tag; a Myc tag; and the like). In some embodiments, the heterologous sequence can provide for increased or decreased stability (i.e., the heterologous sequence is a stability control peptide, e.g., a degron, which in some cases is controllable (e.g., a temperature sensitive or drug controllable degron sequence, see below). In some embodiments, the heterologous sequence can provide for increased or decreased transcription from the target nucleic acid (i.e., the heterologous sequence is a transcription modulation sequence, e.g., a transcription factor/activator or a fragment thereof, a protein or fragment thereof that recruits a transcription factor/activator, a transcription repressor or a fragment thereof, a protein or fragment thereof that recruits a transcription repressor, a small molecule/drug-responsive transcription regulator, etc.). In some embodiments, the heterologous sequence can provide a binding domain (i.e., the heterologous sequence is a protein binding sequence, e.g., to provide the ability of a subject Cas9 fusion protein to bind to another protein of interest, e.g., a DNA or histone modifying protein, a transcription factor or transcription repressor, a recruiting protein, an RNA modification enzyme, an RNA-binding protein, a translation initiation factor, an RNA splicing factor, etc.). A heterologous nucleic acid sequence may be linked to another nucleic acid sequence (e.g., by genetic engineering) to generate a chimeric nucleotide sequence encoding a chimeric polypeptide.

A subject Cas9 fusion polypeptide (Cas9 fusion protein) can have multiple (1 or more, 2 or more, 3 or more, 4 or more, 5 or more, 6 or more, etc.) fusion partners in any combination of the above. As an illustrative example, a Cas9 fusion protein can have a heterologous sequence that provides an activity (e.g., for transcription modulation, target modification, modification of a protein associated with a target nucleic acid, etc.) and can also have a subcellular localization sequence (e.g., 1 or more NLSs). In some cases, such a Cas9 fusion protein might also have a tag for ease of tracking and/or purification (e.g., green fluorescent protein (GFP), YFP, RFP, CFP, mCherry, tdTomato, and the like; a histidine tag, e.g., a 6×His tag; a hemagglutinin (HA) tag; a FLAG tag; a Myc tag; and the like). As another illustrative example, a Cas9 protein can have one or more NLSs (e.g., two or more, three or more, four or more, five or more, 1, 2, 3, 4, or 5 NLSs). In some cases a fusion partner (or multiple fusion partners) (e.g., an NLS, a tag, a fusion partner providing an activity, etc.) is located at or near the C-terminus of Cas9. In some cases a fusion partner (or multiple fusion partners) (e.g., an NLS, a tag, a fusion partner providing an activity, etc.) is located at the N-terminus of Cas9. In some cases a Cas9 has a fusion partner (or multiple fusion partners)(e.g., an NLS, a tag, a fusion partner providing an activity, etc.) at both the N-terminus and C-terminus.

Suitable fusion partners that provide for increased or decreased stability include, but are not limited to degron sequences. Degrons are readily understood by one of ordinary skill in the art to be amino acid sequences that control the stability of the protein of which they are part. For example, the stability of a protein comprising a degron sequence is controlled in part by the degron sequence. In some cases, a suitable degron is constitutive such that the degron exerts its influence on protein stability independent of experimental control (i.e., the degron is not drug inducible, temperature inducible, etc.) In some cases, the degron provides the variant Cas9 protein with controllable stability such that the variant Cas9 protein can be turned "on" (i.e., stable) or "off" (i.e., unstable, degraded) depending on the desired conditions. For example, if the degron is a temperature sensitive degron, the variant Cas9 protein may be functional (i.e., "on", stable) below a threshold temperature (e.g., 42° C., 41° C., 40° C., 39° C., 38° C., 37° C., 36° C., 35° C., 34° C., 33° C., 32° C., 31° C., 30° C., etc.) but non-functional (i.e., "off", degraded) above the threshold temperature. As another example, if the degron is a drug inducible degron, the presence or absence of drug can switch the protein from an "off" (i.e., unstable) state to an "on" (i.e., stable) state or vice versa. An exemplary drug inducible degron is derived from the FKBP12 protein. The stability of the degron is controlled by the presence or absence of a small molecule that binds to the degron.

Suitable fusion partners include, but are not limited to, a polypeptide that provides for methyltransferase activity, demethylase activity, acetyltransferase activity, deacetylase activity, kinase activity, phosphatase activity, ubiquitin ligase activity, deubiquitinating activity, adenylation activity, deadenylation activity, SUMOylating activity, deSUMOylating activity, ribosylation activity, deribosylation activity, myristoylation activity, or demyristoylation activity, any of which can be directed at modifying nucleic acid directly (e.g., methylation of DNA or RNA) or at modifying a nucleic acid-associated polypeptide (e.g., a histone, a DNA binding protein, and RNA binding protein, and the like). Further suitable fusion partners include, but are not limited to boundary elements (e.g., CTCF), proteins and fragments thereof that provide periphery recruitment (e.g., Lamin A, Lamin B, etc.), and protein docking elements (e.g., FKBP/FRB, Pil1/Aby1, etc.).

Suitable fusion partners include, but are not limited to, a polypeptide that provides an activity that indirectly increases transcription by acting directly on the target nucleic acid or on a polypeptide (e.g., a histone, a DNA-binding protein, an RNA-binding protein, an RNA editing protein, etc.) associated with the target nucleic acid. Suitable fusion partners include, but are not limited to, a polypeptide that provides for methyltransferase activity, demethylase activity, acetyltransferase activity, deacetylase activity, kinase activity, phosphatase activity, ubiquitin ligase activity, deubiquitinating activity, adenylation activity, deadenylation activity, SUMOylating activity, deSUMOylating activity, ribosylation activity, deribosylation activity, myristoylation activity, or demyristoylation activity.

Additional suitable fusion partners include, but are not limited to, a polypeptide that directly provides for increased transcription and/or translation of a target nucleic acid (e.g., a transcription activator or a fragment thereof, a protein or fragment thereof that recruits a transcription activator, a small molecule/drug-responsive transcription and/or translation regulator, a translation-regulating protein, etc.).

Examples of fusion partners to accomplish increased or decreased transcription include, but are not limited to: (e.g., GAL4, VP16, VP64, the Krüppel associated box (KRAB or SKD); the Mad mSIN3 interaction domain (SID); the ERF repressor domain (ERD), etc.). In some such cases, a Cas9 fusion protein is targeted by the Cas9 guide RNA to a specific location (i.e., sequence) in the target nucleic acid and exerts locus-specific regulation such as blocking RNA polymerase binding to a promoter (which selectively inhibits transcription activator function), increasing transcription, and/or modifying the local chromatin status (e.g., when a fusion sequence is used that modifies the target nucleic acid or modifies a polypeptide associated with the target nucleic acid). In some cases, the changes are transient (e.g., transcription repression or activation). In some cases, the changes are inheritable (e.g., when epigenetic modifications are made to the target nucleic acid or to proteins associated with the target nucleic acid, e.g., nucleosomal histones).

Non-limiting examples of fusion partners for use when targeting ssRNA target nucleic acids include, but are not limited to: splicing factors (e.g., RS domains); protein translation components (e.g., translation initiation, elongation, and/or release factors; e.g., eIF4G); RNA methylases; RNA editing enzymes (e.g., RNA deaminases, e.g., adenosine deaminase acting on RNA (ADAR), including A to I and/or C to U editing enzymes); helicases; RNA-binding proteins; and the like. It is understood that a fusion partner can include the entire protein or in some cases can include a fragment of the protein (e.g., a functional domain).

In some embodiments, the heterologous sequence can be fused to the C-terminus of the Cas9 protein. In some embodiments, the heterologous sequence can be fused to the N-terminus of the Cas9 protein. In some embodiments, the heterologous sequence can be fused to an internal portion (i.e., a portion other than the N- or C-terminus) of the Cas9 protein. In some cases, a heterologous sequence can be fused to both the N- and C-terminus.

In some embodiments, a subject variant Cas9 protein can be linked to a heterologous polypeptide (a heterologous amino acid sequence) via a linker polypeptide (e.g., one or more linker polypeptides). The linker polypeptide may have any of a variety of amino acid sequences. Proteins can be joined by a spacer peptide, generally of a flexible nature, although other chemical linkages are not excluded. Suitable linkers include polypeptides of between about 6 amino acids and about 40 amino acids in length, or between about 6 amino acids and about 25 amino acids in length. These linkers are generally produced by using synthetic, linker-encoding oligonucleotides to couple the proteins. Peptide linkers with a degree of flexibility will generally be preferred. The linking peptides may have virtually any amino acid sequence, bearing in mind that the preferred linkers will have a sequence that results in a generally flexible peptide. The use of small amino acids, such as glycine and alanine, are of use in creating a flexible peptide. The creation of such sequences is routine to those of skill in the art. A variety of different linkers are commercially available and are considered suitable for use.

Exemplary linker polypeptides include glycine polymers $(G)_n$, glycine-serine polymers (including, for example, $(GS)_n$, $GSGGS_n$ (SEQ ID NO: 1098), $GGSGGS_n$ (SEQ ID NO: 1099), and $GGGS_n$ (SEQ ID NO: 1100), where n is an integer of at least one), glycine-alanine polymers, alanine-serine polymers. Exemplary linkers can comprise amino acid sequences including, but not limited to, GGSG (SEQ ID NO: 1101), GGSGG (SEQ ID NO: 1102), GSGSG (SEQ ID NO: 1103), GSGGG (SEQ ID NO: 1104), GGGSG (SEQ ID NO: 1105), GSSSG (SEQ ID NO: 1106), and the like. The ordinarily skilled artisan will recognize that design of a peptide conjugated to any elements described above can include linkers that are all or partially flexible, such that the linker can include a flexible linker as well as one or more portions that confer less flexible structure.

Cas9 Guide RNA

A nucleic acid molecule that binds to a CRISPR/Cas protein (e.g., a Cas9 protein) and targets the complex to a specific location within a target nucleic acid is referred to herein as a "CRISPR/Cas guide nucleic acid" or "CRISPR/Cas guide RNA". When the guide RNA is for a Cas9 protein, it is referred to as a "Cas9 guide RNA."

A Cas9 guide RNA can be said to include two segments, a first segment (referred to herein as a "targeting segment"); and a second segment (referred to herein as a "protein-binding segment"). By "segment" it is meant a segment/section/region of a molecule, e.g., a contiguous stretch of nucleotides in a nucleic acid molecule. A segment can also mean a region/section of a complex such that a segment may comprise regions of more than one molecule.

The first segment (targeting segment) of a Cas9 guide RNA includes a nucleotide sequence (a guide sequence) that is complementary to (and therefore hybridizes with) a specific sequence (a target site) within a target nucleic acid (e.g., a target ssRNA, a target ssDNA, the complementary strand of a double stranded target DNA, etc.). The protein-binding segment (or "protein-binding sequence") interacts with a Cas9 polypeptide. The protein-binding segment of a subject Cas9 guide RNA includes two complementary stretches of nucleotides that hybridize to one another to form a double stranded RNA duplex (dsRNA duplex). Site-specific binding and/or cleavage of the target nucleic acid can occur at locations determined by base-pairing complementarity between the Cas9 guide RNA (the guide sequence of the Cas9 guide RNA) and the target nucleic acid.

A Cas9 guide RNA and a Cas9 protein form a complex (e.g., bind via non-covalent interactions). The Cas9 guide RNA provides target specificity to the complex by including a targeting segment, which includes a guide sequence (a nucleotide sequence that is complementary to a sequence of a target nucleic acid). The Cas9 protein of the complex provides the site-specific activity (e.g., cleavage activity or an activity provided by the Cas9 protein when the Cas9 protein is a chimeric protein, i.e., has a fusion partner). In other words, the Cas9 protein is guided to a target nucleic acid sequence (e.g. a target sequence in a chromosomal nucleic acid, e.g., a chromosome; a target sequence in an extrachromosomal nucleic acid, e.g. an episomal nucleic acid, a minicircle, an ssRNA, an ssDNA, etc.; a target sequence in a mitochondrial nucleic acid; a target sequence in a chloroplast nucleic acid; a target sequence in a plasmid; a target sequence in a viral nucleic acid; etc.) by virtue of its association with the Cas9 guide RNA.

The "guide sequence" also referred to as the "targeting sequence" of a Cas9 guide RNA can be modified so that the Cas9 guide RNA can target a Cas9 protein to any desired sequence of any desired target nucleic acid, with the exception (e.g., as described herein) that the PAM sequence can be taken into account. Thus, for example, a Cas9 guide RNA can have a targeting segment with a sequence that has complementarity with (e.g., can hybridize to) a sequence in a nucleic acid in a eukaryotic cell, e.g., a viral nucleic acid, a eukaryotic nucleic acid (e.g., a eukaryotic chromosome, chromosomal sequence, a eukaryotic RNA, etc.), and the like.

In some embodiments, a subject Cas9 guide RNA includes two separate nucleic acid molecules: an "activator" and a "targeter" and is referred to herein as a "dual Cas9 guide RNA", a "double-molecule Cas9 guide RNA", or a "two-molecule Cas9 guide RNA" a "dual guide RNA", or a "dgRNA." In some embodiments, the activator and targeter are covalently linked to one another (e.g., via intervening nucleotides) and the guide RNA is referred to as a "single guide RNA", a "Cas9 single guide RNA", a "single-molecule Cas9 guide RNA," or a "one-molecule Cas9 guide RNA", or simply "sgRNA."

An example dual Cas9 guide RNA comprises a crRNA-like ("CRISPR RNA"/"targeter"/"crRNA"/"crRNA repeat") molecule and a corresponding tracrRNA-like ("trans-acting CRISPR RNA"/"activator"/"tracrRNA") molecule. A crRNA-like molecule (targeter) comprises both the targeting segment (single stranded) of the guide nucleic acid and a stretch ("duplex-forming segment") of nucleotides that forms one half of the dsRNA duplex of the protein-binding segment of the Cas9 guide RNA. A corresponding tracrRNA-like molecule (activator/tracrRNA) comprises a stretch of nucleotides (duplex-forming segment) that forms the other half of the dsRNA duplex of the protein-binding segment of the guide nucleic acid. In other words, a stretch of nucleotides of a crRNA-like molecule are complementary to and hybridize with a stretch of nucleotides of a tracrRNA-like molecule to form the dsRNA duplex of the protein-binding domain of the Cas9 guide RNA. As such, each targeter molecule can be said to have a corresponding activator molecule (which has a region that hybridizes with the targeter). The targeter molecule additionally provides the targeting segment. Thus, a targeter and an activator molecule (as a corresponding pair) hybridize to form a Cas9 guide RNA. The exact sequence of a given crRNA or tracrRNA molecule is characteristic of the species in which the RNA molecules are found. A subject dual Cas9 guide RNA can include any corresponding activator and targeter pair.

The term "activator" or "activator RNA" is used herein to mean a tracrRNA-like molecule (tracrRNA: "trans-acting CRISPR RNA") of a Cas9 dual guide RNA (and therefore of a Cas9 single guide RNA when the "activator" and the "targeter" are linked together by, e.g., intervening nucleotides). Thus, for example, a Cas9 guide RNA (dgRNA or sgRNA) comprises an activator sequence (e.g., a tracrRNA sequence). A tracr molecule (a tracrRNA) is a naturally existing molecule that hybridizes with a CRISPR RNA molecule (a crRNA) to form a Cas9 dual guide RNA. The term "activator" is used herein to encompass naturally existing tracrRNAs, but also to encompass tracrRNAs with modifications (e.g., truncations, sequence variations, base modifications, backbone modifications, linkage modifications, etc.) where the activator retains at least one function of a tracrRNA (e.g., contributes to the dsRNA duplex to which Cas9 binds). In some cases the activator provides one or more stem loops that can interact with Cas9. An activator can be referred to as having a tracr sequence (tracrRNA sequence) and in some cases is a tracrRNA, but the term "activator" is not limited to naturally existing tracrRNAs.

The term "targeter" or "targeter RNA" is used herein to refer to a crRNA-like molecule (crRNA: "CRISPR RNA") of a Cas9 dual guide RNA (and therefore of a Cas9 single guide RNA when the "activator" and the "targeter" are linked together, e.g., by intervening nucleotides). Thus, for example, a Cas9 guide RNA (dgRNA or sgRNA) comprises a targeting segment (which includes nucleotides that hybridize with (are complementary to) a target nucleic acid, and a duplex-forming segment (e.g., a duplex forming segment of a crRNA, which can also be referred to as a crRNA repeat). Because the sequence of a targeting segment (the segment that hybridizes with a target sequence of a target nucleic acid) of a targeter is modified by a user to hybridize with a desired target nucleic acid, the sequence of a targeter will often be a non-naturally occurring sequence. However, the duplex-forming segment of a targeter (described in more detail below), which hybridizes with the duplex-forming segment of an activator, can include a naturally existing sequence (e.g., can include the sequence of a duplex-forming segment of a naturally existing crRNA, which can also be referred to as a crRNA repeat). Thus, the term targeter is used herein to distinguish from naturally occurring crRNAs, despite the fact that part of a targeter (e.g., the duplex-forming segment) often includes a naturally occurring sequence from a crRNA. However, the term "targeter" encompasses naturally occurring crRNAs.

A Cas9 guide RNA (e.g. a dual guide RNA or a single guide RNA) can be comprised of any corresponding activator and targeter pair. In some cases, the duplex forming segments can be swapped between the activator and the targeter. In other words, in some cases, the targeter includes a sequence of nucleotides from a duplex forming segment of a tracrRNA (which sequence would normally be part of an activator) while the activator includes a sequence of nucleotides from a duplex forming segment of a crRNA (which sequence would normally be part of a targeter).

As noted above, a targeter comprises both the targeting segment (single stranded) of the Cas9 guide RNA and a stretch ("duplex-forming segment") of nucleotides that forms one half of the dsRNA duplex of the protein-binding segment of the Cas9 guide RNA. A corresponding tracrRNA-like molecule (activator) comprises a stretch of nucleotides (a duplex-forming segment) that forms the other half of the dsRNA duplex of the protein-binding segment of the Cas9 guide RNA. In other words, a stretch of nucleotides of the targeter is complementary to and hybridizes with a stretch of nucleotides of the activator to form the dsRNA duplex of the protein-binding segment of a Cas9 guide RNA. As such, each targeter can be said to have a corresponding activator (which has a region that hybridizes with the targeter). The targeter molecule additionally provides the targeting segment. Thus, a targeter and an activator (as a corresponding pair) hybridize to form a Cas9 guide RNA.

The particular sequence of a given naturally existing crRNA or tracrRNA molecule is characteristic of the species in which the RNA molecules are found. Examples of suitable activator and targeter are well known in the art.

A Cas9 guide RNA (e.g. a dual guide RNA or a single guide RNA) can include any corresponding activator and targeter pair. Non-limiting examples of nucleotide sequences that can be included in a Cas9 guide RNA (dgRNA or sgRNA) include sequences set forth in SEQ ID NOs: 831-1079, or complements thereof. For example, in some cases, sequences from SEQ ID NOs: 831-961 (which are from tracrRNAs) or complements thereof, can pair with sequences from SEQ ID NOs: 966-1079 (which are from crRNAs), or complements thereof, to form a dsRNA duplex of a protein binding segment.

Targeting Segment of a Cas9 Guide RNA

The first segment of a subject guide nucleic acid includes a guide sequence (a nucleotide sequence that is complementary to a sequence (a target site) in a target nucleic acid). In other words, the targeting segment of a subject guide nucleic acid can interact with a target nucleic acid (e.g., a single stranded RNA (ssRNA) and/or a single stranded DNA (ssDNA)) in a sequence-specific manner via hybridization (i.e., base pairing). As such, the nucleotide sequence of the targeting segment may vary (depending on the target) and can determine the location within the target nucleic acid that the Cas9 guide RNA and the target nucleic acid will interact. The targeting segment of a Cas9 guide RNA can be modified (e.g., by genetic engineering)/designed to hybridize to any desired sequence (target site) within a target nucleic acid (e.g., a eukaryotic target nucleic acid).

The targeting segment can have a length of 7 or more nucleotides (nt) (e.g., 8 or more, 9 or more, 10 or more, 12 or more, 15 or more, 20 or more, 25 or more, 30 or more, or 40 or more nucleotides). In some cases, the targeting segment can have a length of from 7 to 100 nucleotides (nt) (e.g., from 7 to 80 nt, from 7 to 60 nt, from 7 to 40 nt, from 7 to 30 nt, from 7 to 25 nt, from 7 to 22 nt, from 7 to 20 nt, from 7 to 18 nt, from 8 to 80 nt, from 8 to 60 nt, from 8 to 40 nt, from 8 to 30 nt, from 8 to 25 nt, from 8 to 22 nt, from 8 to 20 nt, from 8 to 18 nt, from 10 to 100 nt, from 10 to 80 nt, from 10 to 60 nt, from 10 to 40 nt, from 10 to 30 nt, from 10 to 25 nt, from 10 to 22 nt, from 10 to 20 nt, from 10 to 18 nt, from 12 to 100 nt, from 12 to 80 nt, from 12 to 60 nt, from 12 to 40 nt, from 12 to 30 nt, from 12 to 25 nt, from 12 to 22 nt, from 12 to 20 nt, from 12 to 18 nt, from 14 to 100 nt, from 14 to 80 nt, from 14 to 60 nt, from 14 to 40 nt, from 14 to 30 nt, from 14 to 25 nt, from 14 to 22 nt, from 14 to 20 nt, from 14 to 18 nt, from 16 to 100 nt, from 16 to 80 nt, from 16 to 60 nt, from 16 to 40 nt, from 16 to 30 nt, from 16 to 25 nt, from 16 to 22 nt, from 16 to 20 nt, from 16 to 18 nt, from 18 to 100 nt, from 18 to 80 nt, from 18 to 60 nt, from 18 to 40 nt, from 18 to 30 nt, from 18 to 25 nt, from 18 to 22 nt, or from 18 to 20 nt).

The nucleotide sequence (the targeting sequence) of the targeting segment that is complementary to a nucleotide sequence (target site) of the target nucleic acid can have a length of 10 nt or more. For example, the targeting sequence of the targeting segment that is complementary to a target site of the target nucleic acid can have a length of 12 nt or more, 15 nt or more, 18 nt or more, 19 nt or more, or 20 nt or more. In some cases, the nucleotide sequence (the targeting sequence) of the targeting segment that is complementary to a nucleotide sequence (target site) of the target nucleic acid has a length of 12 nt or more. In some cases, the nucleotide sequence (the targeting sequence) of the targeting segment that is complementary to a nucleotide sequence (target site) of the target nucleic acid has a length of 18 nt or more.

For example, the targeting sequence of the targeting segment that is complementary to a target sequence of the target nucleic acid can have a length of from 10 to 100 nucleotides (nt) (e.g., from 10 to 90 nt, from 10 to 75 nt, from 10 to 60 nt, from 10 to 50 nt, from 10 to 35 nt, from 10 to 30 nt, from 10 to 25 nt, from 10 to 22 nt, from 10 to 20 nt, from 12 to 100 nt, from 12 to 90 nt, from 12 to 75 nt, from 12 to 60 nt, from 12 to 50 nt, from 12 to 35 nt, from 12 to 30 nt, from 12 to 25 nt, from 12 to 22 nt, from 12 to 20 nt, from 15 to 100 nt, from 15 to 90 nt, from 15 to 75 nt, from 15 to 60 nt, from 15 to 50 nt, from 15 to 35 nt, from 15 to 30 nt, from 15 to 25 nt, from 15 to 22 nt, from 15 to 20 nt, from 17 to 100 nt, from 17 to 90 nt, from 17 to 75 nt, from 17 to 60 nt, from 17 to 50 nt, from 17 to 35 nt, from 17 to 30 nt, from 17 to 25 nt, from 17 to 22 nt, from 17 to 20 nt, from 18 to 100 nt, from 18 to 90 nt, from 18 to 75 nt, from 18 to 60 nt, from 18 to 50 nt, from 18 to 35 nt, from 18 to 30 nt, from 18 to 25 nt, from 18 to 22 nt, or from 18 to 20 nt). In some cases, the targeting sequence of the targeting segment that is complementary to a target sequence of the target nucleic acid has a length of from 15 nt to 30 nt. In some cases, the targeting sequence of the targeting segment that is complementary to a target sequence of the target nucleic acid has a length of from 15 nt to 25 nt. In some cases, the targeting sequence of the targeting segment that is complementary to a target sequence of the target nucleic acid has a length of from 18 nt to 30 nt. In some cases, the targeting sequence of the targeting segment that is complementary to a target sequence of the target nucleic acid has a length of from 18 nt to 25 nt. In some cases, the targeting sequence of the targeting segment that is complementary to a target sequence of the target nucleic acid has a length of from 18 nt to 22 nt. In some cases, the targeting sequence of the targeting segment that is complementary to a target site of the target nucleic acid is 20 nucleotides in length. In some cases, the targeting sequence of the targeting segment that is complementary to a target site of the target nucleic acid is 19 nucleotides in length.

The percent complementarity between the targeting sequence of the targeting segment and the target site of the target nucleic acid can be 60% or more (e.g., 65% or more, 70% or more, 75% or more, 80% or more, 85% or more, 90% or more, 95% or more, 97% or more, 98% or more, 99% or more, or 100%). In some cases, the percent complementarity between the targeting sequence of the targeting segment and the target site of the target nucleic acid is 100% over the seven contiguous 5'-most nucleotides of the target site of the target nucleic acid. In some cases, the percent complementarity between the targeting sequence of the targeting segment and the target site of the target nucleic acid is 60% or more over about 20 contiguous nucleotides. In some cases, the percent complementarity between the targeting sequence of the targeting segment and the target site of the target nucleic acid is 100% over the fourteen contiguous 5'-most nucleotides of the target site of the target nucleic acid and as low as 0% or more over the remainder. In such a case, the targeting sequence can be considered to be 14 nucleotides in length. In some cases, the percent complementarity between the targeting sequence of the targeting segment and the target site of the target nucleic acid is 100% over the seven contiguous 5'-most nucleotides of the target site of the target nucleic acid and as low as 0% or more over the remainder. In such a case, the targeting sequence can be considered to be 20 nucleotides in length.

In some cases, the percent complementarity between the targeting sequence of the targeting segment and the target site of the target nucleic acid is 100% over the 7 contiguous 5'-most nucleotides of the target site of the target nucleic acid (which can be complementary to the 3'-most nucleotides of the targeting sequence of the Cas9 guide RNA). In some cases, the percent complementarity between the targeting sequence of the targeting segment and the target site of the target nucleic acid is 100% over the 8 contiguous 5'-most nucleotides of the target site of the target nucleic acid (which can be complementary to the 3'-most nucleotides of the targeting sequence of the Cas9 guide RNA). In some cases, the percent complementarity between the targeting sequence of the targeting segment and the target site of the target nucleic acid is 100% over the 9 contiguous 5'-most nucleotides of the target site of the target nucleic acid (which can be complementary to the 3'-most nucleotides of the targeting sequence of the Cas9 guide RNA). In some cases, the percent complementarity between the targeting sequence of the targeting segment and the target site of the target nucleic acid is 100% over the 10 contiguous 5'-most nucleotides of the target site of the target nucleic acid (which can be complementary to the 3'-most nucleotides of the targeting sequence of the Cas9 guide RNA). In some cases, the percent complementarity between the targeting sequence of the targeting segment and the target site of the target nucleic acid is 60% or more (e.g., e.g., 65% or more, 70% or more, 75% or more, 80% or more, 85% or more, 90% or more, 95% or more, 97% or more, 98% or more, 99% or more, or 100%) over about 20 contiguous nucleotides.

In some cases, the percent complementarity between the targeting sequence of the targeting segment and the target site of the target nucleic acid is 100% over the 7 contiguous 5'-most nucleotides of the target site of the target nucleic acid and as low as 0% or more over the remainder. In such a case, the targeting sequence can be considered to be 7 nucleotides in length. In some cases, the percent complementarity between the targeting sequence of the targeting segment and the target site of the target nucleic acid is 100% over the 8 contiguous 5'-most nucleotides of the target site of the target nucleic acid and as low as 0% or more over the remainder. In such a case, the targeting sequence can be considered to be 8 nucleotides in length. In some cases, the percent complementarity between the targeting sequence of the targeting segment and the target site of the target nucleic acid is 100% over the 9 contiguous 5'-most nucleotides of the target site of the target nucleic acid and as low as 0% or more over the remainder. In such a case, the targeting sequence can be considered to be 9 nucleotides in length. In some cases, the percent complementarity between the targeting sequence of the targeting segment and the target site of the target nucleic acid is 100% over the 10 contiguous 5'-most nucleotides of the target site of the target nucleic acid and as low as 0% or more over the remainder. In such a case, the targeting sequence can be considered to be 10 nucleotides in length. In some cases, the percent complementarity between the targeting sequence of the targeting segment and the target site of the target nucleic acid is 100% over the 11 contiguous 5'-most nucleotides of the target site of the target nucleic acid and as low as 0% or more over the remainder. In such a case, the targeting sequence can be considered to be 11 nucleotides in length. In some cases, the percent complementarity between the targeting sequence of the targeting segment and the target site of the target nucleic acid is 100% over the 12 contiguous 5'-most nucleotides of the target site of the target nucleic acid and as low as 0% or more over the remainder. In such a case, the targeting sequence can be considered to be 12 nucleotides in length. In some cases, the percent complementarity between the targeting sequence of the targeting segment and the target site of the target nucleic acid is 100% over the 13 contiguous 5'-most nucleotides of the target site of the target nucleic acid and as low as 0% or more over the remainder. In such a case, the targeting sequence can be considered to be 13 nucleotides in length. In some cases, the percent complementarity between the targeting sequence of the targeting segment and the target site of the target nucleic acid is 100% over the 14 contiguous 5'-most nucleotides of the target site of the target nucleic acid and as low as 0% or more over the remainder. In such a case, the targeting sequence can be considered to be 14 nucleotides in length.

Constant Region of a Guide RNA

Figure 11:
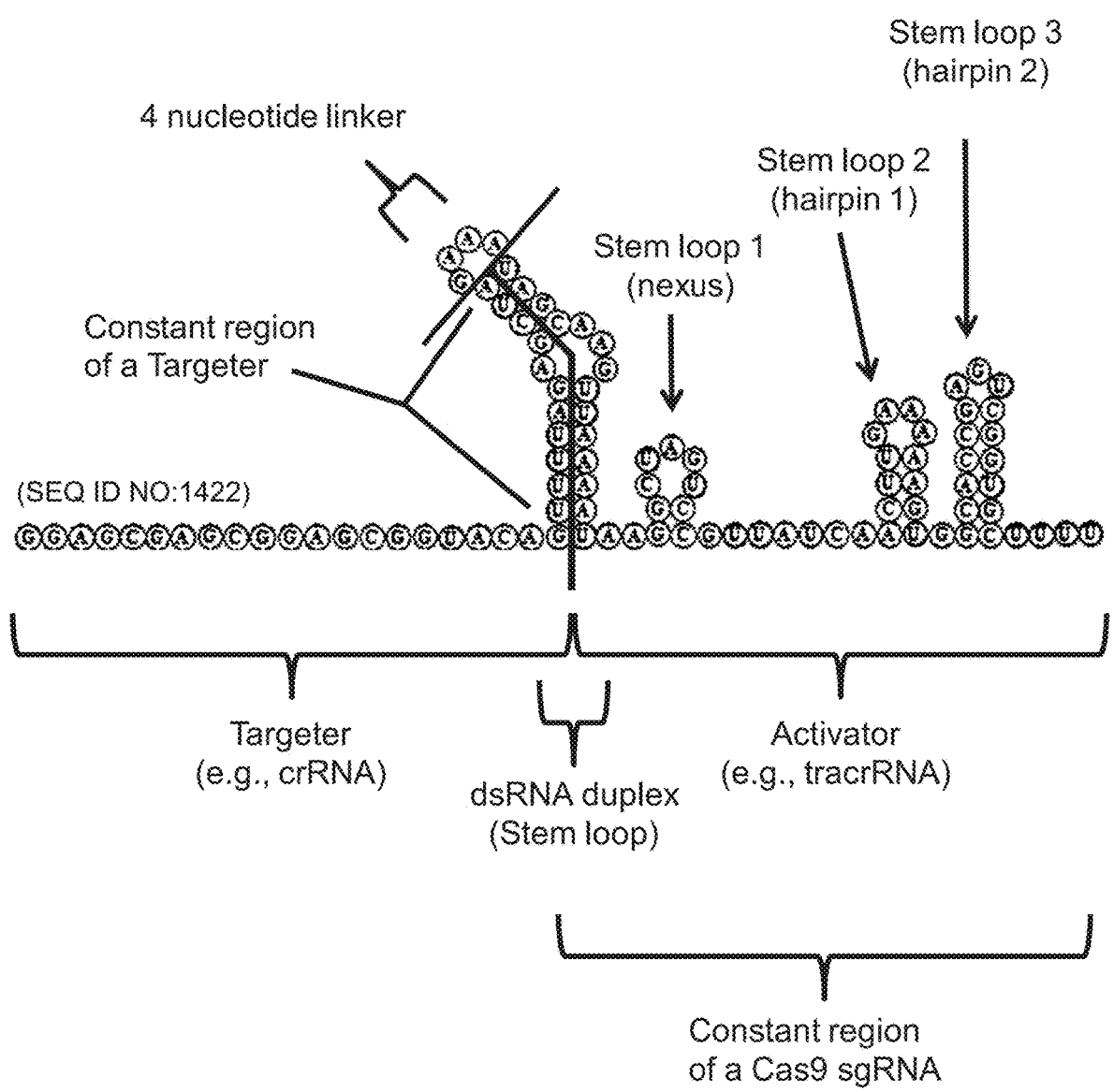
FIG. 11 presents a schematic diagram of an example Cas9 single guide RNA (Cas9 sgRNA). The constant region is labeled for the sgRNA (and for the Targeter in cases where the Cas9 guide RNA is a dual guide RNA).

The "constant region" of a guide RNA as used herein is a region (portion, segment) of the guide RNA that does not need to change when a different target is selected. For example, when a different target sequence is targeted, a different guide sequence is used as part of the guide RNA, but the rest of the Cas9 guide RNA (3' of the guide sequence) need not change. For example, in the case of a Cas9 guide RNA, the constant region can encompass all or a portion of the guide RNA outside of the guide sequence. For example, if the Cas9 guide RNA is a dual guide RNA, then a suitable constant region can be the constant region of a targeter (e.g., targeter RNA) (i.e., the region of a targeter RNA that does not include the guide sequence, e.g., the portion of the targeter RNA that is 3' of the guide sequence). See FIG. 11 for a schematic of a Cas9 guide RNA.

A subject library can be generated that includes DNA molecules that each encode a Cas9 targeter RNA (e.g., where the guide sequence is variable and portion 3' of the guide sequence is constant). In order to use such a library (e.g., for targeting a Cas9 protein to a target nucleic acid), an activator RNA (e.g., tracrRNA) (or a DNA encoding an activator RNA) can be provided (e.g., as part of a kit, at the time of use, provided by the user, etc.). Because the activator RNA is a constant region of a guide RNA (by definition, e.g., the sequence of the activator RNA portion of a Cas9 guide RNA need not change as different sequences are targeted, i.e., the sequence of the activator RNA portion of a Cas9 guide RNA need not change when the guide sequence is changed), the same activator RNA could be used with each of the Cas9 targeter RNAs present in the generated library.

If the Cas9 guide RNA is a single guide RNA (sgRNA), then a suitable constant region can be the entire region of the guide RNA outside of the guide sequence, which can include (i) the constant region of the targeter RNA, (ii) the activator RNA, e.g., the entire activator RNA, and (iii) any intervening nucleotides that connect the targeter RNA to the activator RNA. Thus, a subject library can be generated that includes DNA molecules that each encode a Cas9 single guide RNA (sgRNA) (e.g., where the guide sequence of the DNA molecules in the library is variable).

Examples of the constant region of a targeter (e.g., targeter RNA) include, but are not limited to, those set forth in SEQ ID NOs: 1092-1097 (which are illustrative examples of constant regions of targeter RNAs derived from *S. pyogenes* sequences). Examples of the constant region of a Cas9 single guide RNA include, but are not limited to, those set forth in SEQ ID NOs: 1080-1091 (which are illustrative examples of constant regions of Cas9 single guide RNAs derived from *S. pyogenes* sequences).

Examples of various Cas9 guide RNAs (and therefore associated constant regions) can be found in the art, for example, see Jinek et al., Science. 2012 Aug. 17; 337(6096): 816-21; Chylinski et al., RNA Biol. 2013 May; 10(5):726-37; Ma et al., Biomed Res Int. 2013; 2013:270805; Hou et al., Proc Natl Acad Sci USA. 2013 Sep. 24; 110(39):15644-9; Jinek et al., Elife. 2013; 2:e00471; Pattanayak et al., Nat Biotechnol. 2013 September; 31(9):839-43; Qi et al, Cell. 2013 Feb. 28; 152(5):1173-83; Wang et al., Cell. 2013 May 9; 153(4):910-8; Auer et. al., Genome Res. 2013 Oct. 31; Chen et. al., Nucleic Acids Res. 2013 Nov. 1; 41(20):e19; Cheng et. al., Cell Res. 2013 October; 23(10):1163-71; Cho et. al., Genetics. 2013 November; 195(3):1177-80; DiCarlo et al., Nucleic Acids Res. 2013 April; 41(7):4336-43; Dickinson et. al., Nat Methods. 2013 October; 10(10):1028-34; Ebina et. al., Sci Rep. 2013; 3:2510; Fujii et. al, Nucleic Acids Res. 2013 Nov. 1; 41(20):e187; Hu et. al., Cell Res. 2013 November; 23(11):1322-5; Jiang et. al., Nucleic Acids Res. 2013 Nov. 1; 41(20):e188; Larson et. al., Nat Protoc. 2013 November; 8(11):2180-96; Mali et. al., Nat Methods. 2013 October; 10(10):957-63; Nakayama et. al., Genesis. 2013 December; 51(12):835-43; Ran et. al., Nat Protoc. 2013 November; 8(11):2281-308; Ran et. al., Cell. 2013 Sep. 12; 154(6):1380-9; Upadhyay et. al., G3 (Bethesda). 2013 Dec. 9; 3(12):2233-8; Walsh et. al., Proc Natl Acad Sci USA. 2013 Sep. 24; 110(39):15514-5; Xie et. al., Mol Plant. 2013 Oct. 9; Yang et. al., Cell. 2013 Sep. 12; 154(6):1370-9; Briner et al., Mol Cell. 2014 Oct. 23; 56(2):333-9; and U.S. patents and patent applications: U.S. Pat. Nos. 8,906,616; 8,895,308; 8,889,418; 8,889,356; 8,871,445; 8,865,406; 8,795,965; 8,771,945; 8,697,359; 20140068797; 20140170753; 20140179006; 20140179770; 20140186843; 20140186919; 20140186958; 20140189896; 20140227787; 20140234972; 20140242664; 20140242699; 20140242700; 20140242702; 20140248702; 20140256046; 20140273037; 20140273226; 20140273230; 20140273231; 20140273232; 20140273233; 20140273234; 20140273235; 20140287938; 20140295556; 20140295557; 20140298547; 20140304853; 20140309487; 20140310828; 20140310830; 20140315985; 20140335063; 20140335620; 20140342456; 20140342457; 20140342458; 20140349400; 20140349405; 20140356867; 20140356956; 20140356958; 20140356959; 20140357523; 20140357530; 20140364333; and 20140377868; all of which are hereby incorporated by reference in their entirety.

Target DNA Molecule

A target nucleic acid can be any nucleic acid (e.g., DNA, RNA), can be double strand or single stranded, can be any type of nucleic acid (e.g., a chromosome, derived from a chromosome, chromosomal, plasmid, viral, extracellular, intracellular, mitochondrial, chloroplast, linear, circular, etc.) and can be from any organism (e.g., as long as the Cas9 guide RNA can hybridize to a target sequence in a target nucleic acid, that target nucleic acid can be targeted). If a target nucleic acid is not double stranded DNA (e.g, RNA or single stranded DNA) any convenient step can first be taken to generate a double stranded target DNA that can be used in the subject methods.

For example, a subject DNA molecule can be any DNA molecule or collection of DNA molecules (e.g., a chromosome, a collection of chromosomes, etc.) from any source as long as the DNA molecule has two or more PAM sequences that are recognized by the one or PAM-recognition DNA endonucleases that are used in the subject methods. Because PAM sequences are relatively short, all or nearly all naturally existing sources of DNA (including DNA from any organism) will include two more PAM sequences. Examples of the types of suitable target DNA include but are not limited to: chromosomal DNA (e.g., a chromosome, a genome, a collection of chromosomes), viral DNA, unknown DNA collected from any source (e.g., collected from an environmental source), DNA from an organelle, mitochondrial DNA, chloroplast DNA, and the like). Examples of suitable cellular sources for the target DNA include, but are not limited to: a eukaryotic cell; a prokaryotic cell, (e.g., a bacterial cell or an archaeal cell), a cell of a single-cell eukaryotic organism; a plant cell (e.g., rice, soy, maize, corn, wheat, tomato, tobacco, fruit tree, etc.); an algal cell (e.g., *Botryococcus braunii*, *Chlamydomonas reinhardtii*, *Nannochloropsis gaditana*, *Chlorella pyrenoidosa*, *Sargassum patens C. Agardh*, and the like); a fungal cell (e.g., a yeast cell); an animal cell; a cell from an invertebrate animal (e.g. fruit fly, cnidarian, echinoderm, nematode, planarian, etc.); a cell from a vertebrate animal (e.g., fish, e.g., zebrafish, amphibian, e.g, frog, reptile, bird, e.g., chicken, mammal, and the like); a cell from a mammal (e.g., zoo animal, pet, canine, equine, porcine, rodent, primate, human, etc.); and the like.

Target Nucleic Acids and Target Cells of Interest

A target nucleic acid for a Cas9 guide RNA/Cas9 method can be DNA or RNA. A target nucleic acid can be double stranded (e.g., dsDNA, dsRNA) or single stranded (e.g., ssRNA, ssDNA). In some cases, a target nucleic acid is single stranded. In some cases, a target nucleic acid is a single stranded RNA (ssRNA). In some cases, a target ssRNA (e.g., a target cell ssRNA, a viral ssRNA, etc.) is selected from: mRNA, rRNA, tRNA, non-coding RNA (ncRNA), long non-coding RNA (lncRNA), and microRNA (miRNA). In some cases, a target nucleic acid is a single stranded DNA (ssDNA) (e.g., a viral DNA). As noted above, in some cases, a target nucleic acid is single stranded.

A target nucleic acid can be located anywhere, for example, outside of a cell in vitro, inside of a cell in vitro, inside of a cell in vivo, inside of a cell ex vivo. Suitable target cells (which can comprise target nucleic acids) include, but are not limited to: a bacterial cell; an archaeal cell; a cell of a single-cell eukaryotic organism; a plant cell; an algal cell, e.g., *Botryococcus braunii*, *Chlamydomonas reinhardtii*, *Nannochloropsis gaditana*, *Chlorella pyrenoidosa*, *Sargassum patens C. Agardh*, and the like; a fungal cell (e.g., a yeast cell); an animal cell; a cell from an invertebrate animal (e.g. fruit fly, cnidarian, echinoderm, nematode, etc.); a cell from a vertebrate animal (e.g., fish, amphibian, reptile, bird, mammal); a cell from a mammal (e.g., a cell from a rodent, a cell from a human, etc.); and the like. Any type of cell may be of interest (e.g. a stem cell, e.g. an embryonic stem (ES) cell, an induced pluripotent stem (iPS) cell, a germ cell (e.g., an oocyte, a sperm, an oogonia, a spermatogonia, etc.), a somatic cell, e.g. a fibroblast, a hematopoietic cell, a neuron, a muscle cell, a bone cell, a hepatocyte, a pancreatic cell; an in vitro or in vivo embryonic cell of an embryo at any stage, e.g., a 1-cell, 2-cell, 4-cell, 8-cell, etc. stage zebrafish embryo; etc.). Cells may be from established cell lines or they may be primary cells, where "primary cells", "primary cell lines", and "primary cultures" are used interchangeably herein to refer to cells and cells cultures that have been derived from a subject and allowed to grow in vitro for a limited number of passages, i.e. splittings, of the culture. For example, primary cultures are cultures that may have been passaged 0 times, 1 μme, 2 times, 4 times, 5 times, 10 times, or 15 times, but not enough times go through the crisis stage. Typically, the primary cell lines are maintained for fewer than 10 passages in vitro. Target cells can be unicellular organisms and/or can be grown in culture. If the cells are primary cells, they may be harvest from an individual by any convenient method. For example, leukocytes may be conveniently harvested by apheresis, leukocytapheresis, density gradient separation, etc., while cells from tissues such as skin, muscle, bone marrow, spleen, liver, pancreas, lung, intestine, stomach, etc. can be conveniently harvested by biopsy.

In some of the above applications, the subject methods may be employed to generate guide RNAs that can be used to induce target nucleic acid cleavage, target nucleic acid modification, and/or to bind target nucleic acids (e.g., for visualization, for collecting and/or analyzing, etc.) in mitotic or post-mitotic cells in vivo and/or ex vivo and/or in vitro (e.g., to disrupt production of a protein encoded by a targeted mRNA). Because the guide RNA provides specificity by hybridizing to target nucleic acid, a mitotic and/or post-mitotic cell of interest in the disclosed methods may include a cell from any organism (e.g. a bacterial cell, an archaeal cell, a cell of a single-cell eukaryotic organism, a plant cell, an algal cell, e.g., *Botryococcus braunii, Chlamydomonas reinhardtii, Nannochloropsis gaditana, Chlorella pyrenoidosa, Sargassum patens C. Agardh*, and the like, a fungal cell (e.g., a yeast cell), an animal cell, a cell from an invertebrate animal (e.g. fruit fly, cnidarian, echinoderm, nematode, etc.), a cell from a vertebrate animal (e.g., fish, amphibian, reptile, bird, mammal), a cell from a mammal, a cell from a rodent, a cell from a human, etc.).

"Protospacer Adjacent Motif" (PAM)

A wild type CRISPR/Cas protein (e.g., Cas9 protein) normally has nuclease activity that cleaves a target nucleic acid (e.g., a double stranded DNA (dsDNA)) at a target site defined by the region of complementarity between the guide sequence of the guide RNA and the target nucleic acid. In some cases, site-specific targeting to the target nucleic acid occurs at locations determined by both (i) base-pairing complementarity between the guide nucleic acid and the target nucleic acid; and (ii) a short motif referred to as the "protospacer adjacent motif" (PAM) in the target nucleic acid. For example, when a Cas9 protein binds to (in some cases cleaves) a dsDNA target nucleic acid, the PAM sequence that is recognized (bound) by the Cas9 polypeptide is present on the non-complementary strand (the strand that does not hybridize with the targeting segment of the guide nucleic acid) of the target DNA. In some cases, a PAM sequence has a length in a range of from 1 nt to 15 nt (e.g., 1 nt to 14 nt, 1 nt to 13 nt, 1 nt to 12 nt, 1 nt to 11 nt, 1 nt to 10 nt, 1 nt to 9 nt, 1 nt to 9 nt, 1 nt to 8 nt, 1 nt to 7 nt, 1 nt to 6 nt, 1 nt to 5 nt, 1 nt to 4 nt, 1 nt to 3 nt, 2 nt to 15 nt, 2 nt to 14 nt, 2 nt to 13 nt, 2 nt to 12 nt, 2 nt to 11 nt, 2 nt to 10 nt, 2 nt to 9 nt, 2 nt to 8 nt, 2 nt to 7 nt, 2 nt to 6 nt, 2 nt to 5 nt, 2 nt to 4 nt, 2 nt to 3 nt, 2 nt, or 3 nt).

CRISRPR/Cas (e.g., Cas9) proteins from different species can have different PAM sequence requirements. For example, in some embodiments (e.g., when the Cas9 protein is derived from *S. pyogenes* or a closely related Cas9 is used; see for example, Chylinski et al., RNA Biol. 2013 May; 10(5):726-37; and Jinek et al., Science. 2012 Aug. 17; 337(6096):816-21; both of which are hereby incorporated by reference in their entirety), the PAM sequence is NRG because the *S. pyogenes* Cas9 PAM (PAM sequence) is NAG or NGG (or NRG where "R" is A or G). For example, a Cas9 PAM sequence for *S. pyogenes* Cas9 is: NGG, NAG, AGG, CGG, GGG, TGG, AAG, CAG, GAG, and TAG.

In some embodiments (e.g., when a Cas9 protein is derived from the Cas9 protein of *Neisseria meningitidis* or a closely related Cas9 is used), the PAM sequence (e.g., of a target nucleic acid) can be 5'-NNNNGANN-3', 5'-NNNNGTTN-3', 5'-NNNNGNNT-3', 5'-NNNNGTNN-3', 5'-NNNNGNTN-3', or 5'-NNNNGATT-3', where N is any nucleotide. In some embodiments (e.g., when a Cas9 protein is derived from *Streptococcus thermophilus* #1 or a closely related Cas9 is used), the PAM sequence (e.g., of a target nucleic acid) can be 5'-NNAGAA-3', 5'-NNAGGA-3', 5'-NNGGAA-3', 5'-NNANAA-3', or 5'-NNGGGA-3' where N is any nucleotide. In some embodiments (e.g., when a Cas9 protein is derived from *Treponema denticola* (TD) or a closely related Cas9 is used), the PAM sequence (e.g., of a target nucleic acid) can be 5'-NAAAAN-3', 5'-NAAAAC-3', 5'-NAAANC-3', 5'-NANAAC-3', or 5'-NNAAAC-3', where N is any nucleotide. As would be known by one of ordinary skill in the art, additional PAM sequences for other Cas9 polypeptides can readily be determined using bioinformatic analysis (e.g, analysis of genomic sequencing data). See Esvelt et al., Nat Methods. 2013 November; 10(11):1116-21, for additional information.

PAM-Recognition DNA Endonucleases

In some cases, such a DNA endonucleases is referred to herein as a PAM-recognition DNA endonuclease. A "PAM-recognition DNA endonuclease" as used herein refers to a DNA endonuclease that specifically binds to a recognition site (recognition sequence) that includes a PAM sequence (e.g., a Cas9 PAM). In some cases, a PAM-recognition DNA endonuclease specifically binds to and cleaves within a recognition site (recognition sequence) that includes a PAM sequence (e.g., a Cas9 PAM). In cases where a recognition site of a PAM-recognition DNA endonuclease includes a Cas9 PAM, the endonuclease can be referred to as a Cas9 PAM-recognition DNA endonuclease.

In many cases, the recognition sequence includes nucleotides in addition to the PAM sequence. For example, the recognition sequence of the PAM-recognition DNA endonuclease HpaII is CCGG (C/CGG where "/" is the cleavage site). Thus, while HpaII does not recognize/cleave all PAM sequences, it has a recognition site that includes a PAM sequence and is therefore referred to herein as a PAM-recognition DNA endonuclease. HpaII is an example of a DNA endonuclease that cleaves specifically binds to and cleaves within a recognition site (recognition sequence) that includes a PAM sequence. Because the recognition site of HpaII includes a Cas9 PAM, HpaII can also be referred to as a Cas9 PAM-recognition DNA endonuclease.

In some cases, a DNA molecule (e.g., a target DNA such as chromosomal DNA) is contacted with one or more (e.g., two or more, three or more, four or more, etc.) (e.g., a composition (e.g., a cocktail) that includes two or more, three or more, or four or more) PAM-recognition DNA endonucleases. In some cases, a PAM-recognition DNA endonuclease is selected from: BfaI, HpaII, ScrFI, MspI, BstNI, NciI, BsiSI, HapII, MaeI, XspI, AsuC2I, BcnI, BpuMI, CauII, BciT130I, BptI, BseBI, BsiLI, Bst2UI, BstOI, MvaI, Bme1390I, BmrFI, and MspR9I. In some cases, a DNA molecule (e.g., a target DNA such as chromosomal DNA) is contacted with two or more (e.g., three or more, four or more, etc.) (e.g., a composition (e.g., a cocktail) that includes two or more, three or more, or four or more) PAM-recognition DNA endonucleases selected from the group consisting of: BfaI, HpaII, ScrFI, MspI, BstNI, NciI, BsiSI, HapII, MaeI, XspI, AsuC2I, BcnI, BpuMI, CauII, BciT130I, BptI, BseBI, BsiLI, Bst2UI, BstOI, MvaI, Bme1390I, BmrFI, and MspR9I. In some cases, a DNA molecule (e.g., a target DNA such as chromosomal DNA) is contacted with a composition (e.g., a cocktail) that includes the PAM-recognition DNA endonucleases BfaI, HpaII, and ScrFI.

The recognition sites for the PAM-recognition DNA endonucleases listed above are:

BfaI: C/TAG
HpaII: C/CGG
ScrFI: CC/NGG
MspI: C/CGG

BstNI: CC/WGG
NciI: CC/SGG
BsiSI, HapII: C/CGG
MaeI, XspI: C/TAG
AsuC2I, BcnI, BpuMI, CauII: CC/SGG
BciT130I, BptI, BseBI, BsiLI, Bst2UI, BstOI, MvaI: CC/WGG
Bme1390I, BmrFI, MspR9I: CC/NGG
where "N" is any nucleotide (e.g., A,G,C,T); "W" is A or T; and "S" is G or C.

In some cases (e.g., as above), a PAM-recognition DNA endonuclease cleaves in the recognition sequence immediately 5' to the PAM. However, DNA endonucleases that recognize a PAM (e.g., an NRG, NGG, NAG motif) but cut at a location other than immediately 5' to the PAM can also be used in the subject methods and kits. Adapters (such as those used in the working examples below, see FIG. 9A and FIG. 9B) can be modified to compensate. For example, BssKI (with a recognition site of N/CCNGG) and PspGI (with a recognition site of N/CCWGG) can be used as PAM-recognition DNA endonucleases if a "CC" were included at the 5' terminus of the first adapter, which would replace the "lost" CC (lost from the target DNA during cleavage). Without compensating to include the "CC", the cleavage fragments would not contain guide sequences because the cleavage fragments would not include sequences that were adjacent to PAMs in the intact starting material (e.g., intact chromosomal DNA).

As discussed above, some non-*S. pyogenes* Cas9 orthologs use PAMs other than NRG. Most other species' PAMs are 4-5 nucleotides in length and are thus not as frequently found in a given target DNA (e.g., genome). There are also likely to be fewer restriction enzymes (PAM-recognition DNA endonucleases) that cut within them. It is also conceivable that Cas9 derivatives will be engineered that require different PAMs, or no PAM at all. Thus, one or more PAM-recognition DNA endonucleases that are selected for a method, composition, or kit described herein can depend on the type of guide RNA desired, and need not be limited to the recognition of a particular PAM sequence. Moreover, selecting PAMs using restriction enzymes may not always be necessary for implementing the general techniques described herein.

Distal Cleaving DNA Endonucleases

Once a library of cleavage fragments are generated (e.g., via contacting a target DNA with one or more PAM-recognition DNA endonucleases), a distal cleaving DNA endonuclease can be used to cleave the cleavage fragments further, reducing (trimming) them to a desired length (e.g., the desired length of a guide sequence). In order to achieve trimming to a desired length, a recognition site (a DNA that includes a recognition sequence) is added to the cleavage fragments (via attachment to a first DNA adapter), where the recognition site is recognized by a distal cleaving DNA endonuclease.

A subject "distal cleaving DNA endonuclease" is a DNA endonuclease that cleaves at a distance of from its recognition sequence, and many such DNA endonucleases are known in the art. Because the goal of using a distal cleaving DNA endonuclease in the subject methods is to generate guide sequences of a guide RNA (by trimming the cleavage fragments generated by the one or more PAM-recognition DNA endonucleases), the distance of cleavage (from its recognition sequence) can be coordinated with the positioning of the recognition sequence within the first DNA adapter (described elsewhere herein). For example, if one desires a guide sequence of 15 nucleotides, then a distal cleaving DNA endonuclease can be used that cleaves at a distance of 15 nucleotides from the recognition sequence if the recognition sequence is positioned at the end of first DNA adapter. If, for example, the recognition sequence was instead embedded 5 nucleotides into the DNA adapter, then the cleavage would occur 10 nucleotides into the cleavage fragment.

As an illustrative example, if a 17 nucleotide guide sequence is desired, a distal cleaving DNA endonuclease that cleaves at a distance of 17 nucleotides (from the recognition sequence) can be used when the first DNA adapter includes the recognition sequence at the end of the adapter. Alternatively, a distal cleaving DNA endonuclease that cleaves at a distance of 18 nucleotides (from the recognition sequence) can be used if the recognition sequence is embedded by 1 nucleotide into the first DNA adapter. As another example, a distal cleaving DNA endonuclease that cleaves at a distance of 22 nucleotides (from the recognition sequence) can be used if the recognition sequence is embedded 5 nucleotides into the first DNA adapter.

Thus, in some cases, a distal cleaving DNA endonuclease of the subject methods, compositions and/or kits, is one that cleaves at a distance in the range of from of 10 to 50 nucleotides (nt) (e.g., from 10 to 40 nt, from 10 to 30 nt, from 10 to 25 nt, from 10 to 23 nt, from 15 to 50 nt, from 15 to 40 nt, from 15 to 30 nt, from 15 to 25 nt, from 15 to 23 nt, from 17 to 50 nt, from 17 to 40 nt, from 17 to 30 nt, from 17 to 25 nt, from 17 to 23 nt, from 20 to 50 nt, from 20 to 40 nt, from 20 to 30 nt, from 20 to 25 nt, from 20 to 23 nt) from its recognition site (recognition sequence) (the sequence to which the distal cleaving DNA endonuclease specifically binds). In some cases, a distal cleaving DNA endonuclease of the subject methods, compositions and/or kits, is one that cleaves at a distance in the range of from 17 to 40 nt (e.g., from 17 to 30 nt, from 17 to 25 nt, from 17 to 23 nt) from its recognition site.

In some cases, a subject distal cleaving DNA endonuclease is a type II DNA endonuclease (type II restriction enzyme) (e.g., see Morgan et al, Nucleic Acids Res. 2009 August; 37(15):5208-21). In some cases, a subject distal cleaving DNA endonuclease is a type IIG DNA endonuclease (type IIG restriction enzyme). Suitable examples of distal cleaving DNA endonucleases include but are not limited to (where the recognition site for each is followed by the cleavage distance):

| | | |
|---|---|---|
| ApyPI | ATCGAC | (20/18) |
| AquII | GCCGNAC | (20/18) |
| AquIII | GAGGAG | (20/18) |
| AquIV | GRGGAAG | (20/18) |
| CdpI | GCGGAG | (20/18) |
| CstMI | AAGGAG | (20/18) |
| DraRI | CAAGNAC | (20/18) |
| DrdIV | TACGAC | (20/18) |
| MaqI | CRTTGAC | (20/18) |
| MmeI | TCCRAC | (20/18) |
| NhaXI | CAAGRAG | (20/18) |

| | -continued | |
|---|---|---|
| NlaCI | CATCAC | (19/17) |
| NmeAIII | GCCGAG | (21/19) |
| PlaDI | CATCAG | (21/19) |
| PspOMII | CGCCCAR | (20/18) |
| PspPRI | CCYCAG | (21/19) |
| RceI | CATCGAC | (20/18) |
| RpaB5I | CGRGGAC | (20/18) |
| SdeAI | CAGRAG | (21/19) |
| SpoDI | GCGGRAG | (20/18) |
| BsbI | CAACAC | (21/19) |

In some cases, a subject distal cleaving DNA endonuclease is selected from the group consisting of: ApyPI, AquII, AquIII, AquIV, CdpI, CstMI, DraRI, DrdIV, MaqI, MmeI, NhaXI, NlaCI, NmeAIII, PlaDI, PspOMII, PspPRI, RceI, RpaB5I, SdeAI, SpoDI, and BsbI. In some cases, a subject distal cleaving DNA endonuclease is MmeI.

In some cases, a PAM-recognition DNA endonuclease can be a distal cleaving DNA endonuclease (described elsewhere herein). For example a first DNA adapter may not be necessary for including a recognition sequence for a distal cleaving DNA endonuclease if the one or more PAM-recognition DNA endonucleases used are themselves distal cleaving DNA endonucleases. For example, the enzyme CchIII has the recognition site of NN/NNNNNNNNNNNNNNNNNNCTTGGG (where "/" indicates the point of cleavage). Thus, such an enzyme could be used to generate guide sequences directly from target DNA without the need for a DNA adapter and/or without needing to contact the cleavage fragments with a distal cleaving DNA endonuclease other than the one that is both a PAM-recognition DNA endonuclease and a distal cleaving DNA endonuclease. In some cases, such a DNA endonuclease is a type IIS DNA endonuclease.

Adapter Removal DNA Endonucleases

An "adapter removal DNA endonuclease" as used herein can be any DNA endonuclease that is used to remove all or a portion of the first DNA adapter once the guide sequence library had been generated (e.g., after cleavage with a distal cleaving DNA endonuclease). Once a DNA adapter is added to the cleavage fragments (e.g., after cleaving with a PAM-recognition DNA endonuclease), the goal is to eventually attach to the guide sequences a DNA encoding a constant region of a guide RNA (e.g., constant region of a Cas9 targeter RNA, of a Cas sgRNA, etc.). In some cases, in order to do so, all or a portion of the first DNA adapter must be removed (e.g., see FIG. 8A and FIG. 8B, and the associated example adapters of FIG. 9A and FIG. 9B for example scenarios). In some cases, to allow for this, the first DNA adapter includes a recognition sequence for an adapter removal DNA endonuclease. However, in some embodiments, because the first DNA adapter also includes a first recognition site for a distal cleaving DNA endonuclease, the second recognition site (the site for the adapter removal DNA endonuclease) is for a DNA endonuclease that cleaves outside of the second recognition sequence.

Thus, like a distal cleaving DNA endonuclease, an adapter removal DNA endonuclease is often one that cleaves outside of its own recognition sequence. Thus, in some cases, a suitable adapter removal DNA endonuclease is any DNA endonuclease that cleaves outside of its own recognition sequence. In some cases, the adapter removal DNA endonuclease is BsaXI.

In some cases, an adapter removal DNA endonuclease of the subject methods, compositions, and/or kits, is one that cleaves at a distance in the range of from of 1 to 40 nucleotides (nt) (e.g., from 1 to 30 nt, from 1 to 25 nt, from 1 to 20 nt, from 1 to 15 nt, from 1 to 12 nt, from 1 to 10 nt, from 1 to 8 nt, from 1 to 5 nt, from 2 to 40 nt, from 2 to 30 nt, from 2 to 25 nt, from 2 to 20 nt, from 2 to 15 nt, from 2 to 12 nt, from 2 to 10 nt, from 2 to 8 nt, from 2 to 5 nt, from 3 to 40 nt, from 3 to 30 nt, from 3 to 25 nt, from 3 to 20 nt, from 3 to 15 nt, from 3 to 12 nt, from 3 to 10 nt, from 3 to 8 nt, from 3 to 5 nt) from its recognition site (recognition sequence) (the sequence to which the adapter removal DNA endonuclease specifically binds). In some cases, an adapter removal DNA endonuclease of the subject methods, compositions, and/or kits, is one that cleaves at a distance in the range of from 1 to 15 nt (e.g., from 2 to 15 nt, from 3 to 15 nt, from 3 to 12 nt, from 3 to 10 nt, from 3 to 8 nt, from 1 to 12 nt, from 1 to 10 nt, from 1 to 8 nt, from 1 to 5 nt) from its recognition site.

In some cases, the recognition sequence (adapter removal DNA endonuclease) is positioned within the first DNA adapter such that the adapter removal DNA endonuclease (e.g., the second DNA endonuclease) will cleave within or immediately adjacent to the first recognition sequence (the recognition sequence for the first DNA endonuclease, the distal cleaving DNA endonuclease). Thus, in some cases, an adapter removal DNA endonuclease specifically binds to a recognition sequence present in a DNA adapter and cleaves at one or more sites to remove all or a portion of the DNA adapter from the target DNA fragments to which it is bound.

See the examples below as well as FIGS. 8A-8B and FIGS. 9A-9B for non-limiting examples.

DNA Adapters/Linkers

The terms "DNA adapter" and "DNA linker" are used interchangeably herein to mean a DNA molecule used during a subject method for the production of a subject composition (e.g., a library of DNA molecules encoding guide RNAs). The terms are meant to encompass relatively short DNA molecules. The terms are used herein to refer to DNA molecules (e.g., Adapter 1, Adapter 2, Adapter 3, a DNA linker, etc.) having a length of from 5 to 300 base pairs (bp) in length (e.g., from 5 to 250 bp, from 5 to 225 bp, from 5 to 200 bp, from 5 to 180 bp, from 5 to 150 bp, from 10 to 300 bp, from 10 to 300 bp, from 10 to 250 bp, from 10 to 225 bp, from 10 to 200 bp, from 10 to 180 bp, from 10 to 150 bp, from 15 to 300 bp, from 15 to 250 bp, from 15 to 225 bp, from 15 to 200 bp, from 15 to 180 bp, from 15 to 150 bp, from 20 to 300 bp, from 20 to 300 bp, from 20 to 250 bp, from 20 to 225 bp, from 20 to 200 bp, from 20 to 180 bp, from 20 to 150 bp, from 25 to 300 bp, from 25 to 250 bp, from 25 to 225 bp, from 25 to 200 bp, from 25 to 180 bp, from 25 to 150 bp, from 30 to 300 bp, from 30 to 250 bp, from 30 to 225 bp, from 30 to 200 bp, from 30 to 180 bp, or from 30 to 150 bp in length).

However, a nucleic acid can be said to include (comprise) a subject DNA adapter. Such nucleic acids can therefore be longer than the adapter itself. For example, a vector can be said to include (comprise) a subject DNA adapter and/or DNA linker. In some cases, subject methods or kits refer to two DNA oligonucleotides that hybridize to form a given DNA linker or DNA adapter.

As an example, a nucleic acid that includes (comprises) a first DNA adapter (described in further detail below) can be a vector (e.g., a linearized vector, circular vector, viral vector, plasmid vector, etc.) that includes sequences that will facilitate the subject methods. For example, the protocol illustrated in FIG. 8B can be accomplished by including the sequences of Adapter 1 in a vector (e.g., viral vector, plasmid vector, linearized plasmid vector) such that the end product is a library of DNA molecules that encode guide RNAs where the DNAs molecules are vectors (e.g., circular vectors, linear vectors, viral vectors, plasmid vectors, linearized plasmid vectors, etc.). For example, a vector can be used that includes Adapter 1, where the vector includes the sequences of adapter 1 on one end of the vector (and optionally the sequences of Adapter 2 on the other end of the vector). This would allow for the entire protocol to be carried out using only one DNA adapter (e.g., a single plasmid and/or viral vector could be provided).

In some cases, an adapter can include a recognition sequence that is recognized by a DNA endonuclease so that self-ligated adapters (e.g., present in tandem) can be removed. To decrease the chance that such an endonuclease would cleave within the target DNA to which the adapter is attached, the recognition site used can be one that is recognized by a rare cutting endonuclease (e.g., a DNA endonuclease that recognizes a recognition sequence that is 7 base pairs or greater, 8 base pairs or greater, 9 base pairs or greater, etc.).

In some cases, the recognition site used so that self-ligated adapters (e.g., present in tandem) can be removed, can be a recognition sequence that is recognized by a PAM-recognition DNA endonuclease (e.g., the one or more PAM-recognition DNA endonucleases used to cleave the target DNA). This would reduce the chance of cleaving the target DNA to which the adapter is attached to nearly zero because if the target DNA contains such a site, it should have been cleaved during the initial cleavage (e.g., during cleavage with the one or more PAM-recognition DNA endonucleases). Thus, in some cases, a subject adapter (e.g., Adapter 1, Adapter 2, Adapter 3, a DNA linker, etc.) can include a recognition sequence that is recognized by a PAM-recognition DNA endonuclease (e.g., the recognition sequence can include a PAM sequence, e.g., a Cas9 PAM sequence). In some cases, an adapter (e.g., Adapter 1, Adapter 2, Adapter 3, a DNA linker, etc.) can include a recognition sequence that is recognized by the same PAM-recognition DNA endonuclease(s) used in the first step. Thus, in some cases, the first adapter includes a recognition sequence (e.g., one that includes a PAM sequence) that is recognized and cleaved by a PAM-recognition DNA endonuclease (e.g., see FIG. 9A). In some cases, a subject method includes a of step contacting an adapter-attached DNA molecule (e.g., adapter attached cleavage fragments) with a PAM-recognition DNA endonuclease.

In some cases, a subject adapter (e.g., Adapter 1, Adapter 2, Adapter 3, a DNA linker, etc.) can include a recognition sequence that is recognized by a rare cutting endonuclease (e.g., a DNA endonuclease that recognizes a recognition sequence that is 7 base pairs or greater, 8 base pairs or greater, 9 base pairs or greater, etc.). In some cases, a subject method includes a step of contacting an adapter-attached DNA molecule (e.g., adapter attached cleavage fragments) with a rare cutting endonuclease (e.g., a DNA endonuclease that recognizes a recognition sequence that is 7 base pairs or greater, 8 base pairs or greater, 9 base pairs or greater, etc.).

First DNA Adapter (Adapter 1)

In some cases, a first DNA adapter includes (i) a first recognition sequence for a first DNA endonuclease (Distal cleaving DNA endonuclease) that cleaves at a cleavage site outside of the first recognition sequence, wherein the first recognition sequence is positioned within the first DNA adapter such that said first DNA endonuclease will specifically bind to the first recognition sequence and will cleave at a site within a target DNA sequence that is attached to the first DNA adapter; and (ii) a second recognition sequence for a second DNA endonuclease (an adapter removal DNA endonuclease) that cleaves at a cleavage site outside of the second recognition sequence, wherein the second recognition sequence is positioned within the first DNA adapter such that said second DNA endonuclease will cleave within or immediately adjacent to the first recognition sequence. In some cases, the first DNA adapter includes a nucleotide sequence encoding a constant region of a Cas9 sgRNA or a Cas9 targeter RNA. In some cases, a vector that includes the first DNA adapter such that the first DNA adapter is present as part of the vector.

In some cases, the first recognition sequence is a recognition sequence for any of the distal cleaving DNA endonucleases described elsewhere herein. For example, in some cases, the first recognition sequence is a recognition sequence for one or more DNA endonucleases selected from the group consisting of: MmeI, NmeAIII, and BsbI. In some cases, the first recognition sequence is a recognition sequence for MmeI.

The second recognition sequence is a recognition sequence for any of the adapter removal DNA endonucleases described elsewhere herein. For example, in some cases, the first recognition sequence is a recognition sequence for BsaXI.

Second DNA Adapter (Adapter 2)

In some cases, a first DNA adapter includes one or more of: (a) an RNA polymerase promoter (e.g., any desired promoter such as a T7 promoter), (b) a recognition sequence that facilitates cloning (e.g., any recognition site that allows the attached DNA to be ligated into a vector), and (c) an overhang (e.g, any overhand that allows the attached DNA to be ligated into a vector). The Examples section below as well as FIG. 8A, FIG. 8B, FIG. 9A, and FIG. 9B provide illustrative examples of a second DNA adapter and elements that can be included.

Blunting

In some cases, a subject method includes a step of blunting. Such a step will be known to one of ordinary skill in the art and any convenient method of blunting can be used. For example, a nuclease (e.g., mung bean nuclease) can be used to remove the single stranded portion of sticky ends generated by the subject DNA endonucleases.

Degeneracy

In some cases, one or more of the DNA endonucleases used herein will generate a sticky end, that will be present after cleavage. In order to attach an adapter to a population of DNA molecules (e.g., cleavage fragments) having sticky ends, where the bases that are part of the sticky ends are not predictable (e.g., when the endonuclease cuts at a site that is a predictable number of nucleotides from its recognition sequence, but the sequence at the actual cleavage site is not predictable), an adapter can include a corresponding overhang having a corresponding number of "n" nucleotides. For example, if each cleavage fragment of a population of cleavage fragments has an undefined (variable) 2 base pair 5' overhang, an appropriate adapter (to be attached at the overhang site) can have a 2 nucleotide 5' overhang where the overhang nucleotides are both "n." In such a cases, the adapter is referred to as if it were a single molecule, but the adapter but is really a population of adapters where the nn nucleotides vary from individual adapter to individual adapter within the population. Thus, an adapter can have one or more "n" nucleotides (e.g., nn nucleotides) such that the population of adapters includes adapters of all possible base combinations at the "n" nucleotides. This is also referred to in the art as degeneracy. Thus, a subject adapter can have degeneracy at particular nucleotides (e.g., those indicated by an "n").

In some cases a subject method includes a step of amplifying (e.g., via PCR) the library of DNA molecules encoding Cas9 sgRNAs or Cas9 targeter RNAs. In some cases, the library of DNA molecules that are produced by the subject methods (encoding Cas9 targeter RNAs or Cas9 sgRNAs) can be inserted into vectors (e.g., directly or via amplification by PCR, e.g., using primers that incorporate restriction sites to allow for cleavage and cloning into a vector such as a viral vector or plasmid).

Generating Guide RNAs

In some cases, the method includes a step of contacting the library of DNA molecules encoding Cas9 sgRNAs or Cas9 targeter RNAs (or an amplified library) with an RNA polymerase (e.g., T7 RNA polymerase) to generate a library of Cas9 sgRNAs or a library of Cas9 targeter RNAs. For example, if the DNA Linker is a vector, then the library of DNA molecules encoding Cas9 sgRNAs or Cas9 targeter RNAs can be a library of vectors (e.g., viral vectors, plasmid vectors, etc.). In some cases, the individual DNA molecules (e.g., vectors) from the library can be isolated (e.g., by transfecting/transforming cells with the library and selecting individual colonies/cells) from one another. For example, such a library can be separated into individual wells of multi-well plates (as bacterial colonies, viral vectors, plasmids, eukaryotic cell clones, etc.).

Non-Cas9 CRISPR/Cas Systems and Guide RNAs

As will be readily appreciated by one of ordinary skill in the art, the compositions (e.g., including kits) and methods provided in this disclosure are not limited to guide RNAs from Cas9 CRISPR/Cas systems (i.e., type II CRISPR/Cas systems). For example, the compositions and methods described herein can be used to generate a library of DNA molecules encoding CRISPR/Cas guide RNAs from any CRISPR/Cas system (e.g., type I and/or type III systems). The compositions and methods described herein can be used to generate a library of DNA molecules encoding any desired guide RNA with any desired length of guide sequence, where the guide sequence is located in the target DNA adjacent to a PAM sequence (e.g., by (i) choosing appropriate PAM-recognition DNA endonuclease(s); (ii) choosing a distal-cleaving DNA endonuclease that cleaves at the desired distance from its recognition sequence relative to the position of the recognition sequence in the first DNA adapter; and (iii) using a DNA encoding a constant region of the desired guide RNA).

For example, in some cases, a subject composition (e.g., kit) and/or method is for generating a library of DNA molecules encoding CRISPR/Cas guide RNAs (e.g., a library of DNA molecules encoding guide RNAs of a type I system, a library of DNA molecules encoding guide RNAs of a type II system, a library of DNA molecules encoding guide RNAs of a type III system, and the like).

Kits

The present disclosure provides kits that include various combinations of components useful in performing the subject methods. Components of a subject kit can be in present in the same or separate containers. For example, in some cases, the components can be combined in a single container. Any of the kits described herein can include one or more additional reagents, where such additional reagents can be selected from: a dilution buffer; a reconstitution solution; a wash buffer; a control reagent; a control expression vector or RNA or DNA polynucleotide; a reagent for in vitro production of a subject variant Cas9 protein from DNA or RNA, and the like.

In some cases, a subject kit for generating a library of DNA molecules encoding guide RNAs (e.g., Cas9 single guide RNAs (sgRNAs), Cas9 targeter RNAs, etc.) includes (a) a first DNA adapter, two DNA oligonucleotides that hybridize to form said first DNA adapter, or a nucleic acid comprising said first DNA adapter, wherein the first DNA adapter includes: (i) a first recognition sequence for a first DNA endonuclease that cleaves at a cleavage site outside of the first recognition sequence, wherein the first recognition sequence is positioned within the first DNA adapter such that said first DNA endonuclease will specifically bind to the first recognition sequence and will cleave at a site within a target DNA sequence that is attached to the first DNA adapter; and (ii) a second recognition sequence for a second DNA endonuclease that cleaves at a cleavage site outside of the second recognition sequence, wherein the second recognition sequence is positioned within the first DNA adapter such that said second DNA endonuclease will cleave within or immediately adjacent to the first recognition sequence. In some cases, the first DNA adapter comprises a nucleotide sequence encoding a constant region of a Cas9 sgRNA or a Cas9 targeter RNA. In some cases, the kit includes a vector that includes the first DNA adapter.

In some cases, the kit includes at least one of: (i) a DNA linker, (ii) two DNA oligonucleotides that hybridize to form said DNA linker, and (iii) a nucleic acid comprising said DNA linker; wherein the DNA linker comprises a nucleotide sequence encoding a constant region of a Cas9 targeter RNA or a Cas9 sgRNA. In some cases, the kit includes a vector that includes the DNA linker. In some cases, the kit includes at least one of: (i) a second DNA adapter, (ii) two DNA oligonucleotides that hybridize to form said second DNA adapter, and (iii) a nucleic acid comprising said second DNA adapter; wherein the second DNA adapter comprises one or more of: (a) an RNA polymerase promoter, (b) a recognition sequence that facilitates cloning, and (c) an overhang. In some cases, the kit includes a vector that includes the second DNA adapter.

In some cases, the kit includes a nucleic acid that includes the first and second DNA adapters, wherein (i) the nucleic acid is linear and the first and second DNA adapters are positioned on opposite ends of the nucleic acid, or (ii) the nucleic acid is circular and the first and second DNA adapters are positioned adjacent to one another such that cleavage between the first and second DNA adapters will produce a linear nucleic acid in which the first and second DNA adapters are positioned on opposite ends. In some cases, the nucleic acid that includes the first and second DNA adapters is a vector. In some cases, the vector is a viral vector or a plasmid vector.

In some cases, a subject kit includes a blunting nuclease that removes single stranded DNA overhangs. In some cases, the blunting nuclease is mung bean nuclease.

In some cases, the first and/or second DNA adapter includes a recognition sequence that can be specifically bound and cleaved by a PAM-recognition DNA endonuclease. In some cases, the first recognition sequence is a recognition sequence for one or more DNA endonucleases selected from the group consisting of: MmeI, NmeAIII, and BsbI. In some cases, the first recognition sequence is a recognition sequence for MmeI. In some cases, the second recognition sequence is a recognition sequence for BsaXI.

In some cases, a subject kit includes one or both of: (i) the first DNA endonuclease, and (ii) the second DNA endonuclease. In some cases, the first DNA endonuclease cleaves at a cleavage site that is 17 to 30 nucleotides from the first recognition sequence. In some cases, the first DNA endonuclease is selected from the group consisting of: MmeI, NmeAIII, and BsbI. In some cases, the first DNA endonuclease is MmeI. In some cases, the second DNA endonuclease cleaves at a cleavage site that is 1 to 20 nucleotides from the second recognition sequence. In some cases, the second DNA endonuclease is BsaXI.

In some cases, a subject kit includes one or more PAM-recognition DNA endonucleases that each specifically binds to and cleaves within a recognition sequence that includes a Cas9 PAM sequence. In some cases, a subject kit includes two or more PAM-recognition DNA endonucleases that each specifically binds to and cleaves within a recognition sequence that includes a Cas9 PAM sequence. In some cases, a subject kit includes three or more PAM-recognition DNA endonucleases that each specifically binds to and cleaves within a recognition sequence that includes a Cas9 PAM sequence. In some cases, a kit includes the PAM-recognition DNA endonucleases BfaI, HpaII, and ScrFI. In some cases, the PAM-recognition DNA endonucleases are selected from the group consisting of: BfaI, HpaII, ScrFI, MspI, BstNI, NciI, BsiSI, HapII, MaeI, XspI, AsuC2I, BcnI, BpuMI, CauII, BciT130I, BptI, BseBI, BsiLI, Bst2UI, BstOI, MvaI, Bme1390I, BmrFI, and MspR9I.

In addition to above-mentioned components, a subject kit can further include instructions for using the components of the kit to practice the subject methods. The instructions for practicing the subject methods are generally recorded on a suitable recording medium. For example, the instructions may be printed on a substrate, such as paper or plastic, etc. As such, the instructions may be present in the kits as a package insert, in the labeling of the container of the kit or components thereof (i.e., associated with the packaging or subpackaging) etc. In other embodiments, the instructions are present as an electronic storage data file present on a suitable computer readable storage medium, e.g. CD-ROM, diskette, flash drive, etc. In yet other embodiments, the actual instructions are not present in the kit, but means for obtaining the instructions from a remote source, e.g. via the internet, are provided. An example of this embodiment is a kit that includes a web address where the instructions can be viewed and/or from which the instructions can be downloaded. As with the instructions, this means for obtaining the instructions is recorded on a suitable substrate.

Utility

There are several utilities of any of the libraries generated using the methods described herein. For example, the subject methods, kits, and compositions facilitate the production and/or isolation of guide RNAs that target DNA for which no DNA sequence is available. In such cases, guide RNAs can be produced that target nearly every available target site in DNA (e.g., a genome/exome of an uncharacterized organism), and this can be accomplished without having any sequence information whatsoever. The guide RNAs can be used to guide a CRISPR/Cas protein (e.g., Cas9) to sites within the genome with the purpose of cleaving at the target site (e.g., double strand break, single strand break), and perhaps causing a genetic mutation at that site. Such a library can be used to functionally screen an entire genome, or perhaps a particular region of the genome (e.g., a particular chromosome), depending on the starting DNA material used. Thus, the guide RNAs that can be generated from such libraries can be used separately (e.g., one at a time) for such screens (i.e., each cell or organism tested could have one, or perhaps a pool, of guide RNAs that were generated by the library). Once a particular "hit" (e.g., phenotype of interest) is identified, the DNA used to generate that particular guide RNA can be identified (e.g., via sequencing that DNA). Because so many guide RNAs can be generated using the subject methods, clusters of "hits" using guide RNAs that target the same gene may aid in the identification of the targeted gene.

In other cases, multiple guide RNAs can be used together in applications where the target DNA is not modified. For example, in some cases the CRISPR/Cas enzyme that is used (e.g., Cas9) is enzymatically inactive (e.g., dCas9) or is at least nuclease defective such that it does not cleave the target DNA. In such cases, the enzyme itself (e.g., dCas9) can be labeled (e.g., with a fluorescent protein such as neon, GFP, RFP, etc. as exemplified below), thus allowing visualization of the target DNA. For example, the starting material (target DNA) used can be from one or more chromosomes from a particular organism and the generated guide RNAs will thus allow for the visualization of that particular chromosome (e.g., in living cells). The utilities listed above represent just a small sample of the practical uses of libraries generated using the methods, compositions, and kits described herein.

EXAMPLES

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Celsius, and pressure is at or near atmospheric. Standard abbreviations may be used, e.g., bp, base pair(s); kb, kilobase(s); pl, picoliter(s); s or sec, second(s); min, minute(s); h or hr, hour(s); aa, amino acid(s); kb, kilobase(s); bp, base pair(s); nt, nucleotide(s); i.m., intramuscular(ly); i.p., intraperitoneal(ly); s.c., subcutaneous(ly); and the like.

Example: 1 Generation of a Library of DNA Molecules Encoding Cas9 Guide RNAs

Although it is theoretically possible to generate large numbers (e.g., many thousands) of guide RNAs, the complexity and cost of oligonucleotide synthesis makes this approach impractical for most laboratories. Similarly, genome-wide screening libraries are available for some well-studied organisms, but generation of such libraries by oligonucleotide synthesis approaches is unlikely to be cost-effective for many other organisms otherwise amenable to CRISPR-mediated screens, or for which genome data is not yet available.

The data here describe an approach for generating large numbers of diverse guide RNAs for studies using a CRISPR-based system (e.g., to label specific sequences on chromosomes, for screening a targeted mutagenesis library, etc.). Demonstrating the ability to generate a library of DNA molecules encoding Cas9 targeter RNAs or Cas9 single guide RNAs (sgRNAs) from an arbitrary source of DNA, the methods described herein were used to generate a Cas9 guide RNA library from: (i) *Xenopus* to use the CRISPR-Cas9 system to label chromosomes in egg extracts, and (ii) a prokaryotic genome.

Design

Figure 1B:
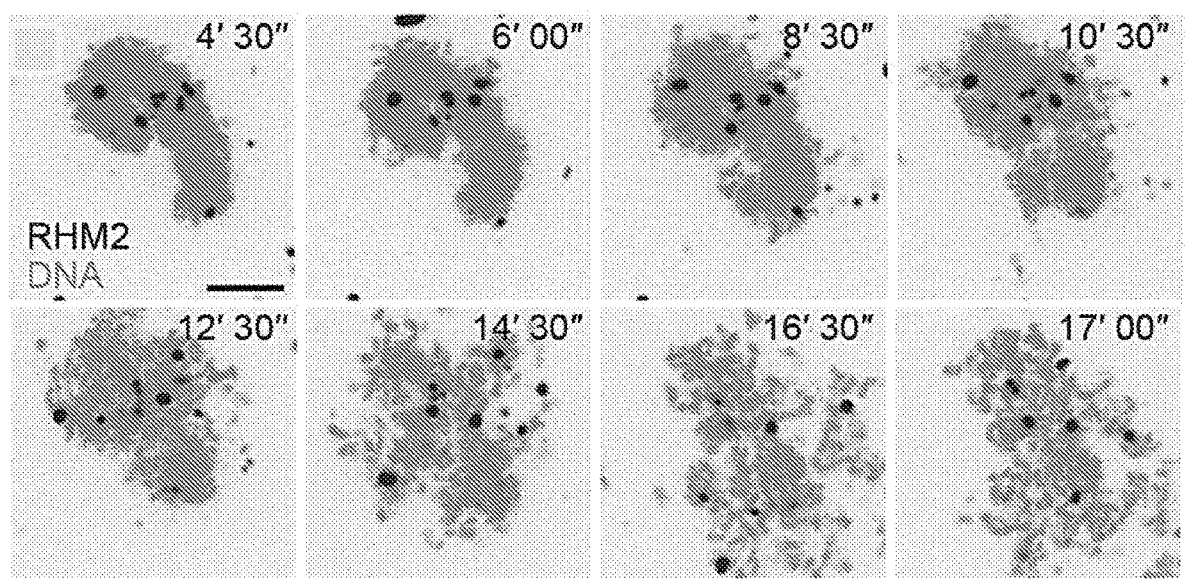
Figure 5:
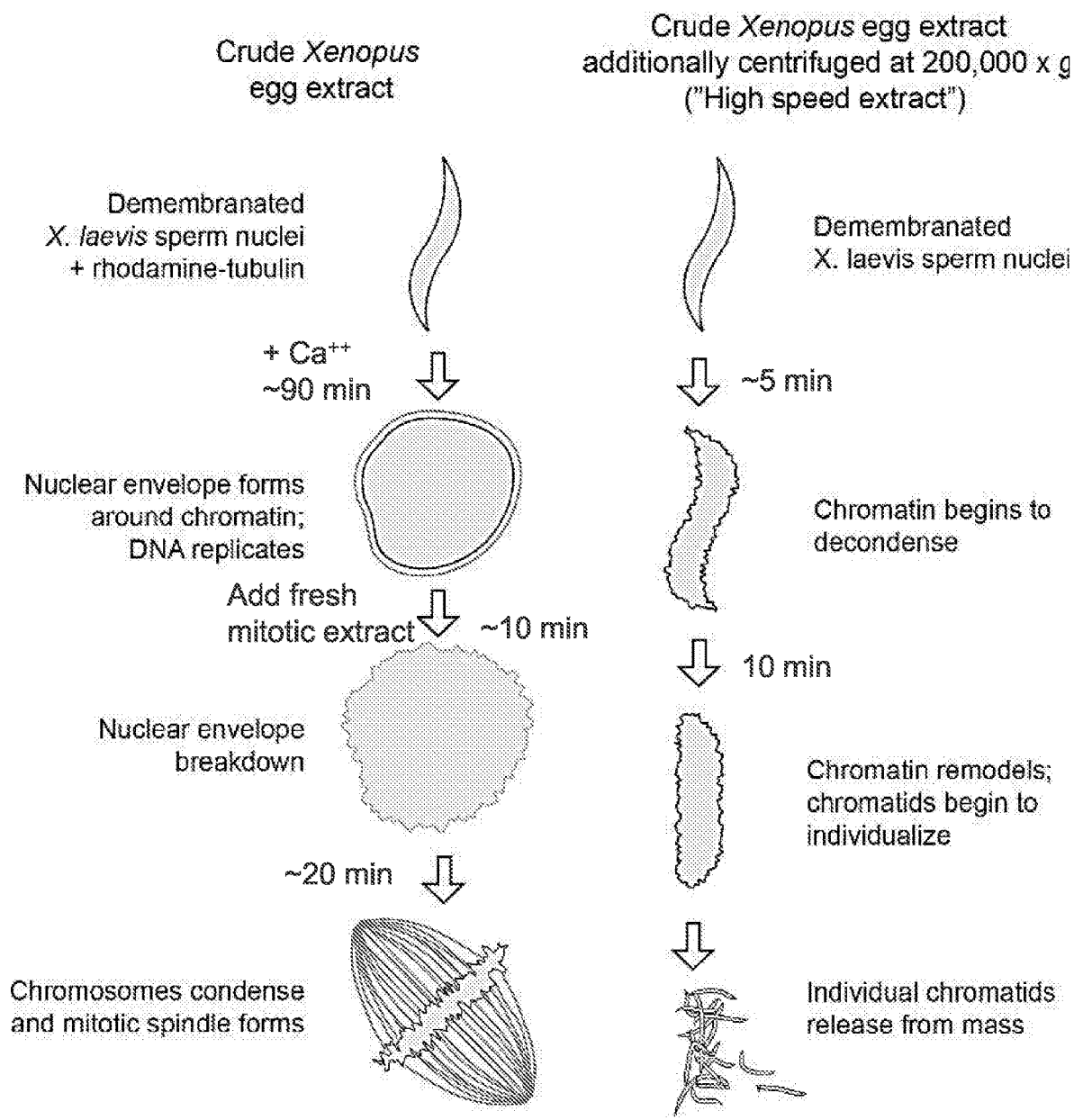
FIG. 5 presents a schematic of how *Xenopus* egg extract allows study of cell cycle chromosome events in vitro.
Figure 6:
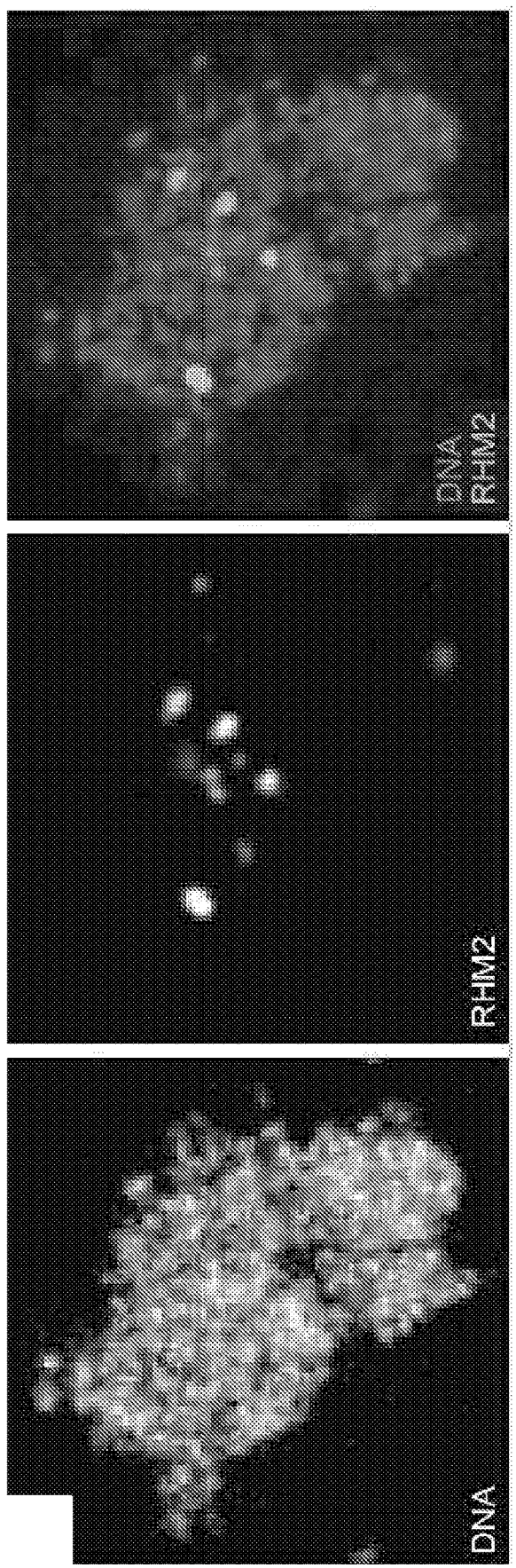
FIG. 6 presents data showing that repetitive genomic loci can be visualized using dCas9-Neon.

To label chromosomes in vitro, we expressed and purified recombinant nuclease deficient Cas9 (dCas9) fused to mNeonGreen, the brightest green/yellow fluorescent protein yet described (Shaner et al., 2013) (FIG. 1A). The dCas9-Neon protein was complexed with 7 sgRNAs designed against the RHM2 745 base pair (bp) multiple-locus tandem repeat, present at a mean of ~2000 copies near the centromere of most *Xenopus laevis* chromosomes (Freeman and Rayburn, 2005; Meyerhof et al., 1983) (Table 1, Table 2). A big advantage of using *Xenopus* extract is that it can be biochemically manipulated and the cell cycle state controlled (FIG. 5). We followed the dynamics of mitotic chromatid formation by time-lapse fluorescence microscopy by adding sperm nuclei to metaphase-arrested egg extract that has been ultracentrifuged to remove membranes. During this reaction, sperm chromatin remodels and individual chromatids resolve from one another. Upon addition of RHM2/dCas9-Neon probes, puncta formed in numbers in agreement with that expected from published in situ hybridization data (Freeman and Rayburn, 2005; Meyerhof et al., 1983); chromatids with distinct foci could be seen individualizing and separating from the chromosome mass within 10 minutes (FIG. 1B and FIG. 6). In crude extracts that support transit through the cell cycle, RHM2 labeling was maintained on mitotic chromosomes as the spindle formed, and probes were visible at the metaphase plate (FIG. 1C). Two other classes of repeat were labeled in the same way with patterns in agreement with published data (FIG. 1D) (Bassham et al., 1998; Hummel et al., 1984). Simultaneous dual-color labeling of two classes of repeats was also possible (FIG. 1E).

Figure 2A:
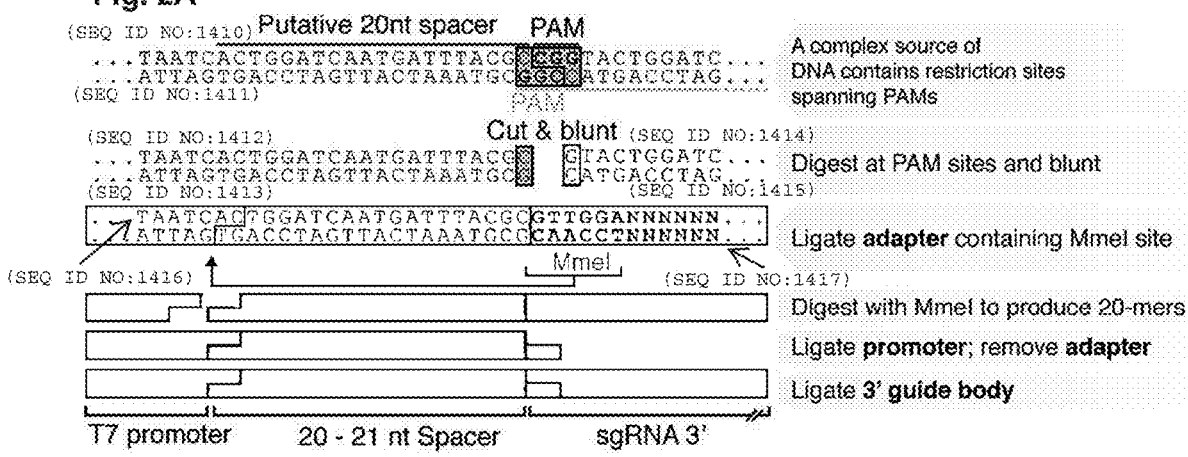
FIG. 2A-2B present data related to showing that a guide library generated according to the subject methods can program dCas9-Neon labeling of a repetitive locus.
Figure 2B:
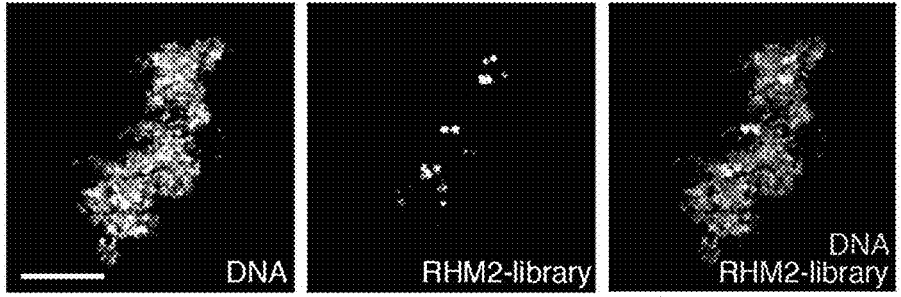

For labeling non-repetitive loci, we reasoned that potentially any DNA sequence could be enzymatically processed into a library of sgRNAs and used to tile along a chromosomal region. The constraints imposed by the *S. pyogenes* CRISPR system are that a targeted sequence must be approximately 20 nucleotides (nt) in length and immediately 5' to a "PAM", or protospacer adjacent motif consisting of an NAG or NGG triplet. We designed a strategy to extract PAM-proximal sequences by digesting input DNA with restriction enzymes targeting immediately 5' to an NGG or NAG (see details in Materials and Methods). The resulting fragments are ligated to an adapter containing a recognition site for the restriction enzyme MmeI, which cuts 20-21 nt 5'. Finally, we removed the adapter and ligated the resulting fragments to a 5' RNA polymerase promoter for in vitro transcription and a 93 nt 3' sgRNA Cas9 hairpin (FIG. 2A). We first evaluated the effectiveness of the digestion/ligation protocol in CRISPR imaging on the RHM2 repeat amplified by PCR and found that the probes gave similar labeling patterns as the traditionally designed guides (FIG. 2B, compare to FIG. 1B and FIG. 1D).

Figure 3A:
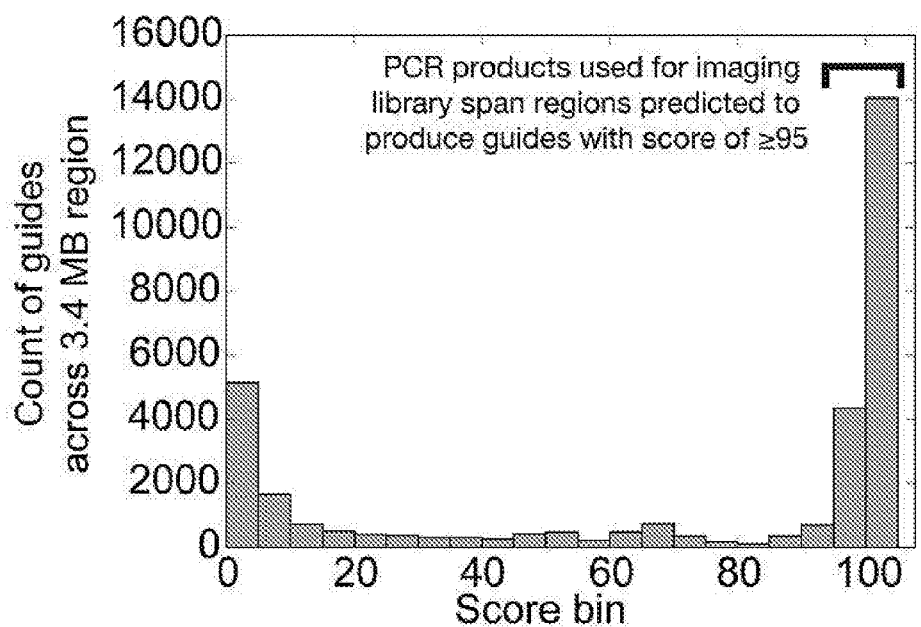
FIG. 3A-3C provides data related to showing that a single 3.4 MB locus can be labeled using an enzymatically generated guide library (Cas9 guide RNA library).

To label arbitrary, non-repetitive regions of the genome, we PCR-amplified specific subsequences within a 3.4 megabase (MB) region on chromosome 4 of the *X. laevis* genome. These subsequences represent 144 regions from 316 bp to 4088 bp in length that, when amplified, pooled and digested as described above are predicted to produce guides with minimal off-target effects (Table 3). The extent of off-target effects was predicted using a previously published scoring algorithm that determines the number and location of mismatches within guide target sequences when aligned to the entire genome (Hsu et al., 2013). A guide with no predicted off-target binding is scored as 100 in this scheme. We picked a threshold of 95, at which no perfect matches are found elsewhere in the genome and the closest matches differ at positions that would strongly impair guide recognition (FIG. 3A). We obtained 100 PCR products (see FIG. 7), which we expected to yield 1,276 guides when all products were pooled and subjected to the digestion/ligation library protocol. After enzymatically processing the PCR products as outlined above, the final pooled library was transcribed in vitro using T7 RNA polymerase (see detailed protocol in Supplemental Files).

TABLE 1

Features of *Xenopus* repetitive sequences targeted in FIG. 1A-1E and FIG. 6.

| Repeat name | GenBank ID | Location | Number of copies | Repeat unit length | Reference |
|---|---|---|---|---|---|
| Telomeres | | Chromosome ends | Total 10-50 kb/chromosome | 6 bp | 14 |
| RHM2/Satellite 1 | X00036 | Near centromeres of ~65% of chromosomes | 10,000-30,000 (1.35% of total DNA). Mean ~1,000-3000/locus. | 745 bp | 15, 16 |
| REM3 | X00680 | Reported as near centromere of chromosome 1 | 1,200 | 469 bp | 17 |

TABLE 2

Targeting sequences used to label repetitive *X. laevis* loci.

| Target | Sequence | SEQ ID NO: |
|---|---|---|
| Telomere | GGTTAGGGTTAGGGTTAGGGTT | 1107 |
| RHM2 #1 | GTAGAGTACGCTCTTGATTG | 1108 |
| RHM2 #2 | GATTCTGCCGAAAAGAAAGT | 1109 |
| RHM2 #3 | GGTGACTTTTCAGGTTTCTTTA | 1110 |
| RHM2 #4 | GGCTCTTTTAGGACTGGGCCTC | 1111 |
| RHM2 #5 | GGGAATCGAACCCACAACCTTT | 1112 |
| RHM2 #6 | GGACAGCCCCAGTTGGAAAAAG | 1113 |
| RHM2 #7 | GGCCTGAAGTAGAAGTACATAG | 1114 |
| REM3 #1 | GGAAAGGGTAGGGTTTCCCT | 1115 |
| REM3 #2 | GGTTACATGCTCAACCAAAG | 1116 |
| REM3 #3 | GGTCCATCATCCATCATAGC | 1117 |
| REM3 #4 | GGATGATATGCTTAACCAAC | 1118 |
| REM3 #5 | GGGGGTGGGTCCCTTTGTAG | 1119 |
| REM3 #6 | GGCCTTAATAGTCAATTGCT | 1120 |
| REM3 #7 | GGTTTAGAATTTGAATGTGA | 1121 |

The variable portion of sgRNAs generated by in vitro transcription (IVT) from DNA templates is shown.

FIG. 1A-1E. Repetitive genomic loci can be visualized using dCas9-Neon in *Xenopus* egg extracts. (FIG. 1A)

dCas9-Neon is programmed to label specific genomic loci by conjugation to an sgRNA molecule containing a complementary target sequence. See also FIG. 5. (FIG. 1B) dCas9-Neon programmed using RHM2 sgRNA (black) localizes rapidly to loci in sperm nuclei (Sytox Orange dye, magenta). Time (min) after imaging started is indicated in the top left of each image. See also Supplementary Movie 1 and FIG. 6. (FIG. 1C) Labeled RHM2 loci (green) are maintained following formation of a mitotic spindle (red). (FIG. 1D) Three examples of repeat classes labeled on sperm nuclei in *Xenopus* egg extract (1n=18). Left: RHM2 is a centromere-proximal locus on ~65% of chromosomes (Freeman and Rayburn, 2005). Middle: Telomere repeats target chromosome termini Right: REM3 is reported to target a single centromere-proximal locus on chromosome 1, appearing here as two spots (Hummel et al., 1984). (FIG. 1E) Left: Sperm nuclei driven into interphase in the presence of dCas9-tdTomato Telomere sgRNA and dCas9-Neon RHM2 sgRNA demonstrate simultaneous dual-color labeling (scale bar, 5 µm). Right: A subset of RHM2 and telomere loci appear to co-localize, while others do not (scale bars 10 µm, except magnification in FIG. 1E, 1 µm).

FIG. 2A-2B. An enzymatically generated guide library can program dCas9-Neon labeling of a repetitive locus. (FIG. 2A) Outline of enzymatic library generation approach. (FIG. 2B) dCas9-Neon programmed using an RHM2 repeat unit processed with this method localizes in a labeling pattern similar to that seen for RHM2 in FIG. 1B and FIG. 1D (scale bar, 5 µm).

Figure 3B:
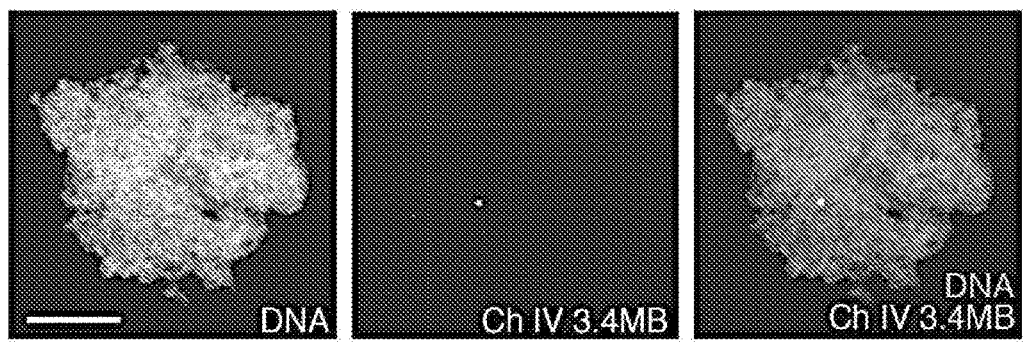
Figure 3C:
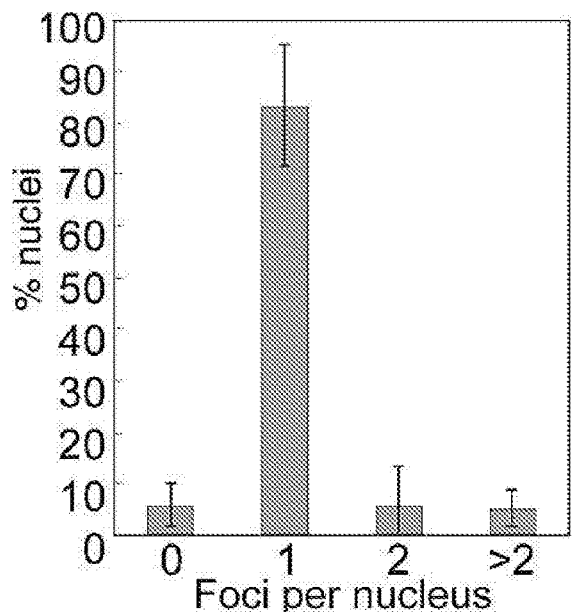

FIG. 3A-3C. A single 3.4 MB locus can be labeled using an enzymatically generated guide library. (FIG. 3A) Specificity score distribution for all guides predicted to be generated by subjecting 3.4 MB region to procedure outlined in FIG. 2A. Only sub-regions predicted to generate guides with a score of ≥95 were used as PCR templates for library construction. (FIG. 3B) Processing of 100 PCR products (See FIG. 7) spanning regions within a 3.4 MB region of *X. laevis* chromosome 4 generates a single labeled spot in haploid sperm nuclei (scale bar, 5 µm). (FIG. 3C) Count of fluorescent foci per sperm nucleus when incubated with 3.4 MB library. n=3 experiments, 11-13 nuclei scored per experiment. Bars are ±standard deviation. See also FIG. 7

FIG. 4A-4F. A complex guide library targeting sequences within the *E. coli* genome. (FIG. 4A) Comparison of theoretical maximum number of guides generated by *E. coli* genome digestion with guides identified by sequencing (black text) and of sequencing reads that represent expected guides versus those reads that do not correctly target *E. coli* PAM-adjacent 20mers (blue text). (FIG. 4B) Length distribution of variable spacers (region between T7 promoter and sgRNA guide body) in library as determined by high-throughput sequencing. (FIG. 4C) Distribution of abundance of unique guides within library. (FIG. 4D) Coverage of selected GO-term gene groups by library sgRNAs compared to the total number of genes annotated by those GO terms. (FIG. 4E) Analysis of genes targeted by guides in sequenced library as binned by gene length. (FIG. 4F) In silico analysis of guide specificity as predicted to be produced by digestion/ligation of *E. coli* genomic DNA. A score of 100 indicates no predicted off-target effects.

FIG. 5. *Xenopus* egg extract allows study of cell cycle chromosome events in vitro. Left: Sperm nuclei are cycled into interphase in crude extracts by the addition of calcium, which induces nuclear envelope formation and DNA replication. Interphase nuclei can then be driven into a mitotic state by adding additional mitotically-arrested extract. Right: Ultracentrifuged crude egg extract supports remodeling of sperm chromatin into individualized mitotic chromatids, but do not support mitotic spindle assembly.

FIG. 6. Repetitive genomic loci can be visualized using dCas9-Neon. Re-scaled and enlarged image from FIG. 1B (10 m 30 s timepoint) showing individual channels.

Figure 7:
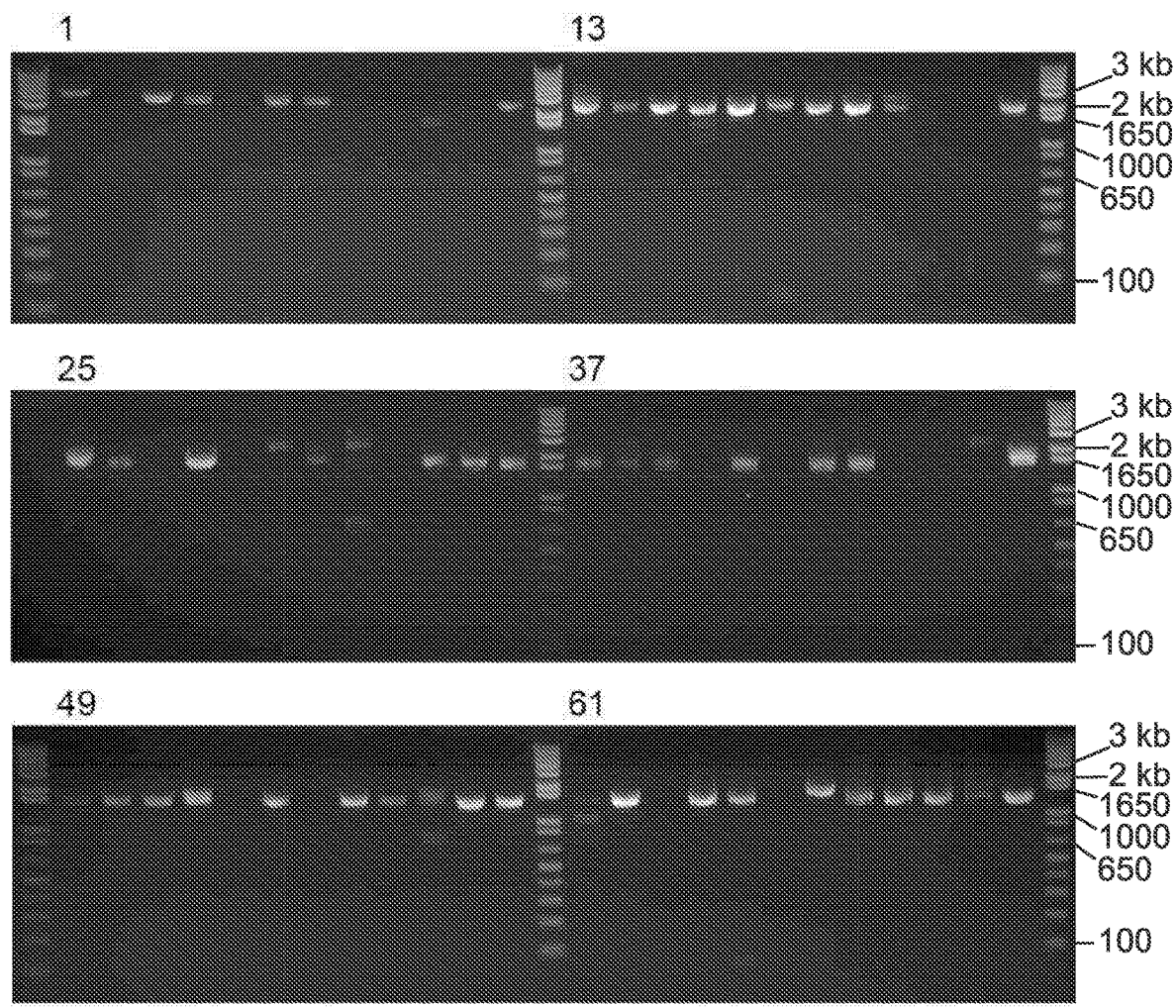
FIG. 7 presents PCR products related to construction of a subject library.
Figure 7:
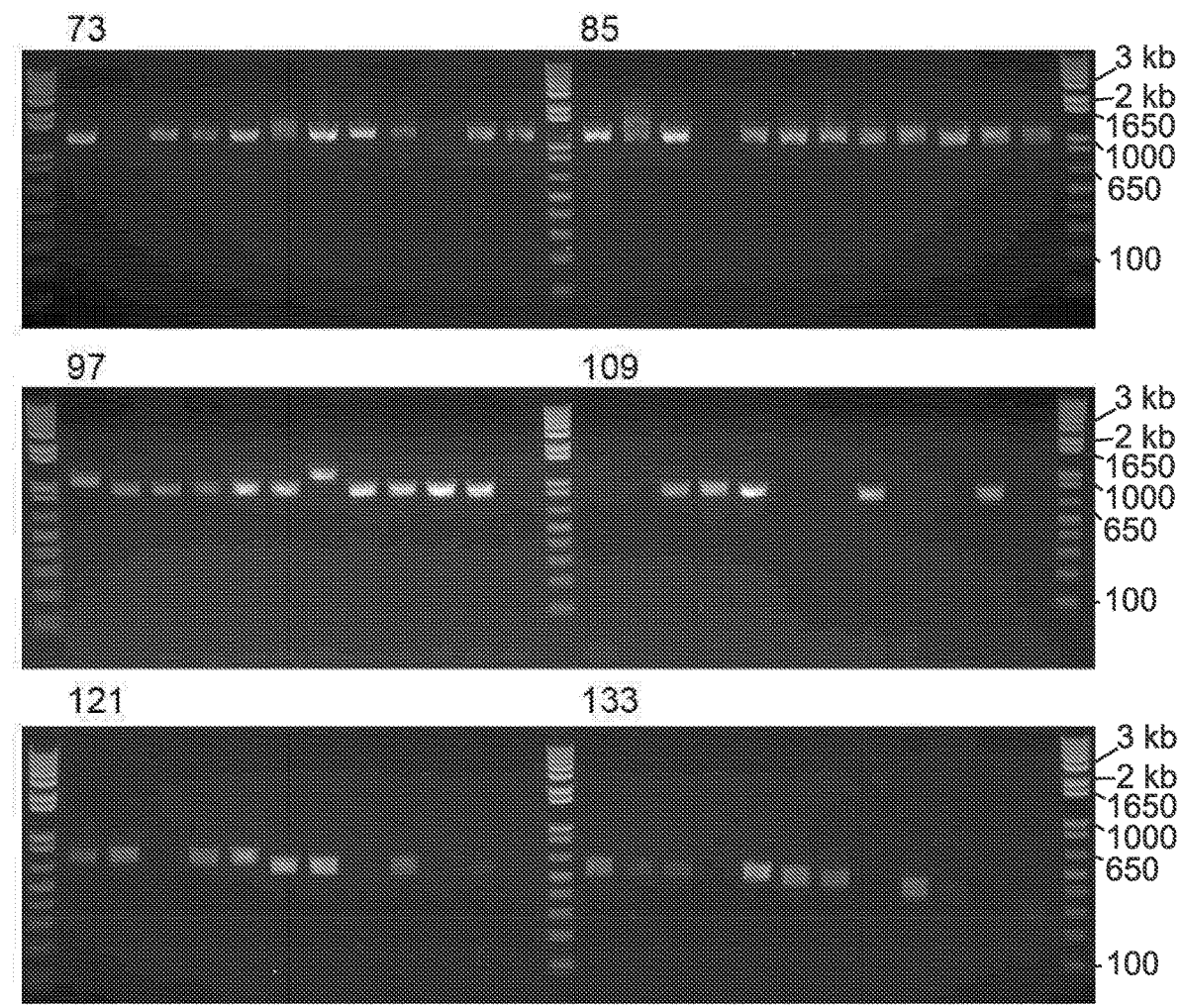

FIG. 7. DNA source for enzymatic construction of guide library used to label 3.4 MB region. 1% Agarose gels showing PCR products pooled and used in library assembly. Primers used to generate PCR products are shown in Table 3.

TABLE 3

PCR primers used for amplifying 3.4 MB region of X. laevis for locus labeling.

| | Amplicon position on Scaffold 102974 | Forward primer | Reverse primer | SEQ ID NO | Product length | Guides contained |
|---|---|---|---|---|---|---|
| 1 | 19100468 | AGGGGTGTCCAGAAGATT | AAAGACCAAAGAGGGAGG | 1122, 1266 | 4088 | 12 |
| 2 | 21447709 | TGGAACTATCAGCCCTGA | CGGGGAGAATAGTGGATT | 1123, 1267 | 3594 | 32 |
| 3 | 19991274 | GGTTCCGGTACCAGTGTGTATA | ATATTGGCACCGGGGACT | 1124, 1268 | 3230 | 23 |
| 4 | 18505915 | ACACTCGACCTGTCCTTATG | TAATTGAACCAGGCGTTG | 1125, 1269 | 2905 | 17 |
| 5 | 18663621 | TCTCATGTGTCTCCTTGC | GTTCTGCTAGTGACAGGTCT | 1126, 1270 | 2660 | 13 |
| 6 | 21065410 | GTAAATCGATTCTAAATTCGG | CAGATGTGGTAGACTTGTCTG | 1127, 1271 | 2638 | 10 |
| 7 | 18909500 | CAACCTGTGCCTAAATGC | TTTATGGCACTGACACCC | 1128, 1272 | 2612 | 12 |
| 8 | 19947076 | CCCCCTCTCTAATTACAGCT | AGTTTTACACCCGGATCC | 1129, 1273 | 2600 | 10 |
| 9 | 21221279 | CCCAACTTGGTCCTTAATAA | CAGCGTGCCTTTAAGAAC | 1130, 1274 | 2450 | 14 |
| 10 | 20078715 | ACTCGTCTGGCGCATTTC | GTCGCTGTTAAACCCCATGT | 1131, 1275 | 2444 | 10 |
| 11 | 18963570 | GGACTGTCTTTATCGGCA | TGGATCCTATGCCGTAAC | 1132, 1276 | 2442 | 10 |
| 12 | 20598378 | AGCAGGCTAGACAGACAG | CTTTGGACCCTACTCATG | 1133, 1277 | 2399 | 21 |

TABLE 3 -continued

PCR primers used for amplifying 3.4 MB region of *X. laevis* for locus labeling.

| | Amplicon position on Scaffold 102974 | Forward primer | Reverse primer | SEQ ID NO | Product length | Guides contained |
|---|---|---|---|---|---|---|
| 13 | 20331335 | TCTCCAGCGTGATCATTC | ATGCAGGATGCTAGTGAGAG | 1134, 1278 | 2336 | 15 |
| 14 | 20470442 | GCCTGTGATGTTGGAAAG | ATAATGGGGTTCTGAGGC | 1135, 1279 | 2334 | 14 |
| 15 | 21297377 | CTGCGATGGAAAGATCAG | CCCTTAACTGCCCTGAAT | 1136, 1280 | 2298 | 10 |
| 16 | 21206262 | CITCCTGACAATGCTTGG | AGCCAACATACCTGCTCA | 1137, 1281 | 2143 | 20 |
| 17 | 18974210 | AACGGCATGTAGATGTGGTG | GCACCTAGTGGCACCCAT | 1138, 1282 | 2105 | 19 |
| 18 | 19807524 | TGTCCCTGTTCTTATGGTGG | TATCCACACCCAGGGACC | 1139, 1283 | 2069 | 9 |
| 19 | 19667884 | GCAGGTCGATAACTCATCAC | TATAGATGTCACCGGGCA | 1140, 1284 | 2040 | 22 |
| 20 | 20052309 | CATCAGTGAGCAGAGCTGT | CAGAGGATGTCATCTGTGTG | 1141, 1285 | 1992 | 16 |
| 21 | 19375345 | GATGGCTTCCTTAGTTCACC | GCTATTTTAGCCCCCTTTG | 1142, 1286 | 1952 | 14 |
| 22 | 19045147 | TTCCAGGTTCCTTCATAATG | CCAATACTCCAGGCAACA | 1143, 1287 | 1947 | 14 |
| 23 | 18501608 | CCCTTCCCTTCAAGAATC | GAAAGCTAGCGCAAGAAA | 1144, 1288 | 1934 | 13 |
| 24 | 21417928 | CCATTGACATGAGATTCTCC | GCTCTCCGAATTTCCCTA | 1145, 1289 | 1886 | 16 |
| 25 | 19717872 | TCCAGGGGTGTCTCAGAG | TGTGGAACTAGACTATGGGG | 1146, 1290 | 1838 | 14 |
| 26 | 18926646 | AGCTTGAGGTCATCCACA | GTCCCAACTCTCTCAGATTG | 1147, 1291 | 1825 | 10 |
| 27 | 20915086 | GGGGATGAAACCTTGAAG | TGTCATGTTCTCCTTCCG | 1148, 1292 | 1818 | 18 |
| 28 | 21307202 | AGCTAGGCTTGAACTGGAA | CTCACCAGGTCTGCTTCA | 1149, 1293 | 1814 | 16 |
| 29 | 18622362 | GTCATGGACCTAATCTTCA | CAATATATTGCTAGGGGG | 1150, 1294 | 1813 | 11 |
| 30 | 20251445 | ACGCCACTGTTGCTAAGA | TACACCACTTTGCTGCCT | 1151, 1295 | 1772 | 12 |
| 31 | 20306765 | AAGGAGTGCAGCAATCTG | CAGATCCCGAAGATTGTG | 1152, 1296 | 1759 | 16 |
| 32 | 20490926 | ATCTAGTGCAGGTGCCACT | GTCGTGCGAATTGAAGTC | 1153, 1297 | 1756 | 11 |
| 33 | 18586568 | AGATGGAGCTAGATTTGAA | GGTAACATTCATCGGAGT | 1154, 1298 | 1752 | 13 |
| 34 | 20368441 | TTAGGAGGCAGGTCTCAGA | ATCACCGGCCTAATCCAT | 1155, 1299 | 1731 | 13 |
| 35 | 19343527 | GTCCGGATGAAATCCATG | AATAGCTGAGCGCCATGT | 1156, 1300 | 1725 | 13 |
| 36 | 20033830 | CCCAAGTAATGGCCCATAAC | GCAAGCCGTATCCCAAGT | 1157, 1301 | 1668 | 18 |
| 37 | 20049273 | CCAGCACTAGTCGTACTTCA | CTGATAGGATTTGGGCTG | 1158, 1302 | 1666 | 11 |
| 38 | 19868750 | GGGGCTGTACTTGTATGTCT | CACTGGCCAGAGTTTTTC | 1159, 1303 | 1665 | 10 |
| 39 | 21399267 | GGTATACCTAGAGCTTTATGGTG | GGAGAATACCTGGAAGTTTAGA | 1160, 1304 | 1663 | 14 |
| 40 | 20468482 | TCTCTAGTAACCATCAGGGC | GGATGGAAATCTAGATGTTTCT | 1161, 1305 | 1654 | 18 |
| 41 | 18588316 | TTCACTCTTCCTGCATCC | GGAGGCTAGCGTTATTAGC | 1162, 1306 | 1645 | 9 |
| 42 | 18421455 | ATCCATATCCGGCAAAAT | AGGCAGAGATGCAGACAA | 1163, 1307 | 1595 | 9 |
| 43 | 21112602 | ACTCAACACCTGCTTTGG | TGGTTCAGCTCAGGGATA | 1164, 1308 | 1589 | 14 |
| 44 | 21193715 | GCTCTTTAGCACACGATTC | CCTCCAAATGAAGTGACC | 1165, 1309 | 1583 | 22 |
| 45 | 18398783 | GAACCAGTGGGTCAAAAA | CAGCCCACACAGACTAAA | 1166, 1310 | 1568 | 10 |
| 46 | 19295732 | GTGGATCTGTGCCCTAAA | GACAACTGCAGGATCGAT | 1167, 1311 | 1566 | 10 |
| 47 | 20261589 | TTCCTTCCTCGGAAGTTC | TGTTAATGGGTCTCTCTTGG | 1168, 1312 | 1554 | 12 |
| 48 | 19351820 | AGAACCGGTCAGGCCTTCAT | CTGCCGCCTGGTCAAAAA | 1169, 1313 | 826 | 18 |

TABLE 3 -continued

PCR primers used for amplifying 3.4 MB region of *X. laevis* for locus labeling.

| | Amplicon position on Scaffold 102974 | Forward primer | Reverse primer | SEQ ID NO | Product length | Guides contained |
|---|---|---|---|---|---|---|
| 49 | 20613373 | GCCCCAGAATCTTAACGT | TTGGGTAGAGGGACACTATG | 1170, 1314 | 1540 | 12 |
| 50 | 21179635 | GCCCCCTAGTTTATTAACC | TGCAGGTGACATAGCACT | 1171, 1315 | 1528 | 11 |
| 51 | 20476167 | CTCCTAGATCCCCCTACATT | CCTTCTCACAAGACAGTTCC | 1172, 1316 | 1521 | 11 |
| 52 | 18243269 | CCCTAGGCCAGTATAGGAT | GAAAGATATTGTCCCCCTC | 1173, 1317 | 1517 | 13 |
| 53 | 20068811 | CGTAGGATCCATCGATGA | GCGACTTGATTCCTTGTG | 1174, 1318 | 1509 | 10 |
| 54 | 19804952 | TGTTCTTAGGACAGTAGGGC | TCCCTTGCTACCTTGTTG | 1175, 1319 | 1484 | 12 |
| 55 | 20242549 | TGCTCTAGCATCAATGGAT | GGTTTCTTGCAGTTACCG | 1176, 1320 | 1466 | 11 |
| 56 | 20279182 | TGGTTGGACCTTCACTTG | TATGTGGGTGTTCAAGGC | 1177, 1321 | 1466 | 10 |
| 57 | 20244393 | CTGGACTCTAGGTTAGCTTTACA | ATGGGCCATTTCAGGTAT | 1178, 1322 | 1444 | 19 |
| 58 | 21468108 | ATTCGTCACTGGGGGACT | GGGGATGATAGCAGCTACAA | 1179, 1323 | 1409 | 10 |
| 59 | 18289194 | AATGCACCGTATAATAGGTT | CTGGGCACTATATAGTCAGAC | 1180, 1324 | 1400 | 10 |
| 60 | 19665648 | GCTGTCCATTGTGAGTCTAC | GCAACCTGGAGTCCATAT | 1181, 1325 | 1399 | 11 |
| 61 | 18320870 | AACTAGTGCAGCTTCCAAGG | GACCAAGTGGCAAAAACG | 1182, 1326 | 1395 | 9 |
| 62 | 19347477 | ATGTTGTGGGTCAGATGC | GTTGGATCACCTGTGCAT | 1183, 1327 | 1389 | 10 |
| 63 | 20216137 | TTGTCACGTTAGTTCCCC | GGGGAGATTCCACACTTT | 1184, 1328 | 1373 | 22 |
| 64 | 21116309 | GAGGTCCATTGGTCCATT | AAGGCTGGTTGGAGTCAT | 1185, 1329 | 1363 | 12 |
| 65 | 19763296 | AGCTATCCGCTCATCACA | ACTGAGTGCAGGTTCTGTCT | 1186, 1330 | 1362 | 12 |
| 66 | 19098872 | GTTTTTCCCTAAGCCGAG | GACCCTTTTAGGTGACCA | 1187, 1331 | 1361 | 10 |
| 67 | 21163618 | GAGAGCAGTAATTACCATAAGCC | AAAGGTTTTGGGGACTC | 1188, 1332 | 1358 | 16 |
| 68 | 20321060 | CCCCTAGTCTTCACATTCC | TGTCCCCTCTTTGCTATG | 1189, 1333 | 1355 | 13 |
| 69 | 18677446 | TCAGACCATGGTCAGTAAGAC | GCCTATATTGTACTGCGGAG | 1190, 1334 | 1322 | 12 |
| 70 | 20444089 | CTGCCTGATTAATTGAACC | GACATTCGAGTTTCAGAGG | 1191, 1335 | 1320 | 10 |
| 71 | 19621992 | CCCAGTGGTTTCTATGGA | GATGTCCTCAGAGCTGTTG | 1192, 1336 | 1311 | 12 |
| 72 | 20578164 | TAGGCCTTGGCACTTAAG | TGCTTGACAACTAGGTTTTG | 1193, 1337 | 1309 | 15 |
| 73 | 19588844 | CATGTAGGAAGGACCGTAAG | GAAGACTTACAGTTGCCCTG | 1194, 1338 | 1305 | 9 |
| 74 | 20333650 | TCCTGCATTTGTCCTAGGA | GAAACACCGGGCTCATTG | 1195, 1339 | 1302 | 11 |
| 75 | 18432211 | CTGCTAGGCCAGTTTTGA | GGGGATCTTTATTGCCTAG | 1196, 1340 | 1294 | 12 |
| 76 | 20878833 | ATTGGGCTCACTGAGGAT | CCACATACTAGCGCTATTGAG | 1197, 1341 | 1289 | 15 |
| 77 | 20192536 | TGCTGCGAGTGTCAGTTA | TGTTATCCAGGGAGGTCA | 1198, 1342 | 1258 | 11 |
| 78 | 20648181 | CTGTTCTAGAGGCTGGAACA | CCCTCCAGCCTTAAAGTAAG | 1199, 1343 | 1246 | 13 |
| 79 | 18493381 | CAGAAGCCCAGGTAGACTAA | ACAGCACTCAGGGATCAA | 1200, 1344 | 1244 | 13 |
| 80 | 19884996 | CCAGCCGCTTCTACTTTT | CAGTAAACCCAGTGGCA | 1201, 1345 | 1235 | 14 |
| 81 | 20457042 | TTAGAGCTCACAGGGGAA | GGAACCAGGTGAAAAACA | 1202, 1346 | 1235 | 13 |
| 82 | 19092047 | AAACATTCCTCCGAGCTC | CAACTGTTTAACCAGCGC | 1203, 1347 | 1229 | 16 |
| 83 | 19095805 | ATAGTTCCCAGGTGTGAGC | TCCTGCTAGTCAAGTCTGC | 1204, 1348 | 1229 | 12 |
| 84 | 20393284 | AGCGTTCCACCTCCTTTA | AGGATTGGTTTCTGGTGG | 1205, 1349 | 1195 | 14 |

TABLE 3 -continued

PCR primers used for amplifying 3.4 MB region of X. laevis for locus labeling.

| | Amplicon position on Scaffold 102974 | Forward primer | Reverse primer | SEQ ID NO | Product length | Guides contained |
|---|---|---|---|---|---|---|
| 85 | 18428914 | CACTCGGTGATTCTGTTG | TCTCTCTCTCTCTCTGTG | 1206, 1350 | 1180 | 12 |
| 86 | 20287144 | AAATCACTGCGCTACGTG | AACTCCCAACTTTCCCCT | 1207, 1351 | 1154 | 14 |
| 87 | 19706910 | GCAGGAATGTAGGAATGC | TCACTGAGCTAGTTCATTGG | 1208, 1352 | 1140 | 9 |
| 88 | 19465183 | GAGGGTTGAGCCAAAAGT | GCTTTGAACGAGACATGG | 1209, 1353 | 1135 | 14 |
| 89 | 19131516 | TGCAAACTAGGTAACGAGC | CTCAAGCAAGGTGGAAAC | 1210, 1354 | 1106 | 11 |
| 90 | 19227852 | CCTGTGCTAGTCTTAAGGTCCA | ACCTTCAAGCCGGGCTTC | 1211, 1355 | 1087 | 15 |
| 91 | 18205596 | CGGCAAAAGAGTGATCTAG | AGCAATCATTAGGACCTCA | 1212, 1356 | 1084 | 11 |
| 92 | 20646719 | ACCGAATCCTACTGCATC | TCTCTCATCACTAGGGCC | 1213, 1357 | 1065 | 11 |
| 93 | 19221905 | ACCAGCTTTCATGGTGAC | GCCTATGACAAGTGTTTGC | 1214, 1358 | 1058 | 12 |
| 94 | 19995725 | TGTGCACTAAGCCACATG | TCATCACTGCCCGTAACT | 1215, 1359 | 1023 | 10 |
| 95 | 19429847 | TGGCTAGCATTTCTGAGG | TGGTGTAGCGTGAAACCT | 1216, 1360 | 998 | 9 |
| 96 | 20479566 | GCACCACCATTCAACATTGC | GGTAACCACCGGGCACTG | 1217, 1361 | 997 | 10 |
| 97 | 21315006 | GTACTAGTGCGTTTTACCCAG | GGGCCAGAATAACTCACA | 1218, 1362 | 992 | 15 |
| 98 | 18575559 | TGCTGGTCATGGATTCAC | GCTTCTGTCTAGATCCTTCACA | 1219, 1363 | 985 | 13 |
| 99 | 18555885 | TAAGATTGACACCCCTGC | TGGGATGTCCACAGATCT | 1220, 1364 | 980 | 14 |
| 100 | 18684266 | CACAGTTGCTGGGATAGA | CAGCTCCTGGATATCCTAT | 1221, 1365 | 980 | 9 |
| 101 | 19612841 | AAACGATGCTTCTCCCAG | GCTGCTGGGTATTTCCAT | 1222, 1366 | 979 | 10 |
| 102 | 19847602 | CCAGGTTTCACCGGCAAA | CCAGCCACTGAGGGCTTATTAA | 1223, 1367 | 973 | 12 |
| 103 | 20382290 | CGTGATCATCCCTAGTAAACC | GCGACAAAATAGTCCCGT | 1224, 1368 | 955 | 11 |
| 104 | 19881338 | CCGATAACTTCTCACTCACC | CACTGTGTGTTATGGCGA | 1225, 1369 | 951 | 20 |
| 105 | 19441684 | GGGCTGTGCTTTATCCAT | CTCTCCAGGTCCCTTGAC | 1226, 1370 | 943 | 9 |
| 106 | 19886579 | TGCTTTGCCTGTGCGCTAA | TGCACCGGAGCTCACACA | 1227, 1371 | 939 | 15 |
| 107 | 18886333 | TCTTGCCAATGACTACCG | CGAGGTTGTAACTCTGCTGT | 1228, 1372 | 931 | 14 |
| 108 | 18136707 | ACTTTAGACTAGGGTAATGC | GGGCAAAGAGTTAGGTAC | 1229, 1373 | 929 | 9 |
| 109 | 20397645 | GCCTGGTTCCTACTGGTAC | TCATCCGGAGCAACAGTA | 1230, 1374 | 891 | 12 |
| 110 | 21075883 | TCGCCCGTGTTTGTTGTA | TGCTGACCCTGTGCCTAA | 1231, 1375 | 886 | 10 |
| 111 | 20827899 | CCCAACCACCCTTGTTTT | CAACATGTCCAGGCTGG | 1232, 1376 | 875 | 11 |
| 112 | 21190026 | ATATAGTTGGGGGCCAGTAG | CCATTGTCAACCTGCAAC | 1233, 1377 | 867 | 14 |
| 113 | 18402088 | AGGGAGGCTGAATAATGG | TATAGCGATGAAGCTGCC | 1234, 1378 | 850 | 10 |
| 114 | 19188468 | GGAGGAATGGTCAGTACTGA | ACATCTTTTCTGGCGACA | 1235, 1379 | 841 | 14 |
| 115 | 21001588 | CCCTGTCCTAGAGATTAGTGG | AGGGAGACAAGAACCAGACT | 1236, 1380 | 804 | 11 |
| 116 | 21505465 | TGGCCCTAGGGAGGTTTT | ACCACGGACTGGGAATTACT | 1237, 1381 | 786 | 13 |
| 117 | 20652115 | GCACTACCATTCATGCAT | TCTATGTGTTCTAGCGGT | 1238, 1382 | 779 | 11 |
| 118 | 18355668 | CCTTACTCAAAAGCTAGAATG | CGGGATATAAGACCTCCT | 1239, 1383 | 769 | 9 |
| 119 | 18142271 | ACAGTCATGTTGGGCTTC | ATTGAACTAGAGCGCCAG | 1240, 1384 | 765 | 13 |
| 120 | 20400996 | CGGAGAGCTTACATTTCCT | TCAATGCTTCAACCCAGT | 1241, 1385 | 763 | 12 |

TABLE 3 -continued

PCR primers used for amplifying 3.4 MB region of X. laevis for locus labeling.

| | Amplicon position on Scaffold 102974 | Forward primer | Reverse primer | SEQ ID NO | Product length | Guides contained |
|---|---|---|---|---|---|---|
| 121 | 20910919 | TACAGATCCCCCTGCAGAA | GCCCTATCTTGGCAGGTTAT | 1242, 1386 | 760 | 10 |
| 122 | 18917993 | GGCTCAAAGGGATGTGAT | TGTACTGACTAGGTGGGGG | 1243, 1387 | 749 | 9 |
| 123 | 20032102 | CTCCAGGCCTTCCATCAC | AAAACTTCCGGTTAATAAGGA | 1244, 1388 | 747 | 10 |
| 124 | 20644574 | AATGTCCCCGGCGATACTT | ATTTCGGGGGTCAGCCTATT | 1245, 1389 | 712 | 12 |
| 125 | 19607163 | CTCATTGGATTCCCGGTC | CATGACCCTGACAAGTCCTA | 1246, 1390 | 697 | 16 |
| 126 | 18841592 | CCAGAGCCAACATTAGGGAA | TGGCCCTGGATGCAGAAT | 1247, 1391 | 625 | 9 |
| 127 | 18377849 | CACTCACCCTATCCTATTCCT | GTACTTTGTGCTGCGATTG | 1248, 1392 | 613 | 10 |
| 128 | 19876043 | GCCGTCAAAACACTGTGT | CATTTCAACCGAAAGCAG | 1249, 1393 | 608 | 10 |
| 129 | 20456451 | TGTGCCTGGAATTCATGT | TGGCTGACCGGATTACTA | 1250, 1394 | 602 | 10 |
| 130 | 20570574 | TCTGTTGCCCAACTGAAG | GGTGTCTCATACAAAGGTGC | 1251, 1395 | 588 | 10 |
| 131 | 20097467 | GAGCCAACGACAACAATC | GATCAGTTCCCTCCCAAT | 1252, 1396 | 579 | 10 |
| 132 | 18121076 | TCACTAATCCTAGCACAGAA | AGCTGATCTGATAGGCTG | 1253, 1397 | 575 | 9 |
| 133 | 18563840 | GGGATGATAAGAAAGCCC | CACAGTCTCCTAGCTACAGAGA | 1254, 1398 | 573 | 9 |
| 134 | 20622480 | CTAGGCAAACATTCTGGC | CCAATGTCCTAGGAGTATCG | 1255, 1399 | 561 | 12 |
| 135 | 18398201 | CTGCATTCCCAGTCTATTCC | TTTATTGCCGGCAAAGAC | 1256, 1400 | 547 | 11 |
| 136 | 20104280 | GAGTCATGACCGATACAC | ATTGACCTGGAAGATAAAT | 1257, 1401 | 538 | 11 |
| 137 | 20503070 | ATCACTAGCAAATGCGGG | GTACCTTGCTGGCTATTCCT | 1258, 1402 | 530 | 13 |
| 138 | 19789340 | AGAGGCACCAGGGAACAA | TCAAGGTGGAGATTGCCA | 1259, 1403 | 486 | 11 |
| 139 | 19472457 | CTAGGAATAAGACCCAGTGC | TCCCCTACTGTGAGATATCC | 1260, 1404 | 477 | 9 |
| 140 | 18818946 | GAAAAACCTTGTGGCCTC | TGGGCATCACACTCATCT | 1261, 1405 | 476 | 10 |
| 141 | 19915825 | TCACAATCTCGTCCTCCA | CAGCCGTAGTCCCAATTT | 1262, 1406 | 409 | 10 |
| 142 | 19834738 | CCTGTAGTGTGATTGAGGCT | ACAGGAGAACCGTGGATT | 1263, 1407 | 389 | 10 |
| 143 | 18609457 | CCGGCCCTAATTAACTGA | GGATGGTATGGCATGATCT | 1264, 1408 | 374 | 9 |
| 144 | 20121562 | CACGCCCTAGTGACTCAC | ATCCTCCTTATTGGCTGG | 1265, 1409 | 316 | 11 |

Amplicon names are the position of the amplicon start on X. laevis Scaffold102974 in Xenbase genome v7.1.

Results

When incubated with dCas9-Neon in egg extract, the transcribed pooled PCR product library generated a single major spot in sperm nuclei (FIG. 3B and FIG. 3C), demonstrating that this method provides an innovative, relatively inexpensive, and effective approach for live whole-chromosome labeling.

Figure 4A:
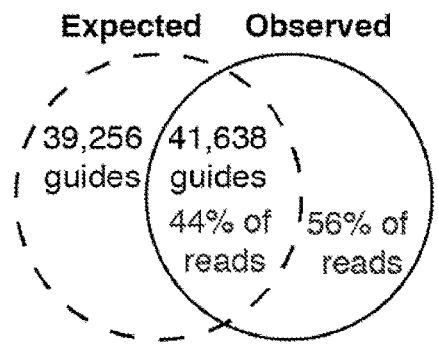
Figure 4B:
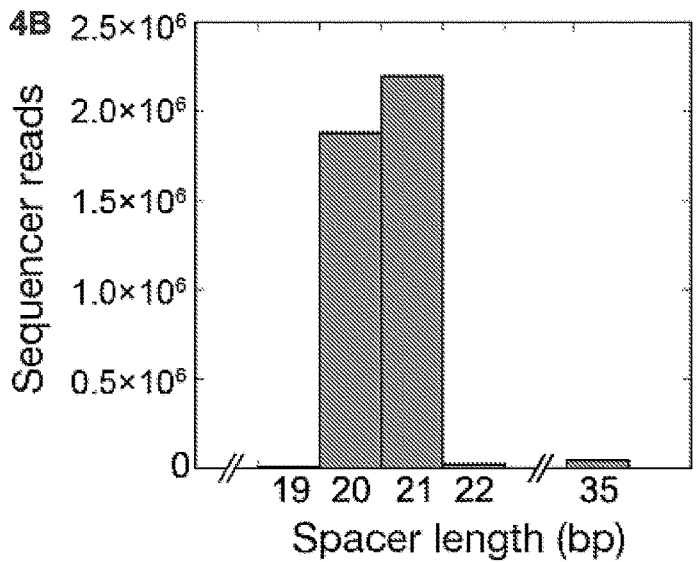

Having shown that the molecular approach to generating a library using the digestion/ligation protocol is possible, we explored its utility in making large, complex libraries suitable for use in genome-wide screens by CRISPR-mediated mutagenesis. In order to simplify analysis of the resulting library, we chose to use the well-characterized E. coli genome as a template. We extracted genomic DNA from a cloning strain of E. coli (XL1-Blue) and subjected it to the digestion/ligation protocol detailed above in parallel duplicates. Using publicly available E. coli genome sequence data, we calculated that 80,894 guides could theoretically be generated using this approach (FIG. 4A). High-throughput sequencing of the library revealed 37,854 guides, at mean incidence of one guide for every 112 nt in the E. coli genome, representing ~44% of the total material sequenced. Of the remaining 56%, 45% of the total material consisted of guides shifted by 1-3 bases 3' relative to PAMs, likely due to promiscuous activity of Mung-bean nuclease used to blunt fragments. The guides were otherwise consistent with the intended design, containing a T7 promoter followed by a 20-21 nt variable region (FIG. 4B) and terminating with a 93 nt invariant region necessary for Cas9 binding.

Figure 4C:
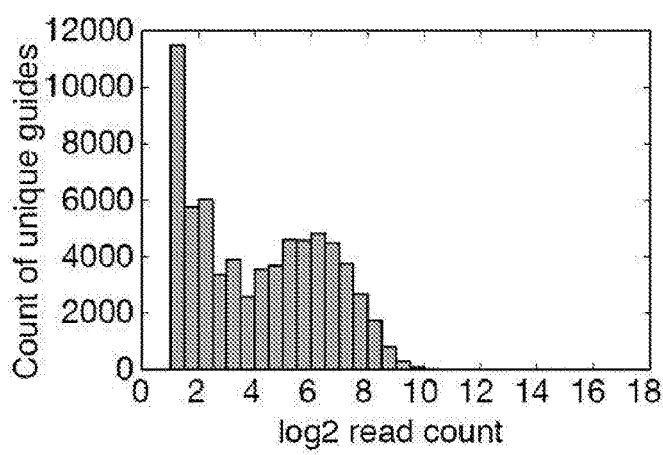
Figure 4D:
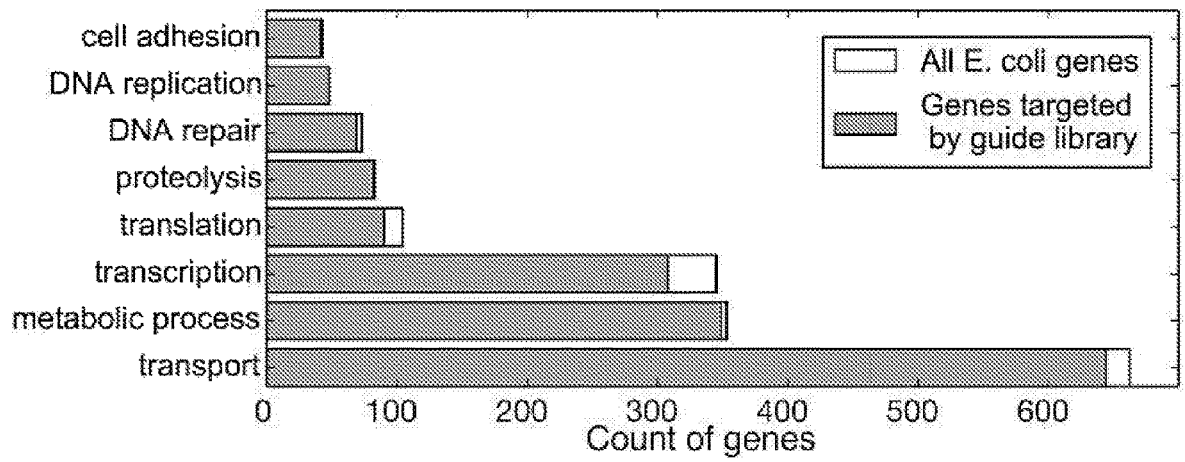

An ideal library is one that exhibits high complexity and is composed of equal numbers of molecules representing each unique guide sequence. However, libraries are subject to deviation from this ideal, due primarily to artifacts introduced during amplification. We analyzed the distribution of unique guide sequences relative to the number of reads obtained in the sequencing data, and found that 90.6% of guides were within 1 standard deviation of the mean abundance and 96.1% of guides were within 2 standard deviations, indicating that only a small proportion of the library content is composed of overrepresented sequences (FIG. 4C). The guide library is predicted to target 3984 of the 4503 genes annotated in the E. coli genome (88%), grouped by GO Term in FIG. 4D. Of the 519 untargeted genes, most are those under 600 nt in length (FIG. 4E). Specificity scoring of all guides indicated that 95.3% of guides predicted to arise from this method have a score of 100/100 (Hsu et al., 2013) indicating that only a single location in the E. coli genome is targeted (FIG. 4F).

Discussion

In summary, we have outlined a simple method to label chromosomal loci in living samples without altering the genome, and an approach to CRISPR library generation that can be used to produce probes to track any locus or make complex libraries for other purposes (e.g., functional genomic methods).

While CRISPR screening libraries generated using synthetic oligonucleotides have been described (Gilbert et al., 2014; Koike-Yusa et al., 2014; Shalem et al., 2014; Wang et al., 2014), so far these libraries target only human and mouse genes. We anticipate that the enzymatic library approach will enable CRISPR-based whole-genome screening in many organisms where oligonucleotide-based design of pooled libraries is undesirable or infeasible for reasons of cost or availability of sequence information. One limitation of our approach is that the precise composition of a guide library cannot be defined as explicitly as it could be in a synthetic oligonucleotide-based library, raising the possibility that individual guides within the library may target more than one location in the genome. We have shown that this is of minimal concern in the small E. coli genome (FIG. 4F). For organisms with larger or unsequenced genomes, the use of a cDNA library rather than total genomic DNA as input is likely to decrease the number of low-specificity guides. Furthermore, most screening strategies can tolerate guides that potentially cut at more than one genomic locus because identification of a "hit" mutation is still possible even if several candidate genomic target sites for an isolated guide must be sequenced.

Applying this technique in an imaging context for use in intact cells or embryos represents a practical way to monitor chromosome dynamics in vivo, something that has been an unreachable goal for many years. The compositions and methods provided here provide the ability to monitor whole chromosomes in live samples. We note that the 3.4 MB region is visible with a mean labeling density of one guide per 2,664 bp, which is unlikely to affect global chromatin state.

This approach to generating guide libraries is termed "CRISPR EATING" (for Everything Available Turned Into New Guides) and anticipate the widespread use of complex guide libraries made using it in a many applications.

Methods

Protein Purification and Designed Guide RNA Production dCas9-Neon was expressed as a 230 kD 6xHis-MBP-TEV-dCas9-Neon-Myc fusion protein in BL21 (DE3) Rosetta2 E. coli and affinity purified using Ni-NTA resin, via the N-terminal His tag. The 6xHis-MBP portion of the protein was removed by specific proteolysis using TEV protease to yield the 186 kD dCas9-Neon-Myc.

Xenopus repetitive sequences were scanned for potential dCas9 targeting sites, which included a 5' GG motif for T7 in vitro transcription (IVT) followed by 18-20 nucleotides (nt) of target sequence and a 3' NGG/NAG protospacer motif for CRISPR/Cas9 binding (Cong et al., 2013; Hsu et al., 2013) using Unipro UGENE software (Okonechnikov et al., 2012). This strategy was previously employed in generating sgRNAs for use by injection into zebrafish embryos (Hwang et al., 2009). sgRNAs were synthesized from DNA templates generated by annealing of a ~59 nt 5' primer containing a T7 RNA polymerase promoter and the desired targeting sequence to an 82 nt 3' primer containing the necessary invariant sgRNA sequence (Hsu et al., 2013). The 5' and 3' primers were annealed over 23 base pairs of reverse-complementarity and extended using a high-fidelity polymerase, resulting in a ~118 base pair double-stranded substrate for use in in vitro transcription reactions. Resulting 100-102 nt RNAs were folded at 60° C. and combined with dCas9-Neon at 37° C. using 2 μl-5 mg/ml dCas9 with 5 μl IVT reaction product which generally ensured a large molar excess of RNA such that all protein was RNA-bound.

Xenopus Egg Extract Reactions

Cytostatic factor-arrested (CSF) cytoplasmic extracts were prepared from freshly laid eggs of X. laevis and used for spindle assembly reactions as described (Hannak and Heald, 2006). Progression through interphase was induced by addition of 0.5 mM $CaCl_2$ and incubation for 1-2 hours at room temperature. To induce mitotic structures around replicated chromatin, an equal volume of CSF egg extract was then added. High speed metaphase-arrested extracts in which sperm chromatid condensation and resolution occurs were prepared from CSF extracts by centrifugation at 200,000×g as described (Maresca and Heald, 2006).

Live Imaging

Flow cells were prepared using clean microscope slides, double-sided sticky tape (Scott) and coverslips which have been cleaned by sonication for 20 min in ddH2O with detergent (Versa), rinsed and sonicated in ddH2O for 20 min and stored in 70% Ethanol until use (Stehbens et al., 2012). 8-10 μl of extract were used per flow cell. Flow cells were sealed with VaLaP (Vaseline/Lanolin/Paraffin 1:1:1). CSF flow cells were prepared at room temperature, high-speed flow cells on ice just prior to imaging. Extracts were observed through a 60× 1.49 NA Nikon Apochromat oil immersion objective on a customized spinning disk confocal microscope, equipped with a MS-2000 motorized stage (Applied Scientific Instrumentation), a Borealis-modified Yokogawa CSU-X1 spinning disk head (Spectral Applied Research), an LMM5 laser merge module (Spectral Applied Research), automated emission filter changer (Sutter Instrument) and environmental control (In Vivo Scientific). This setup has been described in detail previously (Stehbens et al., 2012). Images were acquired on a iXon low-light electron multiplication CCD (EMCCD) camera at exposure times of 20-50 ms with EM gain set to 150-200 and 3 MHz readout mode. Neutral density filters reducing laser power to 25-50% were used throughout imaging. Microscope and camera were controlled by Nikon Elements Software (Nikon) running on a 64-bit Microsoft Windows 7 PC. Images were analyzed using Fiji (Schindelin et al., 2012) and assembled in Illustrator (Adobe). Pearson's correlation coefficient was determined using the Coloc2 plugin in Fiji on Z-projections of confocal image stacks; the Pearson's R value (above threshold) is reported.

sgRNA Library Construction

The S. pyogenes Cas9 protospacer-adjacent motif (PAM) consists of an NRG motif, where N is any nucleotide, R is an adenine or guanine nucleotide and G is a guanine nucleotide only. To generate DNA ends that are adjacent to this PAM motif, we employed a restriction enzyme cocktail that recognizes a subset of the possible PAMs within a DNA sequence. HpaII, ScrFI and BfaI recognize the sequences C/CGG, CC/NGG and C/TAG respectively, where "/" indicates the site of phosphodiester backbone cleavage. When a substrate is digested with these enzymes and single-strand overhangs are removed, the remaining dsDNA is that existing immediately 5' to a CGG, NGG or TAG sequence in the target DNA. To trim these blunt-ended PAM-adjacent substrate fragments to 20 nt, we ligated to them an 82 nt dsDNA adapter containing an MmeI recognition site at each terminus, two internal BsaXI sites and an ScrFI site in the middle of the adapter. Following a ligation reaction, products that represent tandems of the adapter are converted back into 82 nt fragments by ScrFI digestion, and those ligated successfully to substrate fragments are trimmed to 41 nt. The 82 nt fragments are removed by Ampure XP SPRI size-selection. Because the MmeI enzyme cuts 20 nt distant from its binding site at the end of the ligated adapter, desired substrate fragments are trimmed to 20 nt by MmeI digestion, producing a 20 nt substrate fragment 5' to a 41 nt half-adapter. The resulting fragments are asymmetrical with respect to their single-strand overhangs, with a 2 nt overhang produced by MmeI digestion on one end and a 1 nt overhang produced by ScrFI digestion on the other end. This allows specific ligation of a T7 RNA polymerase promoter to the end produced by MmeI digestion. The T7 RNA polymerase promoter is constructed from two annealed oligonucleotides, one of which has a two nucleotide "NN" (random base) overhang. Following this ligation step, desired fragments now have a T7 promoter, 20 nt of a PAM-adjacent region, and 41 nt of an adapter fragment. To produce the final sgRNA fragment, the adapter portion is removed using BsaXI within the adapter. Because BsaXI cuts outside of its recognition site, the position of the BsaXI site permits complete removal of the adapter portion of guide fragments, leaving only a 3 nt overhang. This overhang is exploited for ligation of a 93 nt fragment containing the sgRNA constant region. The resulting 136 nt fragment thus consists of a T7 RNA polymerase promoter, 20 nt of sequence corresponding to a putative Cas9 targeting site in the substrate DNA sequence, and 93 nt of sgRNA hairpin. To remove unwanted side products of ligation reactions, the 136 nt fragments were amplified by 10 cycles of PCR using primers in the T7 promoter and at the 3' end of the sgRNA hairpin. The resulting 136 nt band is isolated and purified using DNA-PAGE, whereupon a second round of 10 cycles of PCR amplification is employed to make the final library.

Computational Selection of Guides Across 3.4 MB Region

PCR products used to generate the 3.4 MB region labeling library were selected using a custom computational pipeline employing BioPython to simulate substrate digestion (Cock et al., 2009), BLAST a and a previously published CRISPR scoring algorithm to determine high-scoring guides (Altschul et al., 1990; Camacho et al., 2009; Hsu et al., 2013) and Primer 3 (Untergasser et al., 2012) to generate PCR primers that amplify across regions predicted to produce only high-scoring guides (score of ≥95). Full source code is available at "htt" followed by "ps://git" followed by "hub.c" followed by "om/orgs/eati" followed by "ngcrispr/."

In brief, Scaffold102974 (approx. 21 MB) of X. laevis genome v 7.1 was subjected to this computational pipeline. From within the Scaffold, a 3.4 MB window containing the largest number of highly specific guides (score of 95+) was used. Within that 3.4 MB region, 144 regions containing only guides meeting this score threshold were selected. PCR primers were designed across these regions. A preparation of X. laevis male liver DNA was used as template, and PCRs were carried out using 2×Q5 HotStart Master Mix (New England Biolabs). PCRs were pooled and subjected to the digestion/ligation library protocol using an extended sgRNA constant region.

Detailed Protocol Used

For a schematic illustration of a method encompassing the below, see FIG. 8A. This version of the method does not necessarily require all of the steps below, but the following is an illustration of one way to accomplish such a method.

Enzymatic CRISPR Library Generation

Overview:
1. Prepare input DNA. Pre-dephosphorylate using rSAP.
2. Digest simultaneously using BfaI, HpaII, ScrFI in NEB CutSmart. Use Mung Bean nuclease to remove 5' overhangs.
3. Add MmeI/BsaXI cassette and blunt-ligate.
4. Monomerize tandem adapters by AclI/ScrFI digestion. Remove fragments by Ampure XP size selection.
5. Cleave with MmeI to create 20mer ends with 2 nt overhang.
6. Ligate to annealed T7 fwd oligo containing 2 nt 5' NN overhang.
7. Cleave with BsaXI to remove adapter and generate overhang for sgRNA body ligation
8. Ligate to final sgRNA body.
9. Amplify from both ends and gel purify complete adapters
10. Re-amplify to produce final guide template.

The following reagents were used: BfaI (R0568S), HpaII (R0171S), ScrFI (R0110S), AclI (R0598S), Mung Bean Nuclease (M0250S), Quick ligation kit (M2200S), MmeI (R0637S), BsaXI (R0609S), rSAP (M0371S), T4 PNK (M0201S), 2×Q5 Hot Start Master Mix (M0494S), 10× CutSmart buffer (shipped with most NEB enzymes), Ampure XP beads (Beckman A63880), DNA Clean and Concentrator Columns (Zymo Research D4004), Oligo Binding Buffer (Zymo Research D4060-1), Dialysis discs (Millipore VSWP04700), GelStar (Lonza 50535), Reagents for 15% TBE-PAGE minigels.

All DNA purifications were performed using DNA Clean and Concentrator columns unless otherwise specified. In some cases (e.g., to maintain very small fragments), two volumes of Zymo Oligo Binding Buffer can be used in place of DNA Binding Buffer included in DNA Clean and Concentrator kits. Samples can be stored at −20° C. between steps if necessary.

Linker Preparation

All linkers can be ordered as oligonucleotides. For Linkers 1 and 3, PAGE purification was used. Phosphorylation of the oligonucleotides was performed using T4 polynucleotide kinase (T4 PNK) (NEB) as per manufacturer's protocol (where specified). Annealing was carried out in 1×CutSmart buffer in a PCR machine that was set to ramp from 98° C. to 20° C. over 60 minutes. All completed adapters were drop-dialyzed against ddH2O (using a dialysis disc) for 20 minutes prior to use.

Linker 1 (82 nt) (Adapter1) (see FIG. 9A)

[Each oligo was phosphorylated separately, then the oligos were annealed and the T4 PNK was heat inactivated]

```
Oligo 1:
                                          (SEQ ID NO: 1)
5'-GTTGGATAGTGTACTGCGGCTCC

ATAGACTAGCTCAGGACCAGGATCTTAGATAGTA

ATCAACAGCCCCTCCTAATTCCAAC-3'
```

-continued

Oligo 2 (reverse complement of Oligo 1):
(SEQ ID NO: 2)
5'-GTTGGAATTA*GGAGGGGCTGT*

TGATTACTATCTAAGA*CCTGG*TCCTGAGCTAGTCTA

T*GGAGCCGCAGT*ACACTATCCAAC-3'.

The MmeI sites are underlined only; the BsaXI sites are bold and italic; the ScrFI site is bold, italic, and underlined. The BsaXI sites were used to remove the adapter after use of the MmeI site. BsaXI cuts outside its own recognition site and was positioned to cut within the MmeI sites.

Linker 2 (23+2 nt) (Adapter 2) (see FIG. 9A)

[The "bottom" oligonucleotide was phosphorylated, the T4 PNK was heat-inactivate, and then the "bottom" oligo was annealed to the "top" oligo]

(SEQ ID NO: 3)
Top: 5' gaaat<u>TAATACGACTCACTATAG</u> NN 3'

(SEQ ID NO: 4)
Bottom: 5' <u>CTATAGTGAGTCGTATTA</u>atttc 3'

The T7 RNA Polymerase promoter is underlined (nn indicates degeneracy in the adapter/oligo)

Linker 3 (90+3 nt) (Adapter 3)("DNA Linker")(See FIG. 9A)

[The "top" oligonucleotide was phosphorylated, the T4 PNK was heat-inactivated, and then the "top" oligo was annealed to the "bottom" oligo]

Top:
(SEQ ID NO: 5)
5' TAAGAGCTATGCTGGAAACAGCATAGCAAGTTTAAATAAGGCTAGTC

CGTTATCAACTTGAAAAAGTGGCACCGAGTCGGTGCTTTTTTT 3'

Bottom:
(SEQ ID NO: 6)
5' AAAAAAAGCACCGACTCGGTGCCACTTTTTCAAGTTGATAACGGACT

AGCCTTATTTAAACTTGCTATGCTGTTTCCAGCATAGCTCTTAAAC 3'

Protocol Used
1. In a PCR tube, combine the following:

| | |
|---|---|
| 10 µl | Input DNA at ~1 µg/µl |
| 5 µl | 10X CutSmart Buffer |
| 30 µl | dH2O |
| 1 µl | rSAP |

Incubate at 37° C. for 30 minutes. Heat inactivate at 65° C. for 10 minutes. Recover a 1 µl sample; label it 1. This prevents broken DNA from ligating to adapters in subsequent steps.
2. Split into 3 tubes. Add the following to each tube:

| | |
|---|---|
| 1.5 µl | HpaII (15 U) |
| 1.5 µl | ScrFI (7.5 U) |
| 1.5 µl | BfaI (15 U) |

3. Incubate for ~1 hr at 37° C. Heat inactivate enzymes, 20 min at 80° C. Purify over 1 column each using two volumes of Oligo Binding Buffer, eluting in 10 µl each.
4. In a 50 µl reaction volume containing 2-10 µg DNA in 45 ul water, add 7.5 ul 10× Cutsmart and 2.5 ul MBN reaction buffer. Then, on ice, add 2.5 µl Mung Bean Nuclease to the digested DNA. Incubate in PCR machine at 25° C. for 30 minutes, then cool to 4° C. when done.
5. Add 0.5 µl 1% SDS to the reaction to stop MBN digestion.
6. Transfer to a 1.5 ml tube and add 100 µl (2 volumes) Oligo Binding Buffer. Split over two Zymo columns and elute in 10 µl each. Expect ~75 ng/µl each (about 1 µg total). Nanodrop and recover a 0.5 µl sample; label it 2.
7. Dialyze sample against ddH2O on dialysis disc for 20 minutes to desalt and improve blunt ligation efficiency.
8. For ligations, use extensively dialyzed, phosphorylated MmeI linker (Linker 1):

| | |
|---|---|
| 17 µl | DNA (about 1 to 1.5 µg; equivalent to 10-15 pmol ends at 300 bp) |
| 1 µl | Linker 1 (at 100 pmol/µl) |
| 18 µl | 2X Quick Ligation Buffer |
| 0.5 µl | Quick Ligase |
| 0.5 µl | T4 PNK |

9. Incubate for 30 minutes at RT. (Longer leads to high-molecular-weight products that result in poor recovery from column).
10. Add 200 µl (5 volumes) Zymo DNA binding buffer. Split across 2 Zymo columns and elute in 10 µl each. Measure and recover a 0.5 µl sample; label it 3.
11. To pooled eluates (about 18 µl), add 2.2 µl Cutsmart, 1 µl ScrFI and 1 µl AclI. Incubate at 37° C. for 30 minutes. Take a sample; label it 4. These enzymes break up tandem adapter products into a ~40 bp size that's convenient to remove by Ampure selection.
12. Make up to 50 µl using 1× Cutsmart (i.e., add 28 µl). Add 1.2 volumes (60 µl) Ampure XP beads. Collect on magnet; wash ×2 with fresh 70% EtOH; dry and elute in 10 µl ddH2O. Expect ~10 ng/µl. Label it 5.
13. Digest using MmeI:

| | |
|---|---|
| 9 µl | DNA |
| 1.3 µl | 10X Cutsmart |
| 0.75 µl | 3.2 mM SAM |
| 1 µl | MmeI |

14. Incubate at 37° C. for 1 hour. Inactivate enzyme at 65° C. for 20 minutes. Take a 0.5 µl sample; label it 6. Drop-dialyze against ddH2O 20 mins.
15. Ligate to Linker 2 (T7 promoter):

| | |
|---|---|
| 10 µl | DNA (as much as possible) |
| 1 µl | Linker 2 (at ~58.8 pmol/µl; ~5 X molar ratio) |
| 11 µl | 2X Quick Ligation Buffer |
| 0.75 µl | Quick Ligase |

Incubate for 30 minutes at RT.
16. Add 5 volumes Zymo buffer (110 µl) and purify on a Zymo column (input is ~1.5 µg). Elute in 8 µl. Measure and recover a 0.5 µl sample; label it 7.
17. To the ~7 µl recovered, add 1 µl 10× Cutsmart and 1 µl BsaXI. Incubate at 37° C. for 60 minutes.
18. Drop-dialyze samples against ddH2O, 20 minutes. Wash out dialysis drops with additional 5 µl ddH2O. Take a 0.5 µl sample and label it 8.
19. Ligate to Linker 3 (sgRNA body):

| | |
|---|---|
| 13 µl | DNA [e.g. 600 ng = 11 pmol] |
| 1 µl | Linker 3 (at 38.1 pmo/µl, this is ~3.5 X molar ratio) |

-continued

| 14 µl | 2X Quick Ligation Buffer |
| 0.75 µl | Quick Ligase |

20. Add 150 µl (5 volumes) Zymo PCR purification buffer. Purify over a column; elute in 10 µl/column. Nanodrop and recover a 0.5 µl sample; label it 9.
21. PCR-amplify ligation product

| 2 µl | Ligation product |
| 1.25 µl | T7 fwd amplification oligo (0.5 µM final) |
| 1.25 µl | 3' sgRNA constant region oligo (0.5 µM final) |
| 12.5 µl | 2X Q5 HotStart Master Mix |
| 8 µl | ddH2O |
| 98° C. | 30 s |
| 98° C. | 10 s |
| 59° C. | 30 s } ×10 |
| 72° C. | 30 s |
| 72° C. | 2 min |
| 12° C. | inf. |

22. Label PCR product sample 10. Run gel to check library for presence of 136 bp band (15% TBE-PAGE minigels)
23. Add 20 µl 10×DNA loading dye to ~22.5 µl remaining PCR product. Run out entirety of PCR product across 4 lanes of a 10-well gel and stain 20 min with two drops of EtBr or (preferably) GelStar in 50 ml buffer.
24. Cut out 136 bp band under UV or (preferably) blue light illuminator, place in 0.6 ml tube. Crush gel slice and add 100 µl Crush-and-soak buffer (1 mM EDTA, 0.1% SDS, 0.3M NaAc 5.2). Incubate rotating overnight at room temperature.
25. Spin through a 0.2 µm spin filter (3 min, max speed). Wash out incubation tube with 500 µl Zymo DNA binding buffer and spin this through the same filter. Column-purify; elute in 20 µl. If the end-point of ligation of guides into a vector, steps 26-27 may not be necessary.
26. Repeat the PCR as step 21, scaled up to 3×50 µl reactions and using 3 µl template for each 50 µl reaction for 12 cycles.
27. Purify PCR products over Zymo column and measure concentration.
28. Transcribe library using T7 RNA polymerase or phosphorylate and clone into a vector for propagation.
29. Troubleshooting: Analyze numbered samples on 15% TBE-PAGE gel to determine presence of DNA, enzyme activity and ligase activity.

REFERENCES

Altschul, S. F., Gish, W., Miller, W., Myers, E. W., and Lipman, D. J. (1990). Basic local alignment search tool. J. Mol. Biol. 215, 403-410.
Bassham, S., Beam, A., and Shampay, J. (1998). Telomere variation in *Xenopus laevis*. Mol. Cell. Biol. 18, 269-275.
Camacho, C., Coulouris, G., Avagyan, V., Ma, N., Papadopoulos, J., Bealer, K., and Madden, T. L. (2009). BLAST+: architecture and applications. BMC Bioinformatics 10, 421.
Chen, B., Gilbert, L. A., Cimini, B. A., Schnitzbauer, J., Zhang, W., Li, G.-W., Park, J., Blackburn, E. H., Weissman, J. S., Qi, L. S., et al. (2013). Dynamic Imaging of Genomic Loci in Living Human Cells by an Optimized CRISPR/Cas System. Cell 155, 1479-1491.
Cock, P. J. A., Antao, T., Chang, J. T., Chapman, B. A., Cox, C. J., Dalke, A., Friedberg, I., Hamelryck, T., Kauff, F., Wilczynski, B., et al. (2009). Biopython: Freely available Python tools for computational molecular biology and bioinformatics. Bioinformatics 25, 1422-1423.
Cong, L., Ran, F. A., Cox, D., Lin, S., Barretto, R., Habib, N., Hsu, P. D., Wu, X., Jiang, W., Marraffini, L. A., et al. (2013). Multiplex genome engineering using CRISPR/Cas systems. Science (80-.). 339, 819-823.
Freeman, J. L., and Rayburn, A. L. (2005). Localization of repetitive DNA sequences on in vitro *Xenopus laevis* chromosomes by primed in situ labeling (PRINS). J. Hered. 96, 603-606.
Gilbert, L. A., Larson, M. H., Morsut, L., Liu, Z., Brar, G. A., Torres, S. E., Stern-Ginossar, N., Brandman, O., Whitehead, E. H., Doudna, J. A., et al. (2013). CRISPR-mediated modular RNA-guided regulation of transcription in eukaryotes. Cell 154, 442-451.
Gilbert, L. A., Horlbeck, M. A., Adamson, B., Villalta, J. E., Chen, Y., Whitehead, E. H., Guimaraes, C., Panning, B., Ploegh, H. L., Bassik, M. C., et al. (2014). Genome-Scale CRISPR-Mediated Control of Gene Repression and Activation. Cell 159, 647-661.
Hannak, E., and Heald, R. (2006). Investigating mitotic spindle assembly and function in vitro using *Xenopus laevis* egg extracts. Nat. Protoc. 1, 2305-2314.
Hsu, P. D., Scott, D. A., Weinstein, J. A., Ran, F. A., Konermann, S., Agarwala, V., Li, Y., Fine, E. J., Wu, X., Shalem, O., et al. (2013). DNA targeting specificity of RNA-guided Cas9 nucleases. Nat. Biotechnol. 31, 827-832.
Hummel, S., Meyerhof, W., Korge, E., and Knochel, W. (1984). Characterization of highly and moderately repetitive 500 bp Eco RI fragments from *Xenopus laevis* DNA. Nucleic Acids Res. 12, 4921-4938.
Hwang, E., Lee, J., Jeong, J., Park, J., Yang, Y., Lim, J., Kim, J., Baek, S., and Kim, K (2009). SUMOylation of RORα potentiates transcriptional activation function. Biochem. Biophys. Res. Commun. 378, 513-517.
Jinek, M., Chylinski, K., Fonfara, I., Hauer, M., Doudna, J. A., and Charpentier, E. (2012). A programmable dual-RNA-guided DNA endonuclease in adaptive bacterial immunity. Science (80-.). 337, 816-821.
Jinek, M., East, A., Cheng, A., Lin, S., Ma, E., and Doudna, J. (2013). RNA-programmed genome editing in human cells. Elife 2, e00471.
Koike-Yusa, H., Li, Y., Tan, E.-P., Velasco-Herrera, M. D. C., and Yusa, K. (2014). Genome-wide recessive genetic screening in mammalian cells with a lentiviral CRISPR-guide RNA library. Nat. Biotechnol. 32, 267-273.
Maresca, T. J., and Heald, R. (2006). Methods for studying spindle assembly and chromosome condensation in *Xenopus* egg extracts. Methods Mol. Biol. 322, 459-474.
Meyerhof, W., Tappeser, B., Korge, E., and Knochel, W. (1983). Satellite DNA from *Xenopus laevis*: comparative analysis of 745 and 1037 base pair Hind III tandem repeats. Nucleic Acids Res. 11, 6997-7009.
Okonechnikov, K., Golosova, O., Fursov, M., and Team, U. (2012). Unipro UGENE: a unified bioinformatics toolkit. Bioinformatics 28, 1166-1167.
Qi, L. S., Larson, M. H., Gilbert, L. A., Doudna, J. A., Weissman, J. S., Arkin, A. P., and Lim, W. A. (2013). Repurposing CRISPR as an RNA-guided platform for sequence-specific control of gene expression. Cell 152, 1173-1183.
Schindelin, J., Arganda-Carreras, I., Frise, E., Kaynig, V., Longair, M., Pietzsch, T., Preibisch, S., Rueden, C., Saalfeld, S., Schmid, B., et al. (2012). Fiji: an open-source platform for biological-image analysis. Nat. Methods 9, 676-682.

Shalem, O., Sanjana, N. E., Hartenian, E., Shi, X., Scott, D. A., Mikkelsen, T. S., Heckl, D., Ebert, B. L., Root, D. E., Doench, J. G., et al. (2014). Genome-scale CRISPR-Cas9 knockout screening in human cells. Science (80-.). 343, 84-87.

Shaner, N. C., Lambert, G. G., Chammas, A., Ni, Y., Cranfill, P. J., Baird, M. A., Sell, B. R., Allen, J. R., Day, R. N., Israelsson, M., et al. (2013). A bright monomeric green fluorescent protein derived from *Branchiostoma lanceolatum*. Nat. Methods 10, 407-409.

Stehbens, S., Pemble, H., Murrow, L., and Wittmann, T. (2012). Imaging intracellular protein dynamics by spinning disk confocal microscopy. Methods Enzym. 504, 293-313.

Untergasser, A., Cutcutache, I., Koressaar, T., Ye, J., Faircloth, B. C., Remm, M., and Rozen, S. G. (2012). Primer3-new capabilities and interfaces. Nucleic Acids Res. 40.

Wang, T., Wei, J. J., Sabatini, D. M., and Lander, E. S. (2014). Genetic screens in human cells using the CRISPR-Cas9 system. Science (80-.). 343, 80-84.

Wiedenheft, B., Sternberg, S. H., and Doudna, J. A. (2012). RNA-guided genetic silencing systems in bacteria and archaea. Nature 482, 331-338.

Example 2: Example Compositions and Methods for Generating a Library of DNA Molecules that Encode a Cas9 Targeter RNA or a Cas9 Single Guide RNA (sgRNA)

For a schematic illustration of a method encompassing the below, see FIG. 8B; and for specific adapters referred to below see FIG. 9. This version of the method does not necessarily require all of the steps below, but the following is an illustration of one way to accomplish such a method.

Example Uni-Adapter Protocol

This protocol uses a first DNA adapter that includes the constant region of a Cas9 targeter RNA or a Cas9 single guide RNA (sgRNA). The DNA molecules generated by the protocol and some of the intermediates are circular. Thus, the efficiency of the attachment steps (e.g., ligation steps) can be increased due to intramolecular ligation instead of intermolecular ligation at one or more steps. The DNA molecules generated by the protocol can be amplified (e.g., via PCR) and the amplified product used directly to generate Cas9 targeter RNAs or Cas9 sgRNA; or the amplified product can be used to clone the library into a vector such as a plasmid vector (a library of transformable plasmids) or viral vector (library of viral vectors).

Uni-Adapter (Replaces Linker 1 and Linker 3 in the Above Version of the Protocol):

Adapter 1 (can be a PCR product from vector, can be hybridized oligos, etc.) (see FIG. 9 for details)

```
[e.g., Oligonucleotide 1]
                                              (SEQ ID NO: 7)
5' -
GTTGGATAGTGTACTGCGGCTCCATAGACTGTTAAGAGCTATGCTGGAAA
CAGCATAGCAAGTTT
AAATAAGGCTAGTCCGTTATCAACTTGAAAAAGTGGCACCGAGTCGGTGC
CCTGCAGCTGCGA - 3'
```

```
[e.g., Oligonucleotide 2]
(reverse complement of oligo 1)
                                              (SEQ ID NO: 8)
5' -
TCGCAGCTGCAGGGCACCGACTCGGTGCCACTTTTTCAAGTTGATAACG
GACTAGCCTTA
TTTAAACTTGCTATGCTGTTTCCAGCATAGCTCTTAACAGTCTATGGAG
CCGCAGTACAC
TATCCAAC - 3'
```

Preparation:

Starting material is a clone of pUC19 with Uni-Adapter sequence cloned in at SmaI site. Phosphorylate the forward primer below using T4 polynucleotide kinase. Using a phosphorylated F primer results in only that end of the PCR product being efficiently ligatable (hemiphosphorylated blunt ligations happen only at a very low frequency—unphosphorylated blunt ends can, to an approximation, be considered unligatable).

Optional: PCR amplify from plasmid containing this Uni-Adapter using these primers.

```
                                             (SEQ ID NO: 11)
Forward (phosphorylated): GTTGGATAGTGTACTGCGGCTCC (SEQ ID NO: 12)
Reverse: TCGCAGCTGCAGGGCACC
```

Degeneracy Adapter (Replaces Linker 2 in Original Version)

Adapter 2 (see FIG. 9 for details)

```
                                              (SEQ ID NO: 9)
Top: 5' ggtccgacTAATACGACTCACTATAGNN 3'

(SEQ ID NO: 10)
Bottom: 3' acgtccaggctgATTATGCTGAGTGATATC 5'
```

Preparation:

Phosphorylate "bottom" oligonucleotide only. Heat-inactivate T4 PNK and anneal to "top" oligo.

Protocol Modifications:

1. Carry out protocol as previously described up to and including Mung-Bean nuclease blunting.

2. Ligate the Uni-Adapter to the blunted input fragments in place of Linker 1.

3. Some of the Uni-Adapters will have self-ligated; digest with AclI to deconcatamerize (same is in previous protocol).

4. MmeI digest.

5. Ligate degeneracy adapter to the 2 nt overhang generated by MmeI digestion.

6. Digest with PstI to cut within the Uni-Adapter. This reveals an overhang that is compatible with the free end of the degeneracy adapter.

7. Phosphorylate everything in the reaction to ensure that the free end of the degeneracy adapter is now competent to be ligated.

8. Ligate to generate circles: Degeneracy Adapter—variable 20mer—Uni-Adapter.

9. Treat with shrimp antarctic phosphatase to render all free ends unligatable in the next step.

10. Digest the circles with BsaXI. This will "pop out" a 30 nt fragment containing the now unwanted MmeI site and leave a linear molecule with compatible sticky ends at the junction between the variable library 20mer and the start of the guide body.

11. Re-ligate circles closed to produce the final DNA molecules guide.

Optional: PCR amplify using below primers and purify the 142 nt band.

Primers used:

```
                                        (SEQ ID NO: 13)
F: CATGCCTGCAGGTTCCGACTAATACGACTCACTATAG (SEQ ID NO: 14)
R: GTCGACCTGCAGGGCACCGACTCGGTGCCA
```

SbfI Site
Anneals to Guide

Cut PCR product with SbfI to linearize and ligate into pUC19-ΔSbfI (a modified version of pUC19 that removes the SbfI site) at its PstI site. This can be done in the presence of SbfI to deconcatamerize insert guides while ligating (pushes equilibrium to vector+insert, rather than long insert concatamers. Inserts properly ligated to vectors are not cut by SbfI).

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

SEQUENCE LISTING

The patent contains a lengthy "Sequence Listing" section. A copy of the "Sequence Listing" is available in electronic form from the USPTO web site (https://seqdata.uspto.gov/?pageRequest=docDetail&DocID=US11279926B2). An electronic copy of the "Sequence Listing" will also be available from the USPTO upon request and payment of the fee set forth in 37 CFR 1.19(b)(3).

What is claimed is:

1. A method of generating a library of DNA molecules encoding Cas9 single guide RNAs (sgRNAs) or Cas9 targeter RNAs, the method comprising:
    (a) contacting a target DNA molecule with a first DNA endonuclease that specifically binds to and cleaves within a recognition sequence that includes a Cas9 PAM sequence, to generate a plurality of cleavage fragments;
    (b) attaching a first DNA adapter to the plurality of cleavage fragments to generate a plurality of adapter-attached cleavage fragments, each having an adapter segment and a cleavage fragment segment;
    (c) contacting the plurality of adapter-attached cleavage fragments with a second DNA endonuclease that specifically binds to a recognition sequence present in the adapter segment and cleaves within the cleavage fragment segment to generate a plurality of adapter-attached Cas9 guide sequences each having an adapter segment and a guide sequence segment;
    (d) contacting the plurality of adapter-attached Cas9 guide sequences with a third DNA endonuclease that specifically binds to a recognition sequence present in the adapter segment and cleaves at one or more sites to remove all or a portion of the adapter segment, thereby generating a plurality of Cas9 guide sequences; and
    (e) attaching DNA encoding a constant region of a Cas9 sgRNA or a Cas9 targeter RNA to the plurality of Cas9 guide sequences to generate a library of DNA molecules encoding Cas9 sgRNAs or Cas9 targeter RNAs.

2. The method of claim 1, wherein the method incudes a step of circularizing the plurality of adapter-attached Cas9 guide sequences.

3. The method of claim 1 or 2, wherein the first DNA adapter comprises said DNA encoding the constant region of a Cas9 sgRNA or a Cas9 targeter RNA.

4. The method of claim 3, wherein said contacting of step (d) removes a portion of the adapter segment that is present between the Cas9 guide sequence and the DNA encoding the constant region of a Cas9 sgRNA or a Cas9 targeter RNA.

5. The method of claim 1, wherein the third DNA endonuclease of step (d) cleaves at or near the junction of the adapter segment and the guide sequence segment, and removes all or most of the adapter segment from the plurality of adapter-attached Cas9 guide sequences.

6. The method of claim 5, wherein step (e) comprises:
    i) attaching a DNA Linker to the plurality of Cas9 guide sequences, wherein the DNA Linker encodes the constant region of the Cas9 sgRNA or the Cas9 targeter RNA; Or
    ii) inserting the plurality of Cas9 guide sequences into a vector that encodes the constant region of the Cas9 sgRNA or the Cas9 targeter RNA.

7. The method of claim 5, wherein the first DNA adapter comprises two recognition sequences that can be specifically bound by the second DNA endonuclease, wherein the two recognition sequences are positioned at opposite ends of the first DNA adapter such that the second DNA endonuclease will cleave within the cleavage fragment segment regardless of the orientation at which the first DNA adapter is attached to each cleavage fragment of the plurality of cleavage fragments.

8. The method of claim 1, wherein step (a) comprises:
    ii) contacting the DNA molecule with two or more PAM-recognition DNA endonucleases that each specifically binds to and cleaves within a recognition sequence that includes a Cas9 PAM sequence; or
    ii) contacting the DNA molecule with three or more PAM-recognition DNA endonucleases that each specifically binds to and cleaves within a recognition sequence that includes a Cas9 PAM sequence.

9. The method of claim 8, wherein said three or more PAM-recognition DNA endonucleases include BfaI, HpaI, and ScrFI.

10. The method of claim 1, wherein the second DNA endonuclease cleaves at:
   a) a distance of from 17 to 30 nucleotides from its recognition sequence; or
   b) a site that is 17 to 30 nucleotides from the junction of the adapter segment and the cleavage fragment.

11. The method of claim 1, wherein the generated DNA molecules encoding Cas9 sgRNAs or Cas9 targeter RNAs each include a guide sequence that is in a range of from 17 nucleotides to 25 nucleotides in length.

12. The method of claim 1, wherein the third DNA endonuclease cleaves at a distance of from 1 to 20 nucleotides from its recognition sequence.

13. The method of claim 1, wherein in the method comprises a step of blunting cleavage products that are produced by one or more of said steps (a), (c), and (d).

14. The method of claim 1, wherein in the method comprises a step of attaching a second DNA adapter to the plurality of adapter-attached Cas9 guide sequences generated in step (c), wherein the second DNA adapter comprises (i) an RNA polymerase promoter positioned such that it is operably linked to the Cas9 guide sequences once the second DNA adapter is attached, and/or (ii) an overhang or recognition sequence for cloning or circularization.

15. The method of claim 14, further comprising contacting the library of DNA molecules encoding Cas9 sgRNAs or Cas9 targeter RNAs with an RNA polymerase to generate a library of Cas9 sgRNAs or Cas9 targeter RNAs.

* * * * *

UNITED STATES PATENT AND TRADEMARK OFFICE
CERTIFICATE OF CORRECTION

PATENT NO. : 11,279,926 B2
APPLICATION NO. : 15/765420
DATED : March 22, 2022
INVENTOR(S) : Andrew B. Lane et al.

It is certified that error appears in the above-identified patent and that said Letters Patent is hereby corrected as shown below:

In the Specification

In Column 1, Line 8, please replace "files" with --filed--

In Column 32, Line 60, please replace "1μme" with --1 times--

In Column 49, Table 3, please replace "16 21206262 CITCCTGACAATGCTTGG" with --CTTCCTGACAATGCTTGG--

In Column 55, Table 3, please replace
"141 19915825 TCACAATCTCGTCCTCCA    CAGCCGTAGTCCCAATTT" with
--141 19915825 CAGCCGTAGTCCCAATTT   TCACAATCTCGTCCTCCA--

In the Claims

Column 67, Line 65, Please replace Claim 3 "The method of claim 1 or 2, wherein the first DNA adapter comprises said DNA encoding the constant region of a Cas9 sgRNA or a Cas9 targeter RNA." with --The method of claim 1, wherein the first DNA adapter comprises said DNA encoding the constant region of a Cas9 sgRNA or a Cas9 targeter RNA.--

Signed and Sealed this
Twelfth Day of July, 2022

Katherine Kelly Vidal
*Director of the United States Patent and Trademark Office*